US012153054B2

United States Patent
Sato et al.

(10) Patent No.: US 12,153,054 B2
(45) Date of Patent: Nov. 26, 2024

(54) METHOD FOR ISOLATING CELL NUCLEI HAVING ENHANCED ANTIGENICITY FROM FIXED CELLS OR FFPE TISSUE SECTION, AND ANTIGEN ACTIVATOR AND KIT THEREFOR

(71) Applicant: NITTO BOSEKI CO., LTD., Fukushima (JP)

(72) Inventors: Natsuki Sato, Tokyo (JP); Mika Kuroiwa, Tokyo (JP); Masatoshi Nakatsuji, Kawasaki (JP); Hideki Ishihara, Tokyo (JP)

(73) Assignee: NITTO BOSEKI CO., LTD., Fukushima (JP)

( * ) Notice: Subject to any disclaimer, the term of this patent is extended or adjusted under 35 U.S.C. 154(b) by 1031 days.

(21) Appl. No.: 16/975,930

(22) PCT Filed: Feb. 28, 2019

(86) PCT No.: PCT/JP2019/007757
§ 371 (c)(1),
(2) Date: Aug. 26, 2020

(87) PCT Pub. No.: WO2019/168085
PCT Pub. Date: Sep. 6, 2019

(65) Prior Publication Data
US 2020/0408770 A1 Dec. 31, 2020

(30) Foreign Application Priority Data
Feb. 28, 2018 (JP) .................................. 2018-035696

(51) Int. Cl.
G01N 33/68 (2006.01)
C12Q 1/6886 (2018.01)
G01N 1/30 (2006.01)
G01N 33/574 (2006.01)

(52) U.S. Cl.
CPC .......... *G01N 33/6875* (2013.01); *G01N 1/30* (2013.01); *G01N 33/57496* (2013.01); *C12Q 1/6886* (2013.01); *C12Q 2600/106* (2013.01); *C12Q 2600/118* (2013.01); *C12Q 2600/158* (2013.01); *G01N 2333/435* (2013.01); *G01N 2333/47* (2013.01); *G01N 2333/4742* (2013.01); *G01N 2333/723* (2013.01); *G01N 2800/52* (2013.01)

(58) Field of Classification Search
CPC ............. G01N 1/30; G01N 33/57496; G01N 2333/435; G01N 2333/4742; G01N 2333/723; G01N 2800/52; C12Q 1/6886
See application file for complete search history.

(56) References Cited

U.S. PATENT DOCUMENTS

| | | |
|---|---|---|
| 7,560,282 B2 | 7/2009 | Gerdes |
| 2005/0221399 A1 | 10/2005 | Nakano et al. |
| 2007/0077577 A1 | 4/2007 | Almouzni et al. |
| 2007/0207489 A1 | 9/2007 | Pestano et al. |
| 2009/0298703 A1 | 12/2009 | Gough et al. |
| 2011/0091907 A1 | 4/2011 | Kataoka et al. |

FOREIGN PATENT DOCUMENTS

| | | |
|---|---|---|
| CN | 102027372 A | 4/2011 |
| CN | 104892759 A | 9/2015 |
| EP | 0 806 668 A2 | 11/1997 |
| JP | H11-509930 A | 8/1999 |
| JP | 2003506716 A | 2/2003 |
| JP | 2005315862 A | 11/2005 |
| JP | 2007524103 A | 8/2007 |
| JP | 2009063508 A | 3/2009 |
| JP | 2009122115 A | 6/2009 |
| JP | 2009527740 A | 7/2009 |
| JP | 2009537822 A | 10/2009 |
| JP | 2013200287 A | 10/2013 |
| WO | WO 2001/11361 A2 | 2/2001 |
| WO | WO 2002/068655 A | 6/2002 |
| WO | WO 02/068655 A1 | 9/2002 |
| WO | WO 2002/068655 A1 | 9/2002 |

(Continued)

OTHER PUBLICATIONS

Shikamata et al. JP2013200287. Machine translation generated in Espacenet. p. 1-18. (Year: 2013).*
Schutte B et al. Flow cytometric Determination of DNA Ploidy Level in Nuclei Isolated from Paraffin-Embedded Tissue. 1985. Cytometry. 6:26-30. (Year: 1985).*
Sheri, A. et al., "Developments in Ki67 and other biomarkers for treatment decision making in breast cancer," *Annals of Oncology*, vol. 23, Supplement 10, pp. x219-x227 (2012).
Notice of Reasons for Refusal issued for the Japanese counterpart application, Appl. No. 2020-503605, mailed Mar. 26, 2021 (English translation included).

(Continued)

*Primary Examiner* — Paul J Holland
(74) *Attorney, Agent, or Firm* — Crowell & Moring LLC

(57) ABSTRACT

Provided are a pretreatment method for detecting the number of cells containing Ki-67 protein-positive nuclei using Ki-67 antibody; a method for the detection; a kit to be used in the detection method; and determination of a therapy regimen using the aforesaid method. Attempts were made to activate Ki-67 antigen with the use of an enzyme having been considered as inappropriate for the activation thereof. By pretreating a sample with an enzyme not recognizing the epitope of MIB-1 (a rare cutter enzyme), the antigen activation of Ki-67 antigen was enhanced, while enhancing the antigenicity of other antigens including a cytokeratin too. As a result, a method for more objectively and more universally quantifying Ki-67-positive cells at higher reproducibility, said method comprising isolating cell nuclei from an FFPE section while enhancing the antigenicity and performing a reaction between Ki-67 protein, i.e., the target, existing in the cell nuclei with a fluorescently labeled antibody, has been completed.

17 Claims, 27 Drawing Sheets

Specification includes a Sequence Listing.

(56) References Cited

FOREIGN PATENT DOCUMENTS

| WO | WO-2009128917 A2 * | 10/2009 | ........... A61K 31/337 |
|----|----|----|----|
| WO | WO 2019/168085 | 9/2019 | |

OTHER PUBLICATIONS

First Office Action, including Search Report, issued in related Chinese Application No. 201980015834.0, dated Jun. 9, 2021 (translated into English).
"Guideline for Breast Cancer Diagnosis Based on Scientific Evidence, 1 Therapy Edition," *Japanese Breast Cancer Society* (2015) (English partial translation provided).
Tuominen, V.J., et al., "ImmunoRatio: a publicly available web application for quantitative image analysis of estrogen receptor (ER), progesterone receptor (PR), and Ki-67," *Breast Cancer Research*, 12:R56, 12 pages (2010).
"The Japanese Breast Cancer Society Clinical Practice Guidelines for Breast Cancer 2018," *Japanese Breast Cancer Society*, 4$^{th}$ edition, pp. 276-280 (2018) (English partial translation provided).
(*) "The Japanese Breast Cancer Society Clinical Practice Guidelines for Breast Cancer 2015," *Japanese Breast Cancer Society*, 3$^{rd}$ edition (2015).
Leers, M.P.G., et al., "Multi-Parameter Flow Cytometric Analysis With Detection of the Ki67-Ag in Paraffin Embedded Mammary Carcinomas," *Cytometry*, 27:283-289 (1997).
Dowsett, M., et al., "Assessment of Ki67 in Breast Cancer: Recommendations from the International Ki67 in Breast Cancer Working Group," *JNatl Cancer Inst*, 103(22):1656-1664 (2011).
Toss, A. and Cristofanilli, M., "Molecular characterization and targeted therapeutic approaches in breast cancer," *Breast Cancer Research*, 17:60, (2015)—11 pages.
Polley, M-Y.C., et al., "An International Ki67 Reproducibility Study," *J Natl Cancer Inst*, 105:1897-1906 (2013).
Gorman, B.K., et al., "Comparison of Breast Carcinoma Prognostic/Predictive Biomarkers on Cell Blocks Obtained by Various Methods: Cellient, Formalin and Thrombin," *Acta Cytologica*, 56:289-296 (2012)
"Guideline for Breast Cancer Diagnosis Based on Scientific Evidence 2, Epidemiology/Diagnosis Edition," *Japanese Breast Cancer Society*, pp. 225-245 (2015) (English partial translation provided).
Goldhirsch, A., et al., "Personalizing the treatment of women with early breast cancer: highlights of the St Gallen International Expert Consensus on the Primary Therapy of Early Breast Cancer 2013," *Annals of Oncology*, 24:2206-2223 (2013).
Goldhirsch, A., et al., "Strategies for subtypes—dealing with the diversity of breast cancer: highlights of the St Gallen International Expert Consensus on the Primary Therapy of Early Breast Cancer 2011," *Annals of Oncology*, 22:1736-1747 (2011).
Schluter, C., et al., "The Cell Proliferation-associated Antigen of Antibody Ki-67: A Very Large, Ubiquitous Nuclear Protein with Numerous Repeated Elements, Representing a New Kind of Cell Cycle-maintaining Proteins," *The Journal of Cell Biology*, 123(3):513-522 (1993).
Sheri, A. & Dowsett, M., "Developments in Ki67 and other biomarkers for treatment decision making in breast cancer," *Annals of Oncology*, 23(Supplement 10):x219-x227 (2012).
Lumachi, F., et al., "Proteomics as a Guide for Personalized Adjuvant Chemotherapy in Patients with Early Breast Cancer," *Cancer Genomics & Proteomics*, 12:385-390 (2015).
Criscitiello, C., et al., "High Ki-67 score is indicative of a greater benefit from adjuvant chemotherapy when added to endocrine therapy in Luminal B HER2 negative and node-positive breast cancer," *The Breast*, 23:69-75 (2014).
Nakamura, H., "Activation/retrieval for Immunostaining," *Regular Meeting of Pathological Study Group, Aichi Association of Medical Technologists*, (2009)—37 pages (English partial translation provided).
International Search Report and Written Opinion received in PCT Application No. PCT/JP2019/007757 dated May 14, 2019.
Huang, Z., "Modern veterinary techniques," *Human Science and Technology Press*, pp. 114-115 (2011).
Wang, W. "Immuno-cellular (tissue) chemistry and molecular pathology techniques," *Fourth Military Medical University Press*, p. 46 (2010).
Second Examination Report issued in the Chinese Application No. 201980015834.0 dated Dec. 15, 2021 (in Chinese and including partial English translation).
Extended European Search Report received in European Application No. 19761170.0 dated May 2, 2022.
English translation of the International Preliminary Report on Patentability and Written Opinion of the International Searching Authority received in PCT Application No. PCT/JP2019/007757 dated Sep. 1, 2020.

* cited by examiner

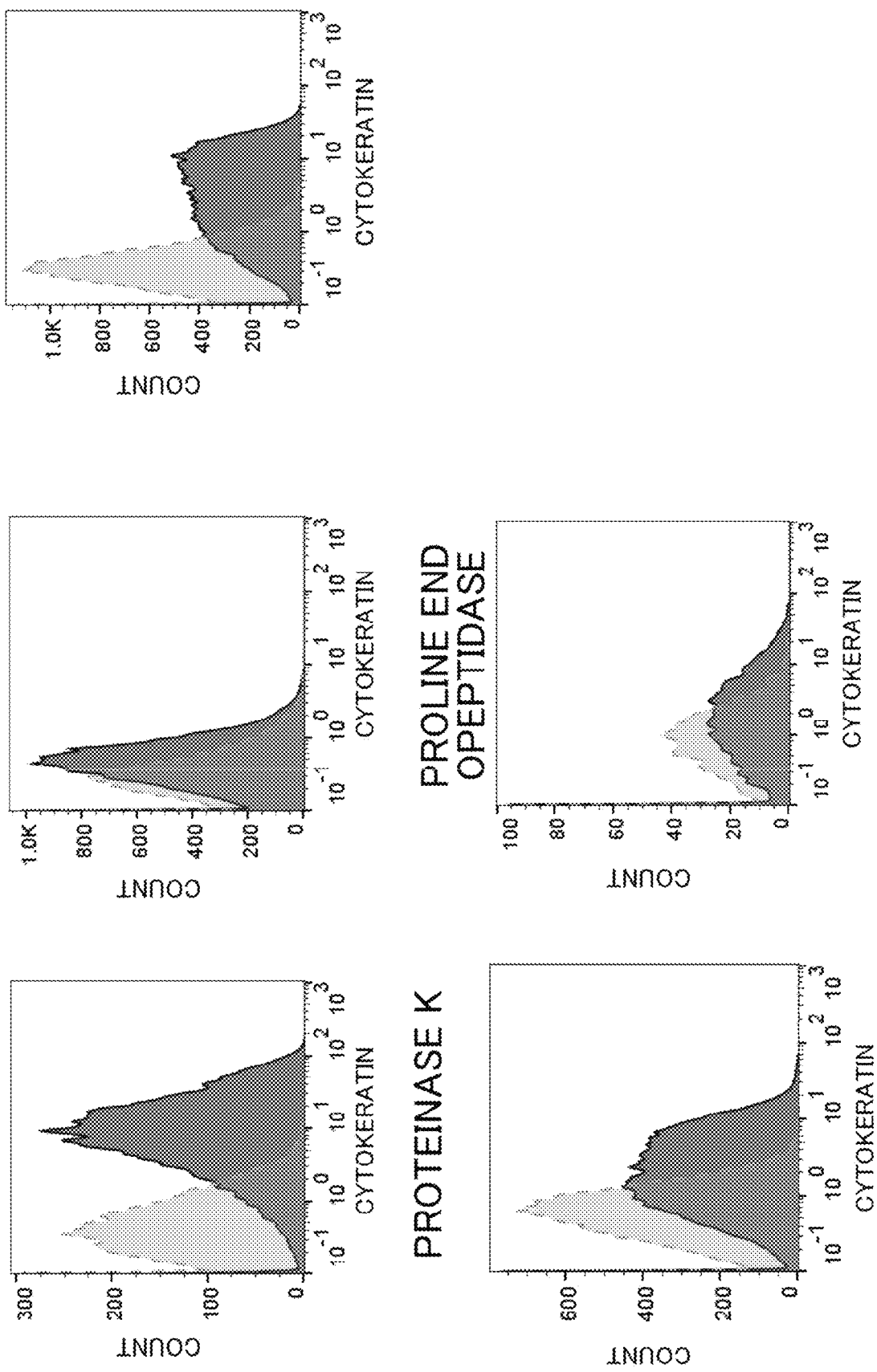

METHOD FOR ISOLATING CELL NUCLEI HAVING ENHANCED ANTIGENICITY FROM FIXED CELLS OR FFPE TISSUE SECTION, AND ANTIGEN ACTIVATOR AND KIT THEREFOR

RELATED APPLICATIONS

This application is a 371 application of PCT/JP2019/007757 having an international filing date of Feb. 28, 2019, which claims priority to JP2018-035696 filed Feb. 28, 2018, the entire content of each of which is incorporated herein by reference.

REFERENCE TO APPENDIX [CD ROM/SEQUENCE LISTING]

This application is being filed electronically via EFS-Web and includes an electronically submitted Sequence Listing in .txt format. The .txt file contains a sequence listing entitled "16325_6_Seq_Listing_ST25" created on Aug. 18, 2020 and is 29,391 bytes in size. The sequence listing contained in this .txt file is part of the specification and hereby incorporated by reference in its entirety.

TECHNICAL FIELD

The present invention relates to a pretreatment method for use in detecting cells containing Ki-67 protein-positive cell nuclei with a Ki-67 antibody, a method for detecting the cells, a kit for use in the pretreatment method or the detection method, and selection of a therapeutic regimen with the detection method.

BACKGROUND

Formalin fixation of a surgically removed tissue is the most common method for preserving a cancer tissue over the world, and serves as a standard pathological technique. The most common method for preserving a tissue includes immersing the entire tissue in an aqueous formalin solution for a long time (8 to 48 hours), and then embedding the fixed tissue in paraffin wax for long-term preservation at room temperature. Accordingly, molecular analysis methods with a formalin-fixed cancer tissue are most commonly used for analysis of, for example, a tissue from a cancer subject.

The immunohistological staining, which is one of diagnostic techniques with a formalin-fixed paraffin-embedded (FFPE) tissue, is a method comprising slicing a tissue to attach the sliced tissue to a slide glass, and then reacting a biological substance present on a surface of the pathological tissue section or the cells with a substance recognizing the biological substance to visualize the antigen-antibody reaction, thereby determining whether the target biological substance exists on the surface of the pathological tissue section or the cells.

For example, the human epidermal growth factor receptor (HER2), the estrogen receptor (ER) and the progesterone receptor (PgR), which are expressed in breast cancer tissues, are considered to be correlated with effects of therapeutic methods, therefore called effect prediction factors, and applied in clinical practice (Non Patent Document 1).

On the other hand, factors of which existence or non-existence has a correlation with prognosis are called prognostic factors. Ki-67 is currently considered to be a prognostic factor. For detection of an effect prediction factor, an immunohistochemical method (IHC method are mainly used for a tumor tissue sample. Any of the following methods is used: a method in which both the staining intensity of tumor cells and a ratio of stained cells are taken into account (Allred Score or the like); and a method in which only a ratio of stained tumor cells is used to make a determination without taking into account the staining intensity (J-Score or the like).

In the case of HER2, examination is performed generally by the IHC. The result is interpreted as negative when a value of 0 or 1+ is obtained, and the result is interpreted as positive when a value of 3+ is obtained. When a value of 2+ is obtained, whether an amplification occurs or not is examined by the FISH method (Fluorescence in situ hybridization). The result is interpreted as positive when an amplification occurs, and the result is interpreted as negative when an amplification does not occur.

In the case of ER, a value of 3 to 8 is considered to be positive according to Allred Score, whereas a cutoff value is often set to 10% when a ratio of stained cells is used to make a determination, but there are arguments that the result should be interpreted as ER-positive as long as stained cells exist even if the ratio thereof is 1%.

In the case of Ki-67, the following methods coexist: a method of calculating a positive ratio in the entire tissue; a method of selecting a region called a hot spot where positive cells congregate and calculating a positive ratio in the spot; and the like.

Whatever the case, once setting a certain cutoff value, it can become an indication of an effective therapeutic regimen when the result for any of these effect prediction factors is interpreted as positive.

The breast cancer is classified into various subtypes according to the expressed levels of the above-described effect prediction factors and prognostic factors.
1) Luminal A (-like) type: ER/PgR-positive, HER2-negative, low Ki-67 level (<14 to 20%)
2) Luminal B (-like) type (HER2-negative): ER/PgR-positive, HER2-negative, high Ki-67 level (≥14 to 20%)
3) Luminal B (-like) type (HER2-positive): ER/PgR-positive, HER2-positive
4) Non-luminal type: ER/PgR-negative, HER2-positive
5) Triple negative type: ER-negative, PgR-negative, HER2-negative These classifications can have an effect on selection of a therapeutic regimen. For example, mainly endocrine therapy alone is selected when the breast cancer is determined as a luminal A (-like) type with a low Ki-67 level, whereas mainly a combination of endocrine therapy and chemotherapy is selected when the breast cancer is determined as a luminal B (-like) type (HER2-negative) with a high Ki-67 level (Non Patent Documents 6 and 10 to 12).

However, in the immunohistological staining method, the above-described determination is made on the basis of visual determination with a microscope, and counting is manually implemented, so that even an experienced pathologist is required to spend time and effort.

Ki-67 (MKI67) is an intranuclear protein and is generally used as a cell proliferation marker. Ki-67 is a molecule expressed on nucleoli of proliferating cells and chromosomes in the nuclear division phase. Ki-67 is expressed in all phases of the cell cycle, and the expression level starts to change in the late G 1 phase, increases in the S phase, and reaches the maximum in the M phase. In this sense, expression of Ki-67 in cells merely indicates that the cells have entered the cell cycle. However, Ki-67 has been used as one of biomarkers in reagents and methods for diagnosis of cancer (Patent Documents 1 to 5), and, in order to save time and effort required for the measurement, cell image automatic analyzers for automatically analyzing cells and methods for automated tissue analysis have been proposed (Patent Documents 6 to 8). In addition, a method of analyzing with an open-sourced software photomicrographic images of cells of which localized nucleus proteins, such as Ki-67, are immunostained is made accessible on a website (Non-Patent Document 2). As described, attempts has been made to introduce image diagnostic techniques, but methods for evaluating Ki-67 have not been standardized, and have been conducted in a variety of ways in respective studies (Non-Patent Document 3).

Attempts have been made to recover nuclei with an enzyme from a FFPE tissue section, which enables long-term preservation of a tissue isolated from a living organism, immunofluorescently stain the nuclei and detect them by FCM, but an enzyme capable of isolating nuclei from a tissue cleaves many parts of a protein, so that there is a high risk of cleaving epitopes. Non-Patent Document 4 reports that regarding antibodies targeting the same protein, for example Ki-67, it was detectable with the clone S5, but was not detectable with the clone MIB-1 having a different antigen-recognition site.

Further, formalin-fixed tissues and thrombin (plasma) fibronectin-fixed tissues may cause the MIB-1 antibody to give a false-positive or false-negative result (Non-Patent Document 9).

However, since IHC methods with MIB-1 have been used in clinical practice for long years, unavailability of antibody clones selected on the basis of experiences causes a heavy loss.

A method of extracting a protein from a FFPE tissue section has been developed, but the method is not intended for detection of existence of antigen-positive nuclei after treatment. A kit for extracting a nucleic acid has been put into practical use, but the kit is no more than a laboratory reagent which cannot be used in clinic use.

PRIOR ART DOCUMENTS

Patent Documents

Patent Document 1: JP 1999-509930 A
Patent Document 2: JP 2003-506716 A
Patent Document 3: JP 2005-315862 A
Patent Document 4: JP 2007-524103 A
Patent Document 5: JP 2009-527740 A
Patent Document 6: JP 2009-63508 A
Patent Document 7: JP 2009-122115 A
Patent Document 8: JP 2009-537822 A Non-Patent Documents Non-Patent Document 1; Evidence-Based Breast Cancer Treatment Guideline, 1. Treatment (Japanese Breast Cancer Society)
Non Patent Document 2: Breast Cancer Research, 2010, 12: R56
Non-Patent Document 3: Breast Cancer Society Guideline (Japanese Breast Cancer Society)
Document 4: Cytometry. 1997 Mar. 1; 27 (3): 283-9. Multi-parameter flow cytometric analysis with detection of the Ki67-Ag in paraffin embedded mammary carcinomas.
Non-Patent Document 5: Dowsett M, et al. Assessment of Ki67 in breast cancer: recommendations from the International Ki67 in Breast Cancer working group. J Natl Cancer Inst. 2011 Nov. 16; 103 (22): 1656-64.
Non-Patent Document 6: Angela Toss, et al. Molecular characterization and targeted therapeutic approaches in breast cancer. Breast Cancer Res. 2015 Apr. 23; 17:60.
Non-Patent Document 7: Leers M P, et al. Multi-parameter flow cytometric analysis with detection of the Ki67-Ag in paraffin embedded mammary carcinomas. Cytometry. 1997 Mar. 1; 27 (3): 283-9.
Non-Patent Document 8: Polley M Y, et al. An international Ki67 reproducibility study. J Natl Cancer Inst. 2013 Dec. 18; 105 (24): 1897-906.
Non-Patent Document 9: Blythe K. Gorman, et al. Comparison of Breast Carcinoma Prognostic/Predictive Biomarkers on Cell Blocks Obtained by Various Methods: Cellient, Formalin and Thrombin. Acta Cytologica 2012; 56:289-296.
Non-Patent Document 10: Evidence-Based Breast Cancer Treatment Guideline, 2. Epidemiology and Diagnosis (Japanese Breast Cancer Society)
Non-Patent Document 11: A. Goldhirsch1, et al. Personalizing the treatment of women with early breast cancer: highlights of the St Gallen International Expert Consensus on the Primary Therapy of Early Breast Cancer 2013. Annals of Oncology 24:2206-2223, 2013.
Non-Patent Document 12: A. Goldhirsch, et al. Strategies for subtypes-dealing with the diversity of breast cancer: highlights of the St Gallen International Expert Consensus on the Primary Therapy of Early Breast Cancer 2011. Annals of Oncology 22:1736-1747, 2011.

SUMMARY

Technical Invention

As described above, an immunohistological staining method involves making a visual examination with a microscope, and making manual counts, which often cause different assessments depending on a pathologist even when the same pathological tissue section is used (see Comparative Example 2). Since an abundance ratio (%) (cutoff value) of Ki-67-positive cells has an effect on selection of a therapeutic regimen, there has been a need for a method for quantitatively determining an abundance ratio of Ki-67-positive cells with higher objectivity, reproducibility and universality.

As described above, a tissue sample, including a pathological tissue section, is prepared and preserved as a standard pathological technique during excision or a biopsy of cancer, and it is therefore preferable that a quantitative determination method can be performed with the preserved sample.

Normally, it is necessary that an extracellular matrix involved in intracellular adhesion be cleaved for antigen retrieval when an analysis with a FFPE tissue is performed at a single cell level. However, digestion of the matrix with an enzyme may cause an epitope of a target antigen to be cleaved, so that usable antibodies are limited. Thus, required are methods for cell dispersion and isolation of cell nuclei other than the above-described existing methods.

Solution to Problem

The present inventors extensively conducted studies. That is, the present inventors conducted studies on a pretreatment with enzymes having been considered to be unsuitable for cell dispersion and isolation of cell nuclei, in which tissues or cells were pretreated with enzymes which does not recognize the epitope of MIB-1 (rare cutter enzymes). Resultantly, the Ki-67 antigen was successfully activated while enhancing the antigenicity of other antigens including cytokeratin. Consequently, a method for detecting Ki-67-positive cells with higher objectivity, reproducibility and universality was established by isolating cell nuclei from a FFPE section while enhancing antigenicity, targeting a Ki-67 protein existing in the nuclei, and reacting an antibody specific to the protein with them.

Accordingly, the present invention relates to [1] to [45] below.

[1] A method for detecting cells containing Ki-67-positive cell nuclei in a population of fixed cells with an anti-Ki-67 antibody, the method comprising the steps of:
  1) activating an antigen by pretreating the population of fixed cells with a hydrolase which does not recognize or cleave a peptide of SEQ ID NO: 2,
  2) then, staining the antigen with the anti-Ki-67 antibody, and
  3) detecting stained Ki-67-positive cells or Ki-67-positive cell nuclei.

[2] The method according to [1], wherein the antibody is at least one selected from the group consisting of MIB-1, DAKO-PC, Ki-S5 and A-0047.

[3] The method according to [1] or [2], wherein the enzyme is at least one selected from the group consisting of thrombin, Arg-C (clostripain) peptidase, proline endopeptidase and hyaluronidase.

[4] The method according to [1], wherein the enzyme is thrombin and/or hyaluronidase, and the antibody is MIB-1.

[5] The method according to any one of [1] to [4], wherein the population of fixed cells is a population of cells fixed with a fixing agent selected from the group consisting of formalin, glutaraldehyde, alcohol, acetone and a combination thereof.

[6] The method according to any one of [1] to [5], further comprising antigen retrieval with heat treatment before step 1).

[7] The method according to any one of [1] to [6], further comprising specifically staining the cell nuclei, and detecting (for example, counting) the stained cell nuclei.

[8] The method according to any one of [1] to [7], further comprising staining (for example, fluorescently staining) cytokeratin with an anti-cytokeratin antibody and detecting stained positive cells.

[9] The method according to any one of [1] to [8], further comprising staining (for example, fluorescently staining) ER and/or PgR with an anti-estrogen receptor (ER) antibody and/or an anti-progesterone receptor (PgR) antibody, and detecting (for example, counting) stained positive cells or positive cell nuclei.

[10] The method according to any one of [1] to [9], further comprising detecting cells or cell nuclei having an amplified HER2 gene with a probe which hybridizes with the HER2 gene.

[11] The method according to any one of [1] to [10], wherein the population of fixed cells is contained in a tissue section.

[12] The method according to [11], wherein the tissue section is embedded in an embedding agent, and the method comprises the steps of removing the embedding agent and hydrophilizing the tissue section before the step of activating the antigen with the hydrolase.

[13] The method according to [11] or [12], comprising the step of extracting the cell nuclei by crushing the cells between steps 1) and 2).

[14] The method according to [13], wherein the cell nuclei are extracted by crushing the cells with shear stress generated by a water flow, ultrasonication or the like.

[15] The method according to [13] or [14], wherein the cell nuclei are extracted in a buffer solution containing a surfactant.

[16] The method according to [15], wherein the surfactant is at least one selected from the group consisting of 3-((3-cholamidopropyl) dimethylammonio)-1-propanesulfonate (CHAPS), Nonyl phenoxypolyethoxylethanol (NP-40) and t-Octylphenoxypolyethoxyethanol (Triton™ X-100).

[17] The method according to any one of [1] to [16], wherein the stained Ki-67-positive cells or Ki-67-positive cell nuclei are counted.

[18] The method according to [17], wherein the Ki-67-positive cells or Ki-67-positive cell nuclei are fluorescently stained, and the cells or cell nuclei are counted by a flow cytometry.

[19] The method according to any one of [1] to [18], wherein the fixed cells or the tissue section is derived from a subject.

[20] The method according to any one of [1] to [18], wherein the fixed cells or the tissue section is derived from a tumor tissue of a subject.

[21] The method according to [20], wherein the fixed cells or the tumor tissue is breast cancer cells or a breast cancer tissue.

[22] The method according to [20] or [21] for assisting diagnosis of cancer.

[23] The method according to [20] or [21] for assisting prognosis of cancer treatment.

[24] A method for determining a cancer therapeutic regimen, the method comprising determining a ratio of Ki-67-positive cells in a population of cells by the method as claimed in [20] or [21], and selecting a combination of endocrine therapy and chemotherapy when the ratio is equal to or more than a cutoff value, while selecting endocrine therapy alone when the ratio is less than the cutoff value.

[25] A method comprising determining a ratio of Ki-67-positive cells in a population of cells by the method described in [20] or [21], selecting a combination of endocrine therapy and chemotherapy when the ratio is equal to or more than a cutoff value, while selecting endocrine therapy alone when the ratio is less than the cutoff value, and applying the selected therapy to a subject to treat cancer.

[26] A method comprising activating Ki-67 by pretreating a population of fixed tumor cells or a tumor tissue with a hydrolase which does not recognize or cleave the peptide of SEQ ID NO: 2.

[27] An antigen activator used for a cell or tissue which is to be subjected to Ki-67 detection by immunostaining, the antigen activator comprising a hydrolase which does not recognize or cleave the peptide of SEQ ID: 2.

[28] The antigen activator according to [27], wherein the enzyme is at least one selected from the group consisting of thrombin, Arg-C (clostripain) peptidase, proline endopeptidase and hyaluronidase.

[29] The antigen activator according to [28], wherein the enzyme is thrombin and/or hyaluronidase.

[30] An antigen activator used for a cell or tissue which is subjected to simultaneous detection of Ki-67 and cytokeratin by immunostaining, the antigen activator comprising a hydrolase which does not recognize or cleave the peptide of SEQ ID: 2.

[31] The antigen activator according to any one of [27] to [30], which is used for a cell or tissue sample which is further subjected to detection of ER and/or PgR by immunostaining.

[32] The antigen activator according to any one of [27] to [31], which is used for a cell or tissue which is further subjected to detection of an amplified HER2 gene.

[33] A kit for detecting Ki-67-positive cells in fixed cells, the kit comprising: a hydrolase which does not recognize or cleave the peptide of SEQ ID NO: 2; and an anti-Ki-67 antibody.

[34] The kit according to [33], wherein the hydrolase is at least one selected from the group consisting of thrombin, Arg-C (clostripain) peptidase, proline endopeptidase and hyaluronidase.

[35] The kit according to [34], wherein the hydrolase is thrombin and/or hyaluronidase.

[36] The kit according to any one of [33] to [35], wherein the anti-Ki-67 antibody is at least one selected from the group consisting of MIB-1, DAKO-PC, Ki-S5 and A-0047.

[37] The kit according to any one of [33] to [36], further comprising a ligand for detecting another maker which is used in combination with Ki-67 for assisting diagnosis of cancer or assisting prognosis of a cancer treatment.

[38] The kit according to [37], wherein the ligand is at least one selected from the group consisting of an anti-cytokeratin antibody, an anti-ER antibody, an anti-PgR antibody, and a probe which hybridizes with a HER2 gene.

[39] The kit according to any one of [33] to [38], further comprising a nucleus staining compound.

[40] The kit according to any one of [33] to [39], further comprising a buffer solution for dispersing cells, the buffer solution containing a surfactant.

[41] The kit according to any one of [33] to [40], further comprising an antigen retrieval agent for use in heat treatment.

[42] The kit according to any one of [33] to [41] for assisting diagnosis of cancer.

[43] The kit according to any one of [33] to [41] for assisting prognosis of a cancer treatment.

[44] The kit according to any one of [33] to [41] for determining a cancer therapy regimen.

[45] The kit according to [044], wherein the therapeutic regime is determined by calculating a ratio of Ki-67-positive cells in a population of cells, and selecting a combination of endocrine therapy and chemotherapy when the ratio is equal to or more than a cutoff value, while selecting endocrine therapy alone when the ratio is less than a cutoff value.

[46] A kit for extracting cell nuclei by crushing fixed cells with shear stress generated by a water flow, ultrasonication or the like, the kit comprising a cell dispersing buffer solution containing a surfactant.

[47] A method for extracting cell nuclei by crushing fixed cells with shear stress generated by a water flow, ultrasonication or the like, the method comprising dispersing the fixed cells in a surfactant-containing buffer solution to crush the cells.

[48] A method for detecting cells of which cell nuclei contain a target antigen in a population of fixed cells with an antibody against the antigen, the method comprising the steps of:
1) activating the antigen by pretreating the population of fixed cells with a hydrolase which does not cleave an epitope which the antibody recognizes or binds to,
2) then, staining the cells with the antibody, and
3) detecting stained antigen-positive cells or antigen-positive cell nuclei.

Advantageous Effects of Invention

According to the present invention, established is a method for detecting (quantitatively determining) Ki-67-positive cells with high objectivity, reproducibility and universality.

The present invention provides a protocol (including a pretreatment reagent and a process) to isolate cell nuclei containing a target antigen with enhanced antigenicity from a FFPE tissue section. The recovered dispersion can be analyzed at a single cell nucleus level. For example, a protein, a nucleic acid or the like on a nuclear membrane or in a nucleus can be an object to be detected and can be detected by staining them with a labeling substance (fluorescent substance, chemiluminescent substance, enzyme or the like) or with an antibody labeled with such a label. In particular, a ratio of positive nuclei containing a target protein in isolated nuclei (Ki-67-positive ratio or the like) can be quickly detected by flow cytometry.

A cutoff value of Ki-67 varied and was different among medical facilities because visual examination and counting by individual pathologists were required. However, the protocol (including pretreatment reagent and process) provided by the present invention can provides a global standard for the cutoff value in pathological diagnosis with small variability.

With such a cutoff value, a diagnostic regimen with high QOL can be provided to a subject.

BRIEF DESCRIPTION OF DRAWINGS

FIG. 13B shows histograms with the fluorescence intensity in the horizontal axis and the number of cells (nuclei) in the vertical axis wherein the histograms were obtained through a process in which a FFPE tissue section of a breast cancer tissue was deparaffinized/hydrophilized, subjected to antigen retrieval with heat treatment, and subjected to antigen activation with any of five digestive enzymes (thrombin, trypsin, proteinase K, dispase and proline endopeptidase), the cells were crushed with a water flow, then immunofluorescently stained with an anti-cytokeratin antibody or an isotype control antibody thereof, and then measured by a flow cytometer, and the data of fractions gated as a group of cell nuclei were analyzed.

EMBODIMENTS OF THE INVENTION

Figure 1:
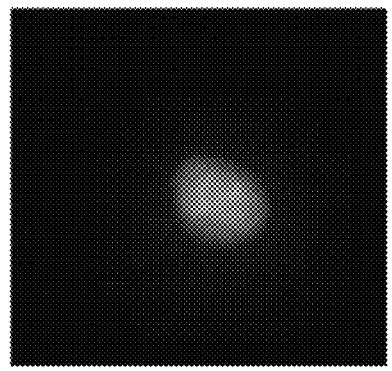
FIG. 1 shows microscopic examination images obtained through a process in which a FFPE tissue section of a breast cancer tissue is deparaffinized/hydrophilized and subjected to antigen retrieval with heat treatment, the cells are crushed with a water flow shear apparatus, and the recovered product is then immuno-fluorescently stained and observed with a microscope. A DAPI-stained nucleus is shown on the left, and a DAPI-stained nucleus and fluorescently labeled cytokeratin (if present) are shown on the right. It is apparent from both the images that the cell nucleus is recovered with maintaining its shape.
Figure 1:
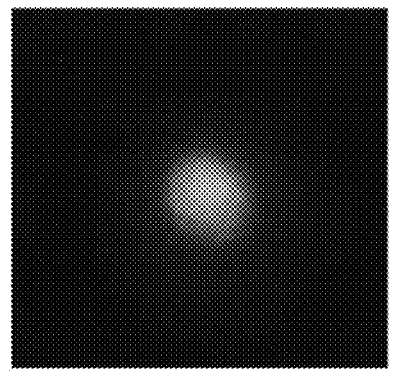

The "fixation of cells" means that a cell form and a tissue structure are stabilized by immersing a sample in a fixing liquid to cause crosslinking of molecules and insolubilization of proteins. A known method may be used for the fixation, and examples of the method include treatments with a formalin liquid, a para-formaldehyde liquid, a glutaraldehyde liquid, an osmium tetraacetate liquid, alcohol acetate, methanol, ethanol, acetone or the like. Alternatively, cells may be fixed by a freezing process.

An "Ki-67 antigen (MKI67: Marker Of Proliferation Ki-67)" is a type of intranuclear protein and is set forth by an amino acid sequence of SEQ ID NO: 1 (3256 amino acids) in the case of humans (UniProt KB-P46013 (KI67_HUMAN)). Ki-67 is originally the name of an antibody discovered as an autoantibody in blood of a patient with leukemia, but as used herein Ki-67 refers to a "Ki-67 antigen" protein unless otherwise specified. Therefore, the "anti-Ki-67 antibody" refers to an "antibody" which recognizes the Ki-67 antigen.

An "antibody" may be a full-length immunoglobulin (IgG, IgA, IgM, IgD or IgE), or a fragment thereof containing an antigen binding and recognition region (i.e., antibody fragment (Fab, Fab', F(ab')2 or the like)). In addition, an "antibody" may be one derived from a mammal such as a human, a mouse, a rat, a goat, a horse or camel, fish (including a shark), or a bird (chicken).

"MIB-1" or "MIB-1 antibody" is one of Ki-67 monoclonal antibodies. The "MIB-1" or "MIB-1 antibody" is not particularly limited, but can be purchased from Dako Company or Immunotech Inc. The "MIB-1" or "MIB-1 antibody" recognizes and binds to an epitope consisting of PKEKAQALEDLAGFKELFQT (SEQ ID NO: 2) in Ki-67.

An "anti-Ki-67 antibody" refers to an antibody which recognizes and binds to Ki-67. Antibodies belonging to the MIB (registered trademark) family, such as MIB-1 as well as MIB-2, MIB-5, MIB-7, MIB-21 and MIB-24; and DAKO-PC, Ki-S5, A0047 and the like can be used as an "anti-Ki-67 antibody". Other antibodies which are sold in the market or used in clinical tests and which have the same properties as those of the above-mentioned antibodies can be also used as an "anti-Ki-67 antibody". An anti-Ki-67 antibody can be prepared by a known method with a Ki-67 antigen or a part thereof as an antigen. Preferably, an "anti-Ki-67 antibody" for use according to the present invention includes an antibody which recognizes the above-described epitope.

"Thrombin (factor IIa)" is an enzyme (serine protease) which is involved in clotting of blood (EC No: EC 3.4.21.5).

A "hydrolase which does not recognize or cleave the peptide of SEQ ID NO: 2" refers to a hydrolase which does not recognize or cleave the epitope of the MIB-1 antibody. Proteolytic enzymes having such properties can be known from, but not being limited to, a published database (Table 1). In addition, whether an enzyme has such properties can be determined by examining, with MIB-1, or another antibody which recognizes the same epitope, whether the enzyme cleaves the epitope.

For an antibody to infiltrate cells and/or for extraction of cell nuclei, preferably, an enzyme can recognize and cleave collagen, which is an extracellular matrix. Examples thereof include, but are not limited to, thrombin, Arg-C (clostripain) peptidase (EC 3.4.22.8) and proline endopeptidase (EC 3.4.21.26).

TABLE 1

| Proteolytic enzyme | Number of cleavages of target amino acid sequence | | |
|---|---|---|---|
| | Collagen alpha-1 (I) | Ki-67 | MIB epitope: SEQ ID NO: 2 |
| Proteinase K | 424 | 1392 | 13 |
| Thermolysin | 215 | 643 | 6 |
| Trypsin | 121 | 530 | 3 |
| Asp-N endopeptidase + N-terminal Glu | 141 | 448 | 4 |
| Pepsin (pH >2) | 111 | 420 | 8 |
| Chymotrypsin-low specificity (C-term to [FYWML], not before P) | 91 | 402 | 5 |
| Pepsin (pH1.3) | 87 | 397 | 8 |
| LysC | 57 | 374 | 3 |
| LysN | 57 | 374 | 3 |
| Glutamyl endopeptidase | 75 | 285 | 3 |
| Staphylococcal peptidase 1 | 73 | 239 | 3 |
| Arg-C proteinase/Clostripain | 71 | 198 | 0 |
| Asp-N endopeptidase | 66 | 163 | 1 |
| Chymotrypsin-hgh specificity (C-term to [FYW], not before P) | 38 | 96 | 2 |
| Proline-endopeptidase | 8 | 35 | 0 |
| dispase | 0 | 15 | 1 |
| Thrombin | 3 | 3 | 0 |

Collagen alpha1 (I): UniprotKB-P02452 (CO1A1_HUMAN)
Ki-67: SEQ ID NO: 1

Enzymes which hydrolyze components in extracellular matrixes other than proteins, such as hyaluronidase, are also preferable for the purpose of the present invention. Hyaluronidase (EC 3.2.1.35) is a hydrolase which breaks the β-1-4 bond of hyaluronic acid, and hyaluronidase does not cleave the peptide of SEQ ID NO: 2. This property of hyaluronidase accelerates infiltration of an antibody into cells. Examples of such enzymes having similar properties include hyaluronidase, glycosidase (EC 3.2.1) and N-glycanase (EC 3.5.1.52), with hyaluronidase being preferable.

In addition, while the above-mentioned proteolytic enzymes which do not recognize or cleave the peptide of SEQ ID NO: 2 are similar to hyaluronidase in that none of the enzymes cleave the peptide of SEQ ID NO: 2, but these enzymes are entirely different from each other in action mechanisms. A combination of both types of enzymes is therefore expected to further enhance antigen activation. In particular, a combination of thrombin and hyaluronidase is preferable.

The "activation of an antigen with an enzyme" is a process of cleaving an antigen or an extracellular matrix with an enzymatic treatment to enhance reactivity with an antibody. The process can be carried out by immersing a sample in a reagent obtained by dissolving an enzyme in a pH-adjusted buffer solution. The solution may be heated at a temperature suitable for the enzymatic reaction, and the reaction can be stopped after a predetermined time passes. To stop the reaction, removal of the reagent, change in a temperature, addition of a chelator or the like can be applied.

The "staining with an antibody" may be performed by directly binding a label of a fluorescent compound, an enzyme, a chemiluminescent substance or the like to each antibody, and binding the labeled antibody to an antigen (direct method); or providing an unlabeled primary antibody which binds to an antigen, and a secondary antibody which can specifically bind to the primary antibody and to which the label is bound, thereby labeling indirectly (indirect method).

A "fluorescent compound" is not particularly limited, but examples thereof include fluorescent substances such as cyanine-based pigments such as Cy3, fluorescein isothiocyanate (FITC), allophycocyanin and rhodamine. Preferably, antibodies (or secondary antibodies) can be labeled with fluorescent substance which emit light with different fluorescence wavelengths (for example, fluorescent substances of Alexa Fluor (registered trademark) series).

A "labeling enzyme" is not particularly limited, but examples thereof include alkali phosphatase and horseradish peroxidase.

A "chemiluminescent substance" is not particularly limited, but examples thereof include luminol, AMPPD (registered trademark), CSPD (registered trademark) and CDP-Star (registered trademark).

In one embodiment, when a population of cells in a tissue section may have not only Ki-67 but also other antigens to be detected/quantitatively determined: (1) in a single (FFPE) tissue section, respective ligands (for example, an anti-cytokeratin antibody, an anti-ER antibody, an anti-PgR antibody, a nucleic acid which hybridizes with the HER2 gene, or a secondary antibody or a nucleic acid which binds to any of the above-mentioned antibodies or nucleic acids) may be labeled with labels which enables the ligands to be discriminated from each other such as fluorescent coloring substances with different fluorescence wavelengths, thereby performing detection/quantitative determination; or (2) a plurality of (FFPE) tissue sections, which are supposed to be homogeneous, may be prepared from the same tissue block, followed by staining the sections (for example, by immunofluorescent staining or FISH) for each target substance to perform detection/quantitative determination.

The term "specifically staining cell nuclei" means that labeling is performed with a compound which specifically stains cell nuclei in fixed cells. Such a compound is not limited, but nucleic acid-staining compounds with cell-impermeability are preferable. Examples thereof include fluorescent coloring substances such as DAPI and propidium iodide (PI).

Fluorescent-stained cells or cell nuclei can be counted by cytometry. The cytometry is a cell measurement method in which a large number of cells (several thousand to several million cells) can be quantitatively measured one by one in a short time (several seconds to several minutes). The cytometry includes flow cytometry in which suspended cells are guided to a sensing zone one by one by a sheath flow, and scattered light, fluorescence and the like are measured instantly; and imaging cytometry in which a population of cells or the like deposited on a multi-well plate or slide glass are laser-scanned to acquire a fluorescence image, scattered light, transmitted light image or the like, and information for each cell is extracted by cell image processing.

The "step of extracting cell nuclei" means that cell nuclei are extracted from fixed cells (tissues) with the structures of the cell nuclei being maintained. The step can be carried out with means for crushing cells by generating shear stress on cells, and examples of the usable means include, but not being limited to, known means such as a water flow, a masher, a mortar, ultrasonication, a mesh, a French press, a homogenizer and glass beads.

Preferably, the present invention provides a method for isolating cell nuclei and enhancing signals by enabling staining without causing antigenicity to disappear from a FFPE tissue and without limiting antibodies used or detection methods, and the method comprises the following steps:
1) deparaffinization/hydrophilization of a FFPE section;
2) antigen retrieval with heat treatment;
3) antigen activation with an enzyme; and
4) extraction of cell nuclei by crushing the tissue and cells.

According to the present invention, a FFPE tissue may be sliced at a thickness of 60 μm or less to appropriately detect a marker along with efficiently performing the pretreatment step. It is recommended that a tissue be sliced at a thickness of 20 μm, but the present invention is not limited thereto. The number of the sections can be 2 or more depending on the size of a specimen, and the number of isolated cell nuclei necessary for subsequent examination.

The term "embedding" means that a piece of tissue (mass) is impregnated with an "embedding agent" so as to impart a constant and uniform hardness to the piece of tissue (mass), to fill hollow parts in the tissue to impart such strength as to prevent peeling during slicing, and to enhance preservability. An "embedding agent" is not particularly limited, but examples thereof include paraffin, paraffin derivatives, celloidin, carbowax, agarose, non-heparin-treated serum, collagen, cellulose derivatives, chitin derivatives, chitosan derivatives and mixtures thereof.

The term "de-embedding/hydrophilization" as used herein means that an embedding agent (e.g., paraffin) used for embedding is removed, and an organic solvent used for the removal is replaced by an aqueous solvent. An embedding agent can be removed by immersing a section in an organic solvent, typically xylene, and the section can be then impregnated with ethanol solutions with such different concentrations as to generate a concentration gradient in a descending order to replace the organic solvent. Examples of the ethanol concentration gradient include, but not being limited to, 100%→95%→90%→70%→50%.

The term "antigen retrieval with heat treatment" as used herein means a step of removing a mask which covers an epitope with heat treatment wherein the mask may be generated by formation of crosslinks during fixation. The heat treatment can be performed with an antigen retrieval agent for the heat treatment containing a citric acid buffer solution, a surfactant, a chelating agent, a reducing agent and the like. The retrieval agent is not particularly limited, but examples thereof include Histo VT One (nacalai tesque), Antigen Activation Solution pH 9 (Nichirei Bioscience Inc.) and ImmunoSaver (Nisshin EM Co., Ltd.) which are sold in the market.

The "crushing with a water flow" means that cells and tissues are crushed with a shear force from a water flow. Cells and tissues can be crushed with a water flow generated, for example, by rotating a blade at 10,000 rpm per 1 minute in an ice-cooled environment, for example, with a water flow shear apparatus (RP-10) from Sysmex Corporation.

The "crushing with ultrasonication" means that cells and tissues are crushed with a shear force caused by ultrasonication. Cells and tissues can be crushed, for example, by exposing the cells and tissues to an ultrasonication at an output intensity of 20% for 30 seconds with an ultrasonic crushing apparatus (VCX130PB) from SONICS & MATERIALS.

The step of crushing with ultrasonication is useful to preferentially crush lymphocytes over other blood cells, and also useful for crushing not only the cell walls of lymphocytes but also the nuclei of lymphocytes. Therefore, the step of crushing with ultrasonication is preferable when it is necessary to crush lymphocytes preferentially because existence of lymphocytes hinders analysis of other cells.

In order to isolate cell nuclei according to the present invention, two or more of the above-described methods may be combined, and crushing with a combination of water flow and an ultrasonication is preferable.

In the step of extracting cell nuclei, tissues or cells may be immersed or dispersed in an ordinary buffer solution, of which examples include a tris(hydroxymethyl)aminomethane buffer solution, a phosphate buffer solution, a carbonate buffer solution, a glycine buffer solution, a acetate buffer solution, a tartrate buffer solution, a citrate buffer solution, a triethanol amine buffer solution, a borate buffer solution, a Good buffer solution and the like. A surfactant has an action to accelerate isolation of cell nuclei, and it is therefore preferable to extract cell nuclei with a buffer solution containing a surfactant. The surfactant is not particularly limited as long as it does not affect cell nuclei, and examples thereof include anionic surfactants (carboxylic acid type, sulfonic acid type, sulfuric acid ester type, phosphoric acid ester type and the like), cationic surfactants (quaternary ammonium salt type, alkylamine salt type, pyridine ring-containing type and the like), ampholytic surfactants (betaine type, sulfobetaine type, amine oxide type, alkylimidazole type, amino acid type and the like), and nonionic surfactants (ester type, ether type, ester ether type, alkanolamide type, alkyl glycoside type and the like). The surfactant may be preferably a nonionic surfactant, which includes t-Octylphenoxypolyethoxyethanol (Triton™ X-100), Polyoxyethylene (40) isooctylphenyl ether (Triton™ X-405), Nonyl phenoxypolyethoxylethanol (NP-40), polyethoxylate lauryl ether (Brij® 35), polyethylene glycol hexadecyl ether (Brij®58), polyethylene glycol sorbitan monolaurate (Tween® 20), polyethylene glycol sorbitan monooleate (Tween® 80), PEG-25 Phytostanol (BPSH-25), Octyl Glucoside and Octylthio Glucoside.

Malignant tumors are tumors that infiltrate or metastasize to surrounding tissues, among cell populations (including benign tumors and malignant tumors) that proliferate in an autonomous and uncontrollable manner due to genetic mutation. In pathology, the term "malignant tumor" is classified into:
1) carcinoma: malignant tumor derived from epithelial tissue,
2) sarcoma: malignant tumor derived from non-epithelial tissue, and
3) others: leukemia etc.

As used herein, the "cancer" means a carcinoma. The carcinoma is not particularly limited, but examples thereof include head and neck cancers (upper jaw cancer, (upper, middle and lower) throat cancers, larynx cancer, tongue cancer and thyroid cancer), thoracic cancers (breast cancer, lung cancers (non-small cell lung cancer and small cell lung cancer)), digestive organ cancers (esophagus cancer, stomach cancer, duodenal cancer, bowel cancers (colon cancer and rectal cancer), liver cancers (liver cell cancer and bile duct cell cancer), gallbladder cancer, bile duct cancer, pancreas cancer, anus cancer, urinary organ cancers (kidney cancer, ureter cancer, bladder cancer, prostate cancer, penis cancer and testicle (testis) cancer), genital cancers (uterus cancers (uterine cervical cancer and uterine body cancer), ovary cancer, vulva cancer and vaginal cancer), skin cancers (basal cell cancer and squamous cell cancer), and the like.

Ki-67 can be used alone or in combination with another marker for assisting diagnosis of cancer or assisting prognosis of a cancer treatment.

For example, as an epithelial cell marker to be used for discriminating a carcinoma from a sarcoma, cytokeratin can be used. The cytokeratin is a principal skeletal protein of epithelial cells, and about 20 to 30 subtypes (molecular weight: 40 to 68 KDa) have been reported. For detecting cytokeratin as an epithelial cell marker, an antibody (a polyclonal or monoclonal antibody) which recognizes a wide range of known subtypes may be used, or a cocktail containing a plurality of known antibodies which specifically bind to respective subtypes may be used.

Estrogen receptor (ER) is one of molecules belonging to the steroid receptor superfamily and is also called a follicle hormone receptor. ER has two isoforms, which are called ERα and ERβ, respectively. These isoforms are produced from independent genes (ESR1 and ESR2). ESR1 exists in 6q25.1, and ESR2 exists in 14q21-22.

Progesterone receptor (PR or PgR) is an intranuclear protein belonging to subfamily 3, group C, of the intranuclear receptor superfamily. The receptor is encoded by a single PgR gene existing in 11q22, and known to have two isoforms having different molecular weights.

Hormone receptor-positive breast cancers account for about two-thirds of primary breast cancers, and the number of Japanese women having ER-positive breast cancer has been found to tend to increase. Expression of PgR is induced by an estrogen-ER complex, and existence or non-existence PgR gives an indication of whether estrogen and ER normally function. Currently, expression of these hormone receptors is detected by an immunohistochemical method with pathological tissue specimens.

HER2 is a glycoprotein with about 185 kDa which exists on cell surfaces. HER2 is a receptor-type tyrosine kinase, has a structure similar to that of an epidermal growth factor receptor (EGFR, also referred to as ERBB1), and is also called EGFR2, ERBB2, CD340 or NEU. The gene which encodes HER2 protein is HER2/neu, erbB-2, and exists in the long arm of chromosome 17. HER2 is a protein belonging to the human epidermal growth factor receptor (HER/EGFR/ERBB) family (EGFR family).

HER2 protein is involved in control of cell proliferation, cell differentiation and the like in normal cells, and if amplification of the HER2 gene or genetic mutation occurs for some reason, cell proliferation and cell differentiation cannot be controlled, and thus the cells become malignant. HER2 gene is also a cancer gene, and amplification of the gene is observed in many types of cancers.

Samples obtained in the step of antigen activation with an enzyme and the step of extracting cell nuclei can be also used for analysis of the above-mentioned markers which may be combined with Ki-67 to assist diagnosis. In particular, an enzymatic treatment with a combination of thrombin and hyaluronidase is preferable when these markers are also analyzed. Of course, HER2 gene may be detected with a nucleic acid extracted by a known method after isolation of nuclei.

A "subject" may be a mammal, which may be a "human" or a "non-human mammal".

A "tissue section" refers to a section of an isolated tissue from a human or a non-human animal. The tissue section may be a "tissue section" collected by biopsy. The "tissue section" may be, for example, preserved in a frozen state after the isolation.

The term "biopsy" means that part of a pathological tissue is collected with a surgical knife or a needle to be observed with a microscope or the like for diagnosis. In the case of breast cancer, a tissue is collected from the breast of a subject by "excision biopsy" (removal of an entire lump of a tissue); "incision biopsy" (partial removal); "core biopsy" (removal of part of a tissue with a large-bore needle); or "fine-needle puncture aspiration (FNA) biopsy" (removal of part of a tissue or a body fluid with a fine needle).

An "antigen activator for enzymatic treatment" and an "antigen retrieval agent for heat treatment" may be dissolved in a solution, or in a dry solid state. In case that one or both of them are in a solid state, a "kit" may contain a "solvent" for dissolving these solid ingredients.

An "antigen activator used for a sample which is to be subjected to Ki-67 detection by immunostaining" refers to an enzymatic activator used for a sample, generally a population of fixed cells or a fixed tissue, in which cells or cell nuclei are detected with an anti-Ki-67 antibody.

"Prognosis of a cancer treatment" means that in the case that chemotherapy (anticancer drug treatment), endocrine therapy, a surgical operation (removal of a tumor), radiation therapy or the like is to be applied to a subject, an effect of the therapy is confirmed or predicted.

A "kit for detecting Ki-67-positive cells in a population of fixed cells" comprises a hydrolase which does not recognize or cleave the peptide of SEQ ID NO: 2; and an anti-Ki-67 antibody. The hydrolase is preferably at least one selected from the group consisting of thrombin, Arg-C (clostripain) peptidase, proline endopeptidase and hyaluronidase, and more preferably thrombin and/or hyaluronidase. The anti-Ki-67 antibody is preferably at least one selected from the group consisting of MIB-1, DAKO-PC, Ki-S5 and A-0047. The anti-Ki-67 antibody may be directly labeled with a fluorescent coloring substance, an enzyme, a chemiluminescent substance, a radioactive element or the like; or the kit may comprise a secondary antibody which binds to an anti-Ki-67 antibody, the secondary antibody being labeled with a fluorescent coloring substance, an enzyme, a chemiluminescent substance, a radioactive element or the like. The kit may comprise a ligand (for example, an antibody or a probe) for detecting another marker which is used in combination with Ki-67 to assist diagnosis of cancer or prognosis of a cancer treatment. Examples of the ligand include an anti-cytokeratin antibody, an anti-ER antibody, an anti-PgR antibody or a probe which hybridizes with the HER2 gene (typically under strict conditions) (these or secondary ligands thereof (antibodies or nucleic acids) may be labeled); and compounds for staining nucleic acids (for example, DAPI and propridium iodide (PI)).

The kit may further comprise a buffer solution for immersing or dispersing a tissue or cells subjected to the "step of extracting cell nuclei". Preferably the buffer solution may comprises a surfactant. The surfactant may be preferably CHAPS, NP-40, or Triton™ X-100, and more preferably NP-40 or Triton™ X-100. The present invention therefore provides a kit for extracting cell nuclei from cells (typically fixed cells) with shear stress generated by a water flow, ultrasonication or the like, the kit comprising a buffer solution for dispersing cells containing a surfactant.

A "cutoff value" (dividing point or value for discriminating disease states) refers to a numerical value for determining whether the examination result is interpreted as positive or negative. In the case of Ki-67, a value between 14 and 20% is currently recommended for discriminating between the luminal A(-like) type and the luminal B (-like) type.

An "anticancer drug" refers to a drug for treating or preventing cancer. The anticancer drug is not limited to, but classified into molecular-targeted drugs, alkylating agents, metabolic antagonists, vegetable alkaloids, anticancer antibiotic substances, platinum-containing preparations, hormonal agents, biological response modifiers and the like.

A "endocrine therapy" is a treatment for impeding the action of a female hormone (estrogen) which accelerates proliferation of hormone-dependent breast cancer. The treatment comprises, but not being limited to, administering a hormonal agent such as an antiestrogen, an Lh-RH agonist preparation, an aromatase inhibitor or a progesterone preparation.

A "chemotherapy" means that a cancer is treated with a chemical substance which exerts an anticancer effect. The therapy comprises, but not being limited to, administrating solely or in combination with one or more of an anthracycline-based anticancer drug (daunorubicin (daunomycin), doxorubicin (adriamycin), epirubicin, idarubicin or the like) which is a DNA synthesis and replication inhibitor; a taxane-based anticancer drug (paclitaxel (taxol), docetaxel (taxotere) or the like) which is a cell proliferation inhibitor; a platinum-containing preparation (cisplatin, oxaliplatin or the like) which prevents DNA replication; and the like. Preferably, the therapy may comprises administrating a combination of an anthracycline-based anticancer drug and a taxane-based anticancer drug. As used herein, administration of a "hormonal agent" belongs to the "endocrine therapy".

EXAMPLES

The present invention will be described in further detail with reference to Examples, Comparative Examples and Reference Examples below, but these examples should not be construed as limiting the present invention.

Reference Example 1

Observation of Isolation of Cell Nuclei by Water Flow Shear
1. Materials and Method
A FFPE tissue section of a breast cancer tissue was deparaffinized/hydrophilized, subjected to antigen retrieval with heat treatment, and dispersed by a water flow shear apparatus. The recovered product was then immunofluorescently stained, and observed with a microscope.

1-1. FFPE Tissue Block
A FFPE tissue block of a breast cancer tissue was purchased from ProteoGenex, Inc.

1-2. Preparation of FFPE Section
A FFPE section with a thickness of 20 μm was prepared by slicing a FFPE tissue block with a sliding microtome manufactured by Thermo Fisher Scientific.

1-3. Deparaffinization/Hydrophilization
A sufficient amount of xylene was added to the FFPE section, the section was placed still for 10 minutes, and xylene was then removed. These steps were carried out again to completely remove paraffin. Subsequently, the section was immersed in 100% ethanol, 95% ethanol, 70% ethanol, 50% ethanol and deionized water in this order for 3 minutes each to hydrophilize the section.

1-4. Antigen Retrieval with Heat Treatment
Histo VT One (manufactured by nacalai tesque) was diluted 10 times with pure water and added to the section, and it was heated on a heat block at 98° C. for 20 minutes. After the heating, the section was placed still at room temperature for 20 minutes, followed by removing the antigen activation liquid.

1-6. Crushing with Water Flow
The activated tissue was crushed in 1 mL of TBS at 10,000 rpm for 1 minute in an ice-cooled environment using a water flow shear apparatus (RP-10) from Sysmex Corporation.

1-7. Immunofluorescent Staining
4% BSA/TBS containing 10% normal goat serum (Wako) was added to a microtube containing the crushed product obtained by crushing the tissue with a water flow, and the mixture was placed still at room temperature for 30 minutes and subjected to blocking treatment. Immunofluorescent staining was performed with a pan-cytokeratin antibody (Abcam, rabbit polyclonal antibody: Anti-wide spectrum Cytokeratin antibody (AB9377-500)) as a primary antibody, and Goat anti-Rabbit Secondary Antibody Alexa 488 from Abcam PLC as a secondary antibody. The primary antibody reaction time was 50 minutes, the secondary antibody reaction time was 30 minutes, and DAPI Solution (Wako) was added to stain cell nuclei at the time when the secondary antibody reaction time elapsed. The reaction temperature was set to room temperature throughout the reactions, and the reactions were carried out under a light-shielding condition after addition of the secondary antibody. 0.5% BSA/TBS was used as an antibody diluting liquid, and washing with 0.5% BSA/TBS was carried out once between the steps. After the secondary antibody reaction, 5 μL of a DAPI solution (Wako) was placed on a slide glass, and the sample was placed thereon. Thereafter, a cover glass was put on the sample, the sample was placed still for 5 minutes, the cover glass was vertically pressed from above, and the gaps around the cover glass were sealed with manicure. The sample was stored at 4° C. while being shielded from light until the time of observation.

1-8. Fluorescence Microscope
For microscopic observation, EVOS All-In-One Microscope, a fluorescence microscope (Thermo Fisher Scientific) was used. At the time of observation, DAPI Light Cube (Ex 357 nm, Em 447 nm) and GFP Light Cube (Ex 470 nm/Em 510 nm) were used. An eye lens with a magnification of 10 times and an objective lens with a magnification of 40 times were used.

2. Results

FIG. 1 shows a cell nucleus observed by a fluorescence microscope. As shown in the left picture, nucleic acid exists in a circular form, and as shown in the right picture cytokeratin exists around the nucleic acid. These show that the cell nucleus was recovered as a single cell nucleus without being aggregated while the cell nucleus and the skeleton were not damaged thereby maintaining a circular shape.

Reference Example 2

Examination of Signals Derived from Cytokeratin and Ki-67 in Formalin-Fixed Breast Cancer Cells 1. Materials and Method Formalin-fixed breast cancer cells were subjected to antigen retrieval with heat treatment and immunofluorescently stained, and signals from cytokeratin and Ki-67 were examined by a flow cytometer.

1-1. Cells

Three breast cancer cell lines: T47D, MDA-MB-231 (described as MB231 or 231 in the figures) and SKBr3 (described as SKBR in the figures) were acquired from ATCC (American Type Culture Collection).

1-2. Cell Culture and Formalin Fixation

The T47D cell line was cultured in RPMI-1640 medium, the MDA-MB-231 cell line was cultured in Leibovitz's L-15 medium, SKBr3 cells were cultured in McCoy's 5A medium. These mediums are supplemented with 10% fetal bovine serum (FBS). After sufficient proliferation of the cells, a culture solution was drawn in, and the cells were washed with PBS, followed by adding TrypLE Express (Thermo Fisher Scientific). The cells were recovered, then centrifuged, and washed with PBS. Further, the cells were sufficiently suspended in PBS, then dispensed to $1 \times 10^6$ and centrifuged, PBS was removed, a 10% formalin neutral buffer solution (Wako Pure Chemical Industries, Ltd.) was added to the cells, and the cells were then fixed at 4° C. for 24 hours. Before the cells were used, the formalin solution was removed, and the cells were washed with PBS.

1-4. Antigen Retrieval with Heat Treatment

The same treatment as in Reference Example 1 was carried out.

1-7. Immunofluorescent Staining

4% BSA/TBS containing 10% normal goat serum (Wako) was added to a microtube containing the cells after the antigen retrieval with heat treatment, and the mixture was placed still at room temperature for 30 minutes, and subjected to blocking treatment. For immunofluorescent staining, double staining was performed with a mixed liquid of a mouse antibody and a rabbit antibody. A Ki-67 antibody (Dako, clone: MIB-1, mouse monoclonal antibody) and a pan-cytokeratin antibody (Abcam, rabbit polyclonal antibody (AB9377-500)) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies. The primary antibody reaction time was 50 minutes, the secondary antibody reaction time was 40 minutes, and DAPI Solution (Wako) was added to stain cell nuclei 20 minutes after addition of the secondary antibody. The reaction temperature was set to room temperature throughout the reactions, and the reactions were carried out under a light-shielding condition after addition of the secondary antibody. 0.5% BSA/TBS was used as an antibody diluting liquid, and washing with 0.5% BSA/TBS was carried out once between the steps. As a negative control (isotype control), antibodies identical in type and concentration to respective primary antibodies were used instead of the primary antibodies. A mouse IgG antibody from Dako Company was used as a negative control for Ki-67, and a rabbit IgG antibody from Cell Signaling Technology, Inc. was used as a negative control for cytokeratin.

1-8. Flow Cytometer Measurement

The cells were caused to pass through a 35 μm filter (380 meshes) (for flow cytometer) for Falcon (registered trademark) Cell Strainer 5 mL Tube, and transferred into a specified vessel, and measured by a flow cytometer (Sysmex: Space). The measurement was performed in accordance with the equipment manual.

1-9. Calculation of Cytokeratin- and Ki-67-Positive Ratios

Figure 2:
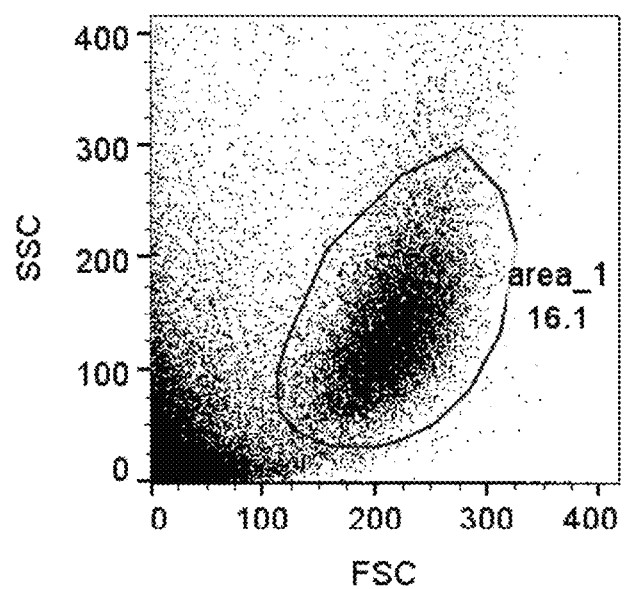
FIG. 2 shows a scattergram with the forward scatter in the horizontal axis and the side scatter in the vertical axis wherein the scattergram was obtained through a process in which formalin-fixed tumor cell lines (MB231, T47D and SKBR) were subjected to antigen retrieval with heat treatment, immuno-fluorescently stained and then measured by a flow cytometer, and the obtained date was analyzed.
Figure 3:
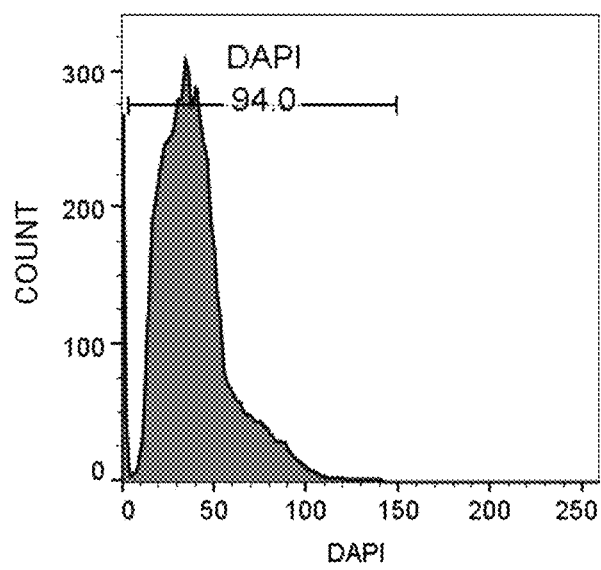
FIG. 3 shows a histogram with the fluorescence intensity of DAPI in horizontal axis and the number of cells (nuclei) in the vertical axis wherein the histogram was obtained through a process in which the area selected by the frame in FIG. 2 is gated as a group of cell nuclei, and the data of the gated fractions were analyzed.

For analysis of the obtained measurement data, software FlowJo v10 manufactured by FLOWJO LLC was used. The data was analyzed by the following procedure in accordance with the written instructions attached to the software. The principal area shown in FIG. 2 was selected on a scattergram which shows the forward scatter in the horizontal axis and the side scatter in the vertical axis. Next, the principal area was gated as cell nuclei to generate a histogram with the fluorescence intensity of DAPI in the horizontal axis and the number of cells (nuclei) in the vertical axis (FIG. 3). The cytokeratin- and Ki-67-positive ratios were calculated as ratios of the number of cytokeratin-positive nuclei and the number of Ki-67-positive nuclei with respect to the number of all cell nuclei. The threshold value of the positive nuclei was set to the 95 percentile value of the isotype control.

2. Results

Figure 4:
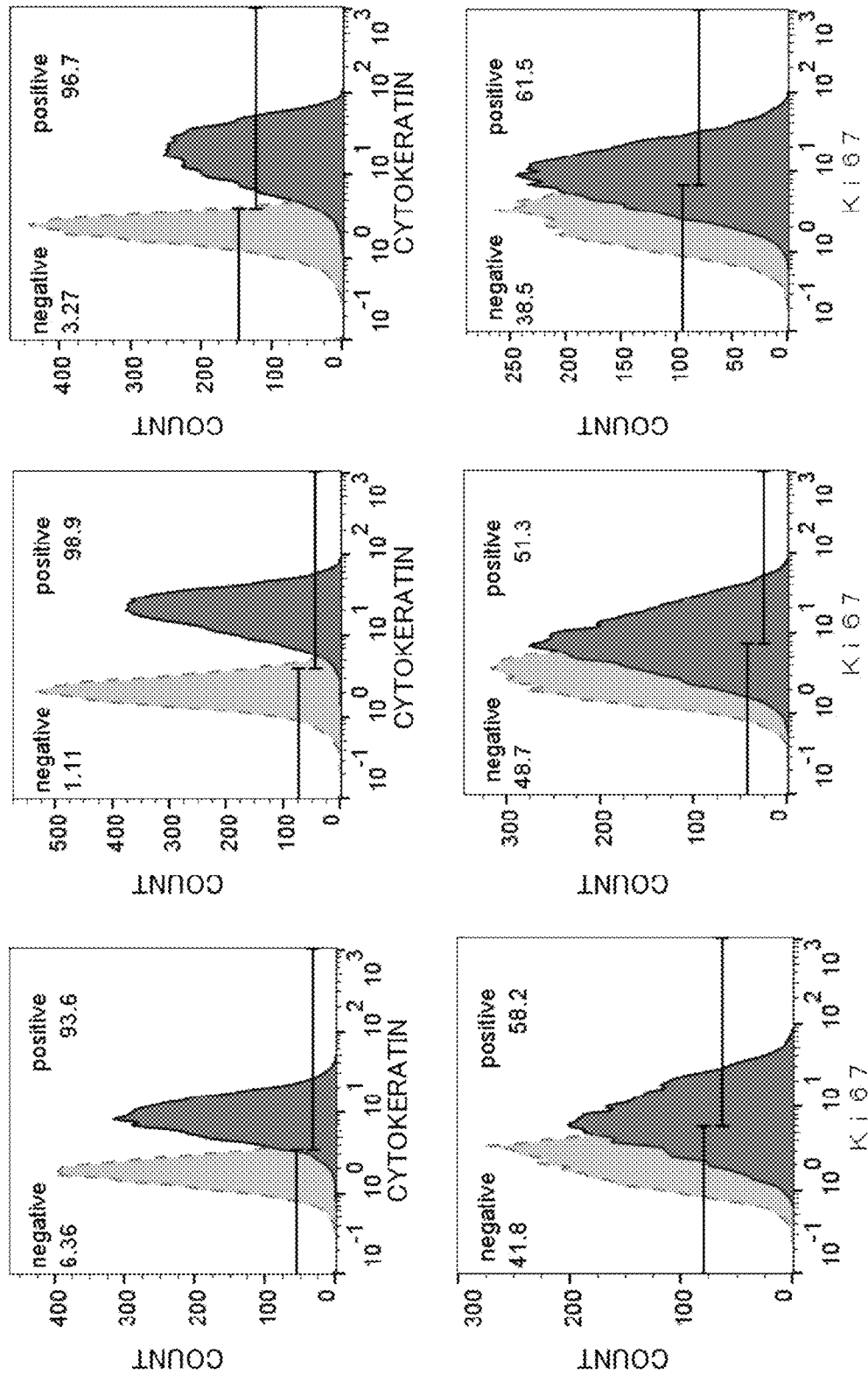
FIG. 4 shows histograms with the fluorescence intensity in the horizontal axis and the number of cells (nuclei) in the vertical axis wherein the histograms were obtained through a process in which formalin-fixed breast cancer cells were subjected to antigen retrieval with heat treatment, immuno-fluorescently stained with an anti-cytokeratin antibody and an anti-Ki-67 antibody or isotype control antibodies thereof and then measured by a flow cytometer, and the data of fractions gated as a group of cell nuclei were analyzed.

FIG. 4 shows charts obtained by overlaying histograms of fluorescence intensities detected with the anti-cytokeratin antibody and the anti-Ki-67 antibody (black solid lines) and histograms of the fluorescent intensities detected with the isotype control antibodies thereof (gray broken lines). For all the cell lines, the black line peaks showed higher fluorescence intensities as compared to the gray line peaks. Thus, it was confirmed that cytokeratin and K-67 existed in the formalin-fixed breast cancer cells.

Example 1

Enhancement of Ki-67 Signals in Formalin-Fixed Cells by Antigen Activation with Thrombin 1. Materials and Method With formalin-fixed breast cancer cells, signal intensities with and without thrombin treatment were compared.

1-1. Cells

The three breast cancer cell lines used in Reference Example 2 were used.

1-2. Cell Culture and Formalin Fixation

The same procedure as in Reference Example 2 was carried out.

1-4. Antigen Retrieval with Heat Treatment

The same treatment as in Reference Example 1 was carried out.

1-5. Antigen Activation with Enzyme

A thrombin reagent (25 mM Tris-HCl pH 7.4, 150 mM NaCl, 1000 KU/L thrombin, 10 mM $CaCl_2$)) was added to the cells after the antigen retrieval with heat treatment, and the cells were heated on a heat block at 37° C. for 20 minutes.

1-7. Immunofluorescent Staining

The same procedure as in Reference Example 2 was carried out. Here, a Ki-67 antibody (Dako, clone: MIB-1, mouse monoclonal antibody) was used as a primary antibody, and Goat anti-Mouse Secondary Antibody Alexa 647 from Thermo Fisher Scientific was used as a secondary antibody.

1-8. Flow Cytometer Measurement

The same procedure as in Reference Example 2 was carried out.

1-9. Calculation of Ki-67-Positive Ratio

The same procedure as in Reference Example 2 was carried out.

2. Results

Figure 5:
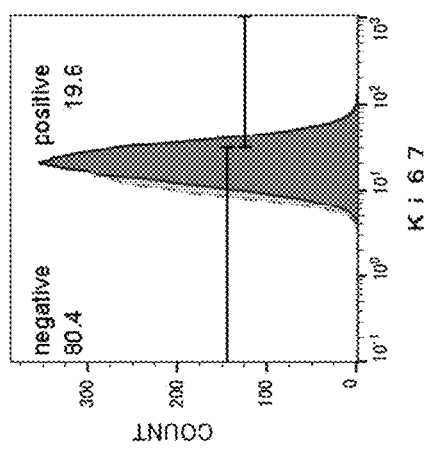
FIG. 5 shows histograms with the fluorescence intensity in the horizontal axis and the number of cells (nuclei) in the vertical axis wherein the histograms were obtained through a process in which formalin-fixed tumor cell lines (MB231, T47D and SKBR) were subjected to antigen retrieval with heat treatment, then were or were not subjected to antigen activation with thrombin, immuno-fluorescently stained with an anti-Ki-67 antibody or an isotype control antibody thereof and then measured by a flow cytometer, and the data of fractions gated as a group of cell nuclei were analyzed.
Figure 5:
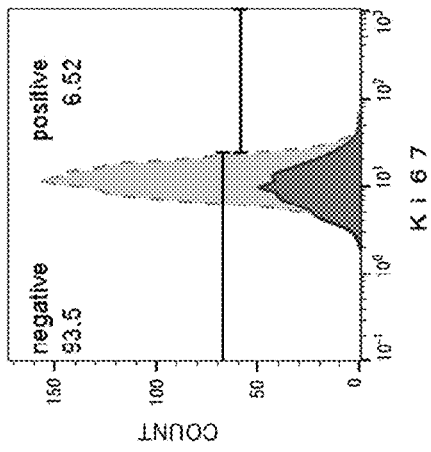
Figure 5:
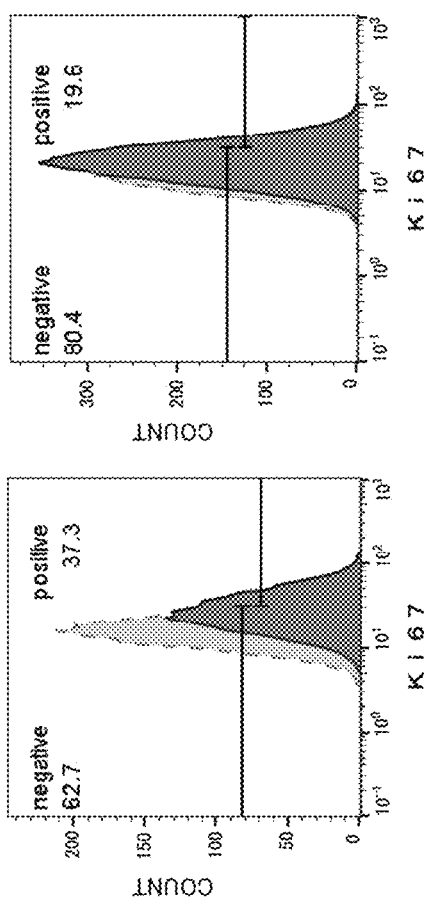
Figure 5:
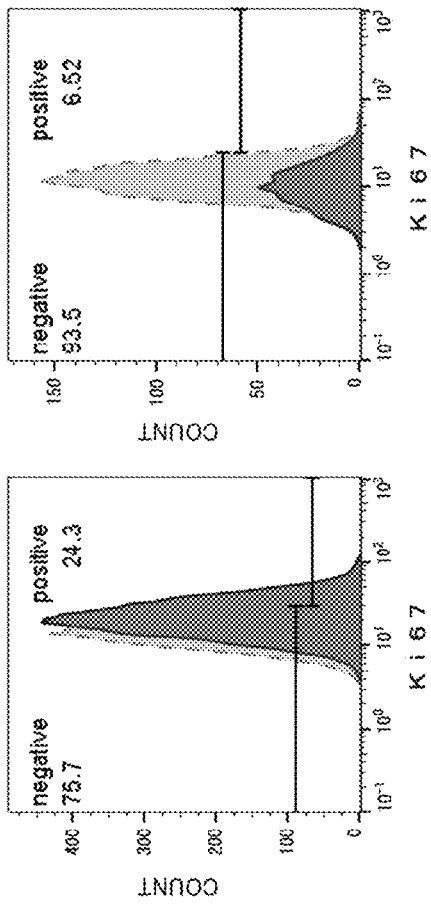
Figure 5:
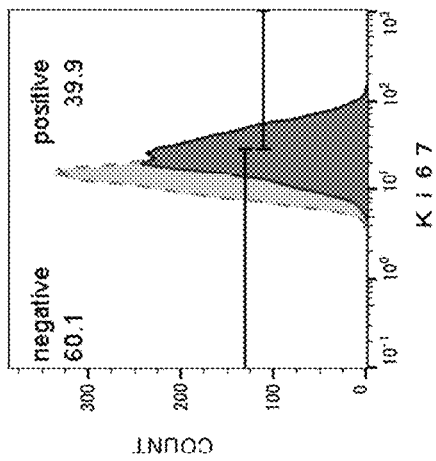
Figure 5:
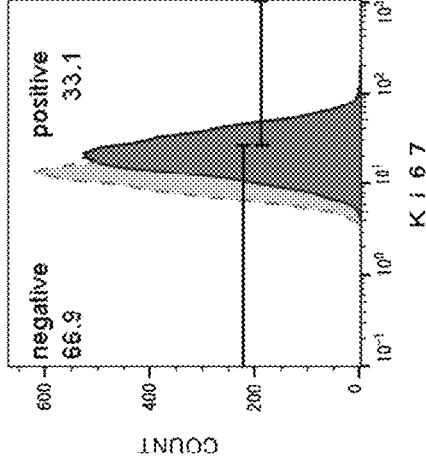
Figure 6:
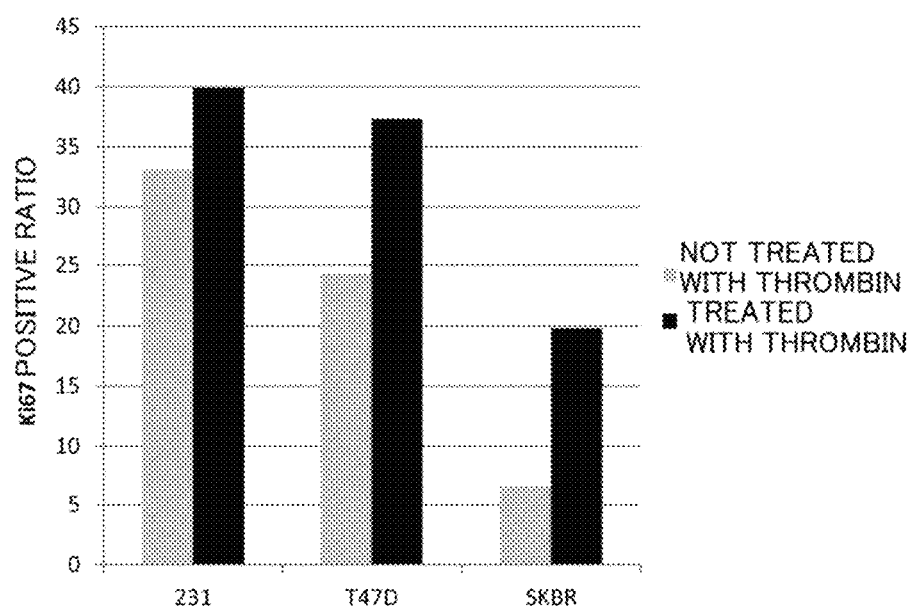
FIG. 6 is a graph showing a change in Ki-67-positive ratio in each tumor cell line depending on whether or not thrombin treatment is performed.

FIG. 5 shows charts obtained by overlaying the fluorescence intensities detected with the anti-Ki-67 antibody (black solid lines) and the isotype control antibody (gray broken like), and FIG. 6 and Table 2 shows changes in Ki-67-positive ratios. For all the cell lines, antigen activation with thrombin increased the fluorescence intensity, and also increased Ki-67-positive ratios.

TABLE 2

| | Thrombin treatment. | |
|---|---|---|
| | Done | Not done |
| T47D | 37.3 | 24.3 |
| MDA-MB-231 | 39.9 | 33.1 |
| SKBR | 19.8 | 6.52 |

Example 2

Enhancement of Ki-67 Signals in Formalin-Fixed Cells by Antigen Activation with Hyaluronidase 1. Materials and Method With formalin-fixed breast cancer cells, signal intensities with and without hyaluronidase treatment were compared.

1-1. Cells

The T47D cell line used in Reference Example 2 was used.

1-2. Cell Culture and Formalin Fixation

The same procedure as in Reference Example 2 was carried out.

1-4. Antigen Retrieval with Heat Treatment

The same treatment as in Reference Example 1 was carried out.

1-5. Antigen Activation with Enzyme

A hyaluronidase reagent (25 mM Tris-HCl pH 7.4, 150 mM NaCl, 4000-10000 KU/L Hyaluronidase I-S, 7500-30000 KU/L Hyaluronidase IV-S, 27 mM KCl) was added to the cells after the antigen retrieval with heat treatment, and the cells were heated on a heat block at 37° C. for 20 minutes.

1-7. Immunofluorescent Staining

The same procedure as in Reference Example 2 was carried out. Here, a Ki-67 antibody (Dako, clone: MIB-1, mouse monoclonal antibody) was used as a primary antibody, and Goat anti-Mouse Secondary Antibody Alexa 647 from Thermo Fisher Scientific was used as a secondary antibody.

1-8. Flow Cytometer Measurement

The same procedure as in Reference Example 2 was carried out.

1-9. Calculation of Ki-67-Positive Ratio

The same procedure as in Reference Example 2 was carried out.

2. Results

Figure 7:
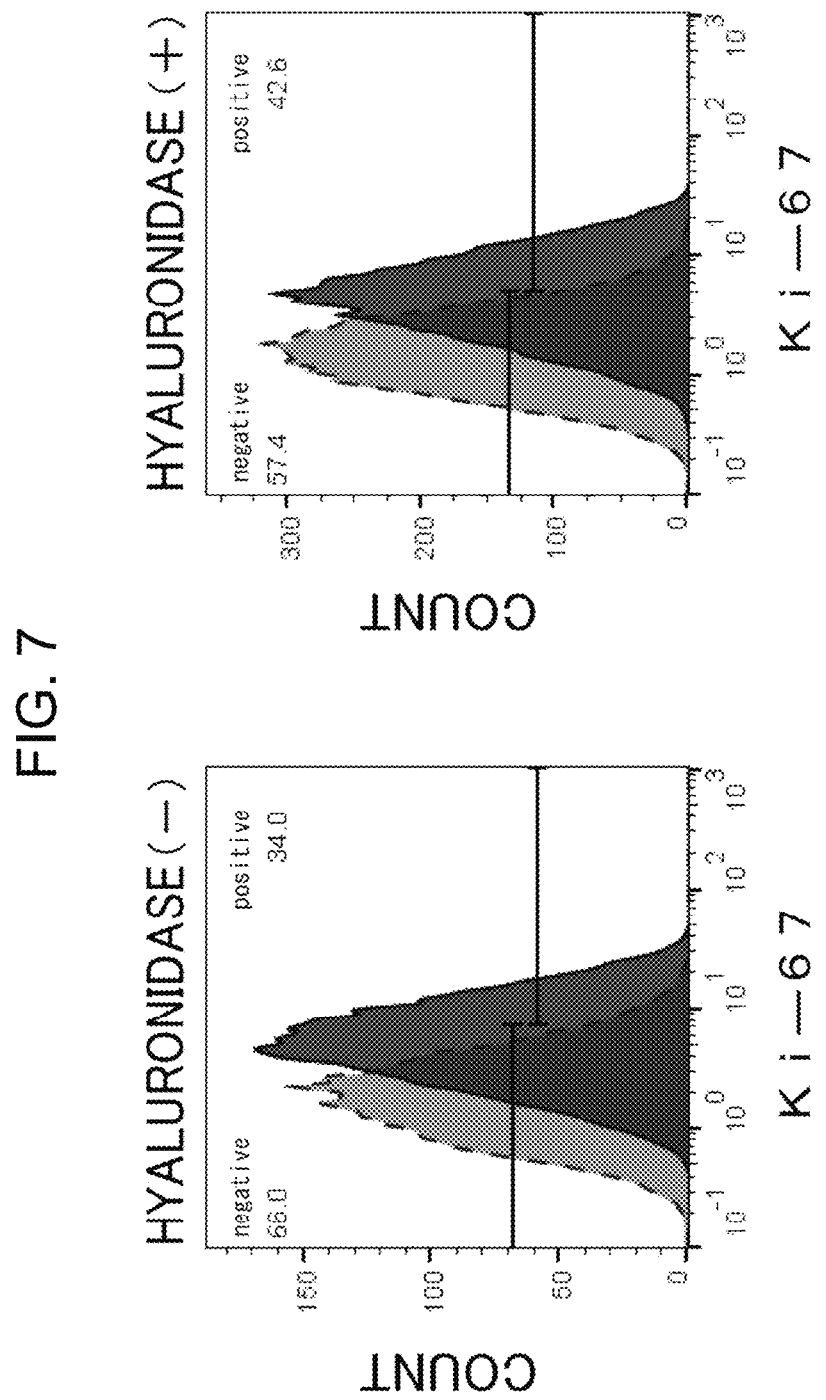
FIG. 7 shows histograms with the fluorescence intensity in the horizontal axis and the number of cells (nuclei) in the vertical axis wherein the histograms were obtained through a process in which a formalin-fixed T47D cell line was subjected to antigen retrieval with heat treatment, then was or was not treated with a hyaluronidase reagent, immuno-fluorescently stained with an anti-Ki-67 antibody or an isotype control antibody thereof and then measured by a flow cytometer, and the data of fractions gated as a group of cell nuclei were analyzed.

FIG. 7 shows charts obtained by overlaying the fluorescence intensities detected with the anti-Ki-67 antibody (black solid lines) and the isotype control antibody (gray broken like). The hyaluronidase treatment increased the fluorescence intensity, and also increased Ki-67-positive ratios.

Reference Example 3

Examination of Signals Derived from Cytokeratin and Ki-67 in FFPE Tissue Section 1. Materials and Method Signals from cytokeratin and Ki-67 in a FFPE tissue section of a breast cancer tissue were examined by a flow cytometer.

1-1. FFPE Tissue Block

The FFPE tissue block used in Reference Example 1 was used.

1-2. Preparation of FFPE Section

Two FFPE sections with a thickness of 20 μm were prepared by slicing a FFPE tissue block with a sliding microtome manufactured by Thermo Fisher Scientific, and were used for examination.

1-3. Deparaffinization/Hydrophilization

The same procedure as in Reference Example 1 was carried out.

1-4. Antigen Retrieval with Heat Treatment

The same procedure as in Reference Example 1 was carried out.

1-6. Crushing with Water Flow

The same procedure as in Reference Example 1 was carried out.

1-7. Immunofluorescent Staining

The same procedure as in Reference Example 2 was carried out.

1-8. Flow Cytometer Measurement

The same procedure as in Reference Example 2 was carried out.

1-9. Calculation of Cytokeratin- and Ki-67-Positive Ratios

For analysis of the obtained measurement data, software FlowJo v10 manufactured by FLOWJO LLC was used. The data were analyzed in the following procedure. First, in a chart with the fluorescence intensities of DAPI in the horizontal axis and the number of cells (nuclei) in the vertical axis, an area in which the fluorescence intensities in the horizontal axis are 5 to 150 was gated as cell nuclei. The cytokeratin- and Ki-67-positive ratios in the area were calculated as ratios of the number of cytokeratin-positive nuclei and the number of Ki-67-positive nuclei with respect to the number of all cell nuclei. The threshold value of the positive nuclei was set to the 95 percentile value of the isotype control.

2. Results

Figure 8:
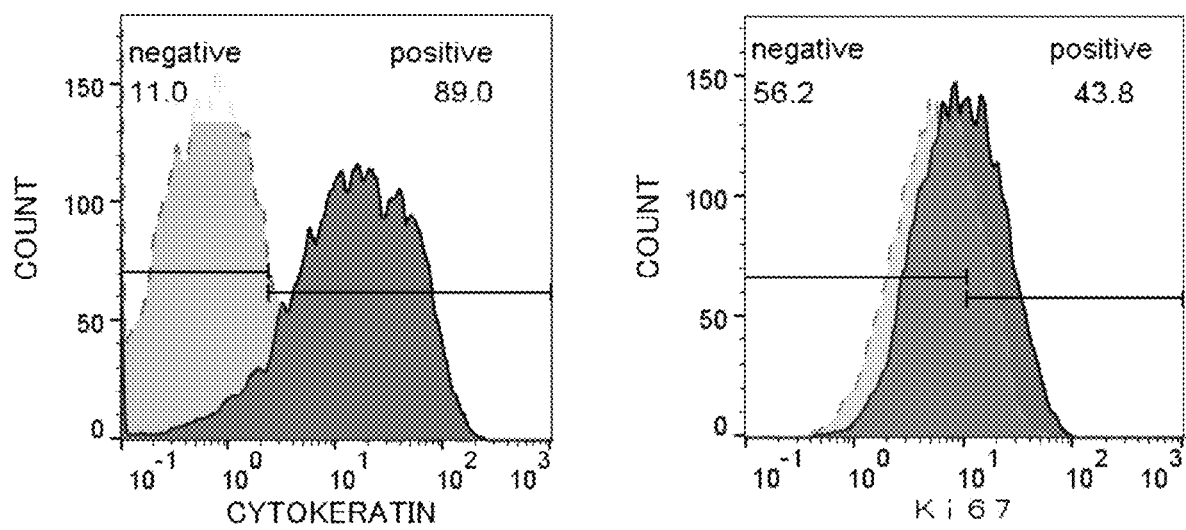
FIG. 8 shows histograms with the fluorescence intensity in the horizontal axis and the number of cells (nuclei) in the vertical axis wherein the histograms were obtained through a process in which a FFPE tissue section of a breast cancer tissue was deparaffinized/hydrophilized and subjected to antigen retrieval with heat treatment, the cells are crushed with a water flow, then immunofluorescently stained with an anti-cytokeratin antibody and an anti-Ki-67 antibody or isotype control antibodies thereof and then measured by a flow cytometer, and the data of fractions gated as a group of cell nuclei were analyzed.

FIG. 8 shows charts obtained by overlaying histograms of the fluorescence intensities detected with the anti-cytokeratin antibody and the anti-Ki-67 antibody (black solid lines) and histograms of the fluorescent intensities detected with the isotype control antibodies thereof (gray broken lines). The black line peaks showed higher fluorescence intensities as compared to the gray line peaks. Thus, it was confirmed that cytokeratin and K-67 were detected in a FFPE tissue section.

Example 3

Figure 9A:
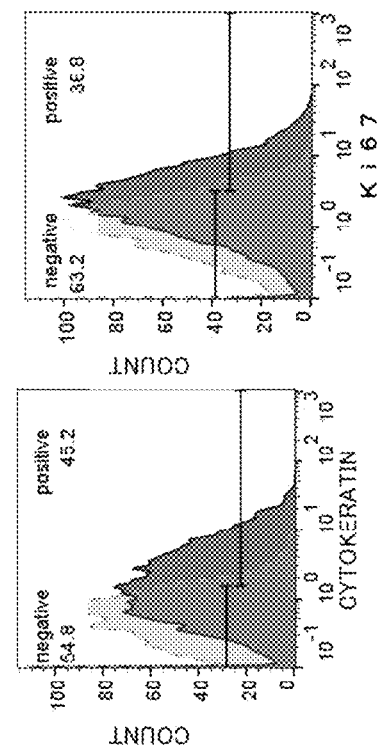
FIG. 9A shows histograms with the fluorescence intensity in the horizontal axis and the number of cells (nuclei) in the vertical axis wherein the histograms were obtained through a process in which a FFPE tissue section of a breast cancer tissue was deparaffinized/hydrophilized, subjected to antigen retrieval with heat treatment, and was or was not subjected to antigen activation with thrombin, the cells were crushed with a water flow, then immunofluorescently stained with an anti-cytokeratin antibody and an anti-Ki-67 antibody or isotype control antibodies thereof and then measured by a flow cytometer, and the data of fractions gated as a group of cell nuclei were analyzed. The histograms show that thrombin treatment enhanced cytokeratin and Ki-67 signals in the FFPE tissue section specimen.
Figure 9A:
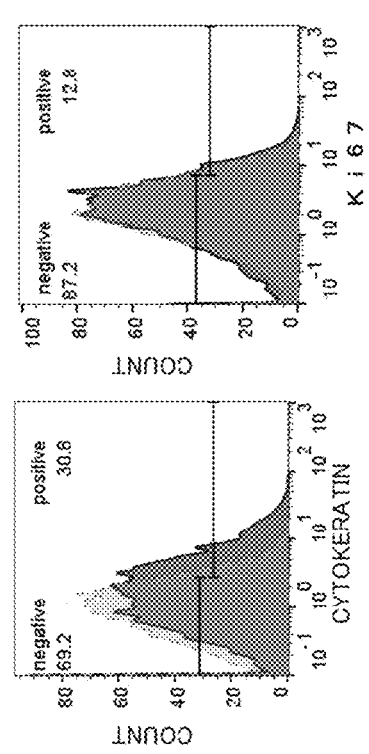
Figure 9B:
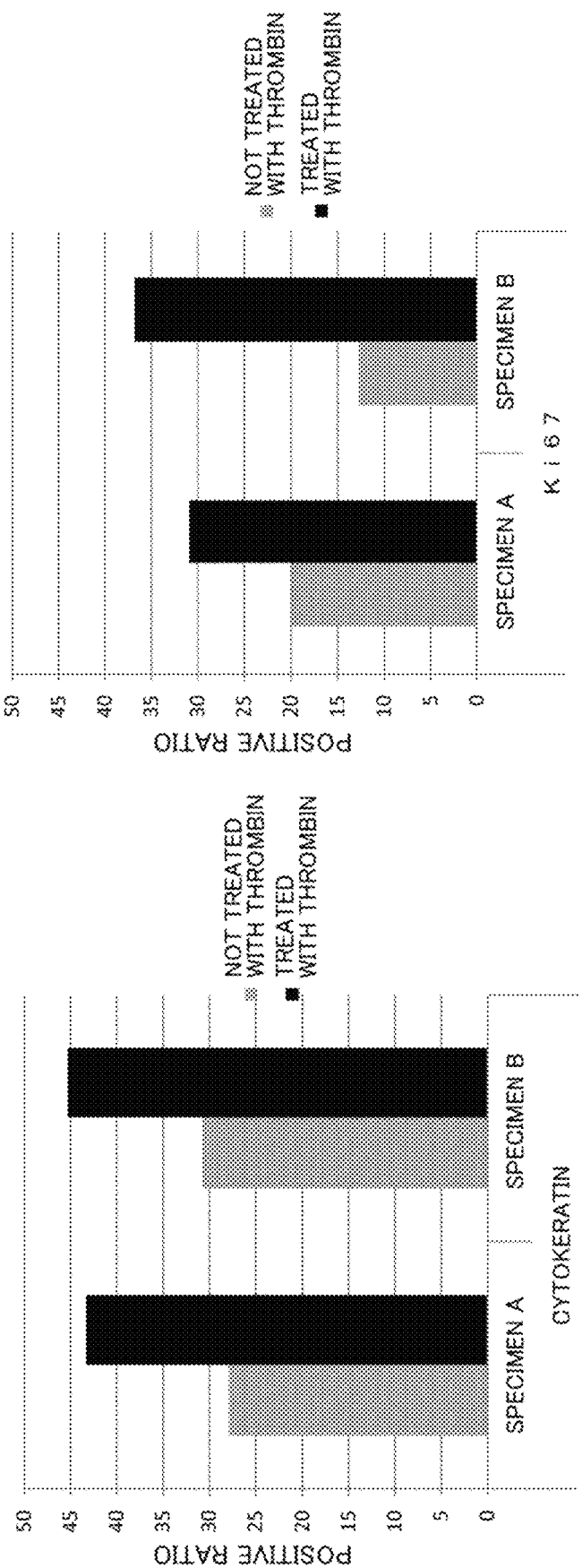
FIG. 9B shows graphs showing a change in cytokeratin- and Ki-67-positive ratios in the FFPE tissue section depending on whether or not thrombin treatment is performed.

Enhancement of Cytokeratin and Ki-67 Signals in FFPE Tissue Section by Antigen Activation with Thrombin
1. Materials and Method
    With a FFPE tissue section of a breast cancer tissue, signal intensities with and without thrombin treatment were compared.
1-1. FFPE Tissue Block
    Two FFPE tissue blocks were purchased from ProteoGenex, Inc., which were obtained from two patients with breast cancer and resulted in different Ki-67-positive ratios by a HC method.
1-2. Preparation of FFPE Section
    Two FFPE sections with a thickness of 20 µm were prepared by slicing a FFPE tissue block with a sliding microtome manufactured by Thermo Fisher Scientific, and were used for examination.
1-3. Deparaffinization/Hydrophilization
    The same procedure as in Reference Example 1 was carried out.
1-4. Antigen Retrieval with Heat Treatment
    The same procedure as in Reference Example 1 was carried out.
1-5. Antigen Activation with Enzyme
    The same procedure as in Example 1 was carried out.
1-6. Crushing with Water Flow
    The same procedure as in Reference Example 1 was carried out.
1-7. Immunofluorescent Staining
    The same procedure as in Reference Example 2 was carried out.
1-8. Flow Cytometer Measurement
    The same procedure as in Reference Example 2 was carried out.
1-9. Calculation of Cytokeratin- and Ki-67-Positive Ratios
    The same procedure as in Reference Example 3 was carried out.
2. Results
    FIG. 9A shows charts obtained by overlaying histograms of fluorescence intensities detected with the anti-cytokeratin antibody and the anti-Ki-67 antibody (black solid lines) and histograms of the fluorescent intensities detected with the isotype control antibodies thereof (gray broken lines). For all the FFPE sections, treatment with thrombin increased the fluorescence intensities of both cytokeratin and Ki-67, and also increase positive ratios (FIG. 9B).

Example 4

Figure 10:
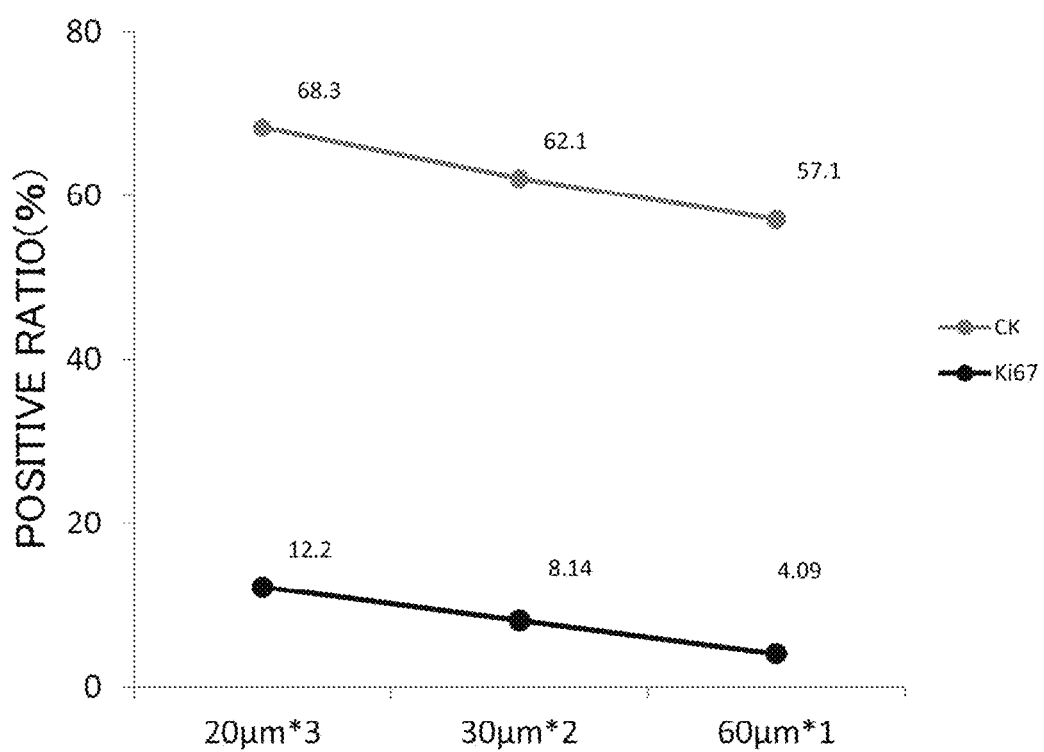
FIG. 10 is a graph showing a change in cytokeratin- and Ki-67-positive ratios depending on the thickness of a section.

Effect of Thickness of Sliced Section on Cytokeratin and Ki-67 Signal Intensities
1. Materials and Method
    Whether the thickness of the FFPE section had an effect on cytokeratin and Ki-67 signal intensities was examined.
1-1. FFPE Tissue Block
    The FFPE tissue block used in Reference Example 1 was used.
1-2. Preparation of FFPE Section
    Three sections with a thickness of 20 µm, two sections with a thickness of 30 µm and one section with a thickness of 60 µm were prepared from one FFPE tissue block with a sliding microtome manufactured by Thermo Fisher Scientific.
1-3. Deparaffinization/Hydrophilization
    The same procedure as in Reference Example 1 was carried out.
1-4. Antigen Retrieval with Heat Treatment
    The same procedure as in Reference Example 1 was carried out.
1-5. Antigen Activation with Enzyme
    The same procedure as in Example 1 was carried out.
1-6. Crushing with Water Flow
    The same procedure as in Reference Example 1 was carried out.
1-7. Immunofluorescent Staining
    The same procedure as in Reference Example 2 was carried out.
1-8. Flow Cytometer Measurement
    The same procedure as in Reference Example 2 was carried out.
1-9. Calculation of Cytokeratin- and Ki-67-Positive Ratios
    The same procedure as in Reference Example 3 was carried out.
2. Results
    FIG. 10 shows the thickness of each of the sections and changes in cytokeratin- and Ki-67-positive ratios.
    Cytokeratin (CK) and Ki-67 (Ki67) could be detected at any thickness in the range of 20 to 60 µm, although the highest detection efficiency was exhibited in the three sections with a thickness of 20 µm.

Example 5

Comparison between Ki-67-Positive Ratios by Flow Cytometer and IHC Method
1. Materials and Method
    With a FFPE tissue block, Ki-67-positive ratios by a flow cytometer and positive ratios by a IHC method were compared.
1-1. FFPE Tissue Block
    19 FFPE tissue blocks were purchased from ProteoGenex, Inc., which were obtained from 19 patients with breast cancer and resulted in different Ki-67-positive ratios by an IHC method.
1-2. Preparation of FFPE Section
    The same procedure as in Reference Example 3 was carried out.
1-3. Deparaffinization/Hydrophilization
    The same procedure as in Reference Example 1 was carried out.
1-4. Antigen Retrieval with Heat Treatment
    The same procedure as in Reference Example 1 was carried out.
1-5. Antigen Activation with Enzyme
    The same procedure as in Example 1 was carried out.
1-6. Crushing with Water Flow
    The same procedure as in Reference Example 1 was carried out.
1-7. Immunofluorescent Staining
    The same procedure as in Reference Example 2 was carried out. Here, a Ki-67 antibody (Dako, clone: MIB-1, mouse monoclonal antibody) and a pan-cytokeratin antibody (Abcam, rabbit polyclonal antibody) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies.
1-8. Flow Cytometer Measurement
    The same procedure as in Reference Example 2 was carried out.
1-9. Calculation of Ki-67-Positive Ratios by Flow Cytometer The same procedure as in Reference Example 3 was carried out.

1-10. Calculation of Ki-67-Positive Ratios by IHC Method

The Ki-67-positive ratios by the IHC method were calculated by a hot spot method with a Ki-67 antibody (Dako, clone: MIB-1, mouse monoclonal antibody) used as a primary antibody. An average of positive ratios determined by two pathologists was employed with consideration given to variability among microscopic observers.

2. Results

Figure 11:
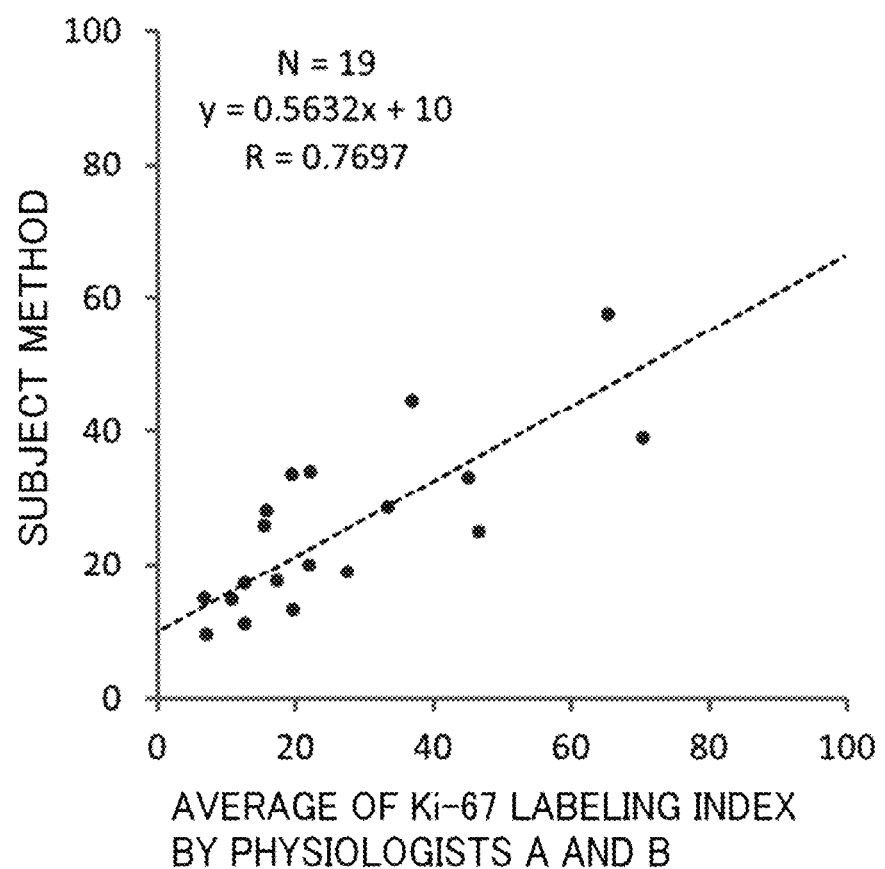
FIG. 11 shows a correlation chart between a Ki-67-positive ratio by a method according to the present invention and a positive ratio (average) by an IHC method.

FIG. 11 shows a correlation with the IHC method in terms of Ki-67-positive ratio.

Examined was a correlation between the IHC method set as X and the subject method set to Y. Since the cutoff value of the positive nuclei was the 90 percentile value of the isotype control, the intercept was set to 10. As shown in FIG. 11, a relationship of Y=0.5632X+10 and a correlation factor of 0.7697 were obtained, and a good correlation was confirmed. This indicates that the subject method enables detection of Ki-67 in a FFPE tissue section.

Example 6

Detection of Ki-67 and Cytokeratin after Antigen Activation with Different Enzymes 1. Materials and Method Formalin-fixed breast cancer cells were subjected to antigen activation with five different digestive enzymes, and the signal intensities of Ki-67 and cytokeratin were compared.

1-1. Cells

The three breast cancer cell lines used in Reference Example 2 were used.

1-2. Cell Culture and Formalin Fixation

The same procedure as in Reference Example 2 was carried out.

1-4. Antigen Retrieval with Heat Treatment

The same procedure as in Reference Example 1 was carried out.

1-5A. Antigen Activation with Enzyme (Thrombin)

The same treatment as in Example 1 was carried out.

1-5B. Antigen Activation with Enzyme (Trypsin)

250 µL of a trypsin reagent (25 mM TBS pH 7.4, 1 M CaCl$_2$), 1 mg/mL trypsin) was added to cells subjected to antigen retrieval with heat treatment, and the cells were heated at 37° C. for 20 minutes. After the enzymatic treatment, the cells were washed with TBS to remove the enzyme.

1-5C. Antigen Activation with Enzyme (Proteinase K)

600 mAnson U/mL of proteinase K (Takara Bio Inc.) was diluted by 40 times (v/v) with 25 mM TBS pH 7.4 to give a proteinase K solution. 250 µL of the proteinase K solution was added to cells subjected to antigen retrieval with heat treatment, and the cells were heated at 37° C. for 20 minutes. After the enzymatic treatment, the cells were washed with TBS to remove the enzyme.

1-5D. Antigen Activation with Enzyme (Dispase)

Dispase (Wako) was dissolved in 25 mM TBS pH 7.4 to give a dispase solution (3,000 PU/mL). 250 µL of the dispase solution was added to cells subjected to antigen retrieval with heat treatment, and the cells were heated at 37° C. for 20 minutes. After completion of the reaction, 2 µL of a 1 M EDTA solution (Wako) was added, and the mixture was mixed by inversion, followed by washing the cells with TBS to remove the enzyme.

1-5E. Antigen Activation with Enzyme (Proline Endopeptidase)

Proline endopeptidase (TOYOBO CO., LTD.) was dissolved in 25 mM TBS pH 7.4 to give a proline endopeptidase solution (10 U/mL). 250 µL of the proline endopeptidase solution was added to cells subjected to antigen retrieval with heat treatment, and the cells were heated at 37° C. for 20 minutes. After completion of the reaction, the cells were washed with TBS to remove the enzyme.

1-7. Immunofluorescent Staining

The same procedure as in Reference Example 2 was carried out. Here, a Ki-67 antibody (Dako, clone: MIB-1, mouse monoclonal antibody) and a pan-cytokeratin antibody (Abcam, rabbit polyclonal antibody) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies.

1-8. Flow Cytometer Measurement

The same procedure as in Reference Example 2 was carried out.

1-9. Calculation of Cytokeratin- and Ki-67-Positive Ratios

The same procedure as in Reference Example 2 was carried out.

2. Results

Figure 12A:
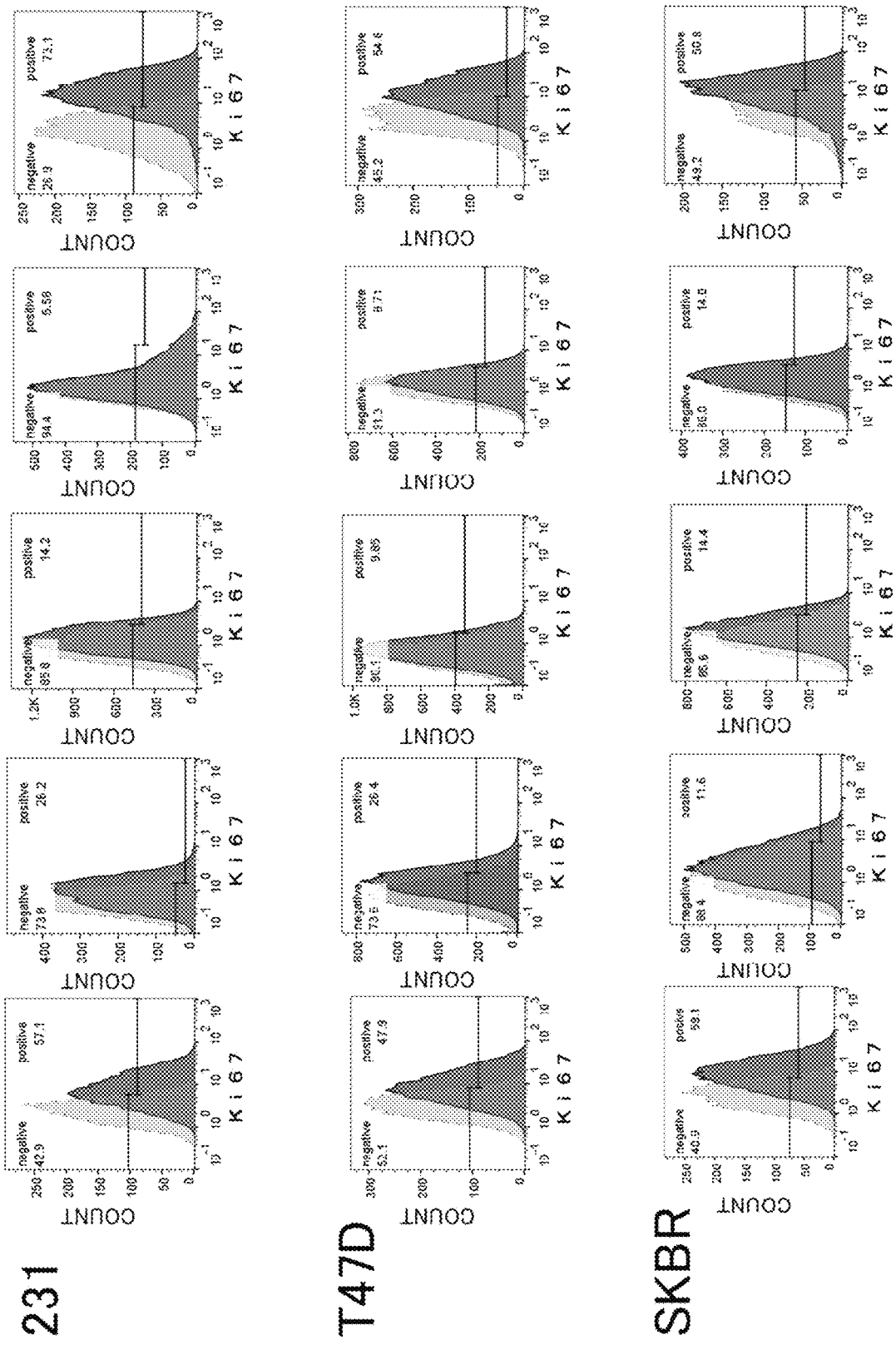
FIG. 12A shows histograms with the fluorescence intensity in the horizontal axis and the number of cells (nuclei) in the vertical axis wherein the histograms were obtained through a process in which formalin-fixed tumor cell lines (MB231, T47D and SKBR) were subjected to antigen retrieval with heat treatment, then subjected to antigen activation with any of five digestive enzymes (thrombin, trypsin, proteinase K, dispase and proline endopeptidase), immunofluorescently stained with an anti-Ki-67 antibody or an isotype control antibody thereof and then measured by a flow cytometer, and the data of fractions gated as a group of cell nuclei were analyzed.
Figure 12B:
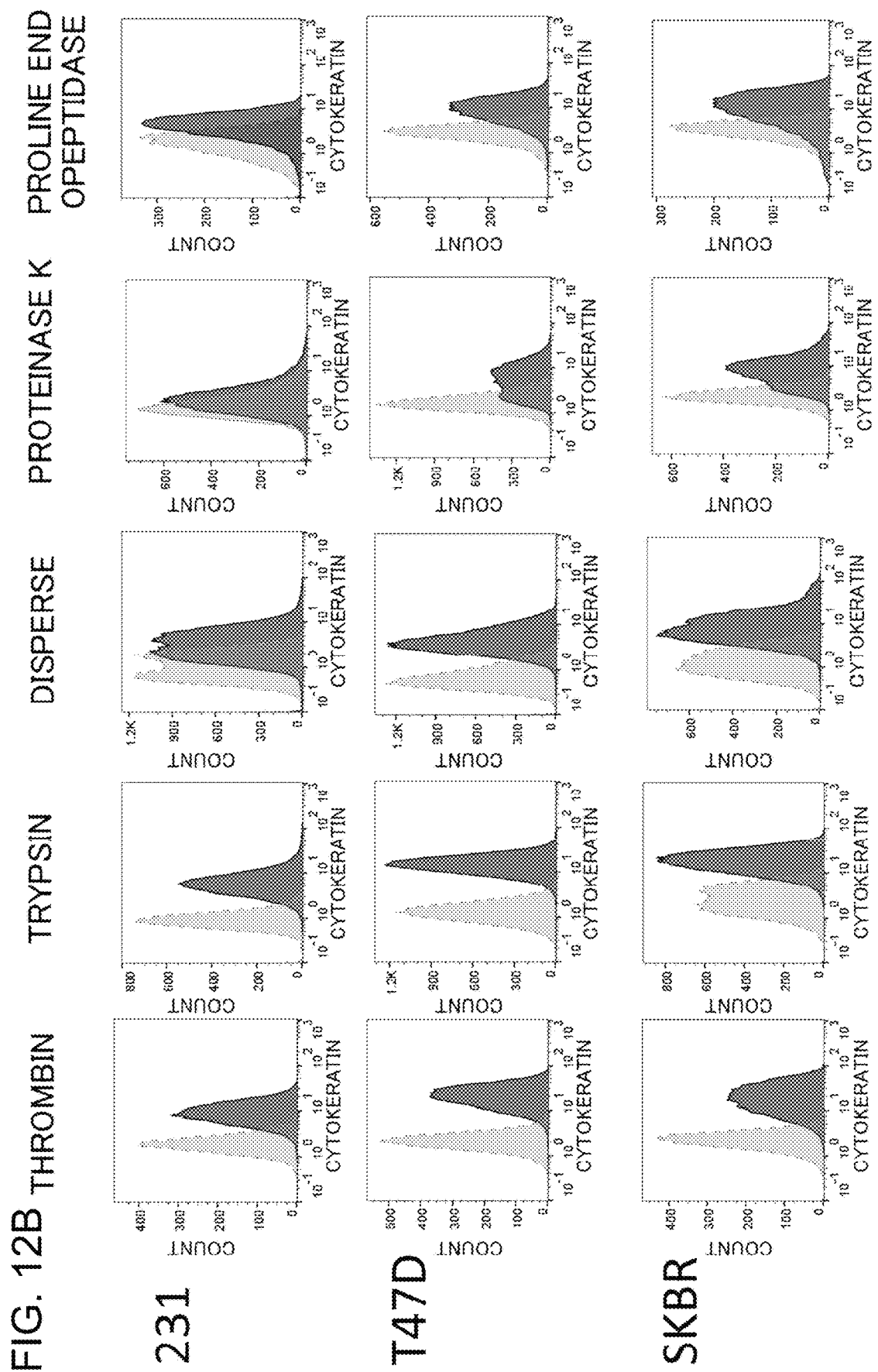
FIG. 12B shows histograms with the fluorescence intensity in the horizontal axis and the number of cells (nuclei) in the vertical axis wherein the histograms were obtained through a process in which formalin-fixed tumor cell lines (MB231, T47D and SKBR) were subjected to antigen retrieval with heat treatment, then subjected to antigen activation with any of five digestive enzymes (thrombin, trypsin, proteinase K, dispase and proline endopeptidase), immunofluorescently stained with an anti-cytokeratin antibody or an isotype control antibody thereof and then measured by a flow cytometer, and the data of fractions gated as a group of cell nuclei were analyzed.

FIGS. 12A and 12B show charts obtained by overlaying histograms of fluorescence intensities detected with the anti-Ki-67 antibody or the anti-cytokeratin antibody (black solid lines) and histograms of the fluorescent intensities detected with the isotype control antibody thereof (gray broken lines). The cytokeratin was detectable irrespective of which proteolytic enzyme was used (FIG. 12B). On the other hand, use of any of the three proteolytic enzymes: trypsin, dispase and proteinase K, which can recognize and cleave the amino acid sequence of SEQ ID NO: 2, caused a decrease in the signal intensity, so that the Ki-67-positive ratio was markedly lowered. In contrast, thrombin and proline endopeptidase which do not recognize or cleave the amino acid sequence of SEQ ID NO: 2 increased the Ki-67-positive ratio, and enhanced the antigenicity of the Ki-67 antigen (FIG. 12A).

Example 7

Detection of Ki-67 and Cytokeratin in FFPE Section of Breast Cancer Tissue after Use of Different Enzymes 1. Materials and Method A FFPE section of a breast cancer tissue was subjected to antigen activation with five different digestive enzymes, and the signal intensities of Ki-67 and cytokeratin were compared.

1-1. FFPE Tissue Block

The FFPE tissue block used in Reference Example 1 was used.

1-2. Preparation of FFPE Section

The same procedure as in Reference Example 3 was carried out.

1-3. Deparaffinization/Hydrophilization

The same treatment as in Reference Example 1 was carried out.

1-4. Antigen Retrieval with Heat Treatment

The same treatment as in Reference Example 1 was carried out.

1-5A. Antigen Activation with Enzyme (Thrombin)

The same procedure as in Example 1 was carried out.

1-5B. Antigen Activation with Enzyme (Trypsin)

The same procedure as in Example 6 was carried out.

1-5C. Antigen Activation with Enzyme (Proteinase K)

The same procedure as in Example 6 was carried out.

Figure 13A:
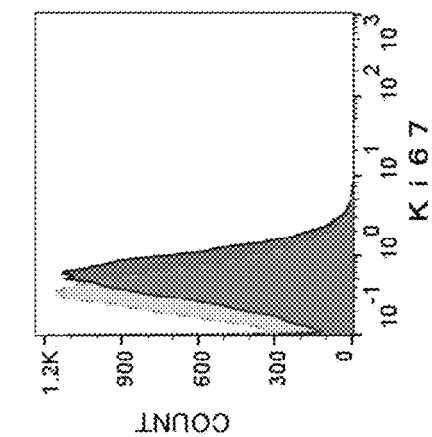
FIG. 13A shows histograms with the fluorescence intensity in the horizontal axis and the number of cells (nuclei) in the vertical axis wherein the histograms were obtained through a process in which a FFPE tissue section of a breast cancer tissue was deparaffinized/hydrophilized, subjected to antigen retrieval with heat treatment, and subjected to antigen activation with any of five digestive enzymes (thrombin, trypsin, proteinase K, dispase and proline endopeptidase), the cells were crushed with a water flow, then immunofluorescently stained with an anti-Ki-67 antibody or an isotype control antibody thereof, and then measured by a flow cytometer, and the data of fractions gated as a group of cell nuclei were analyzed.
Figure 13A:
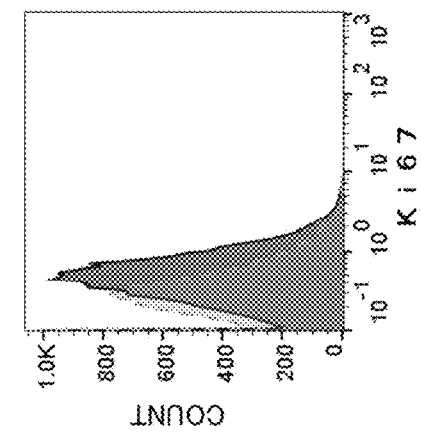
Figure 13A:
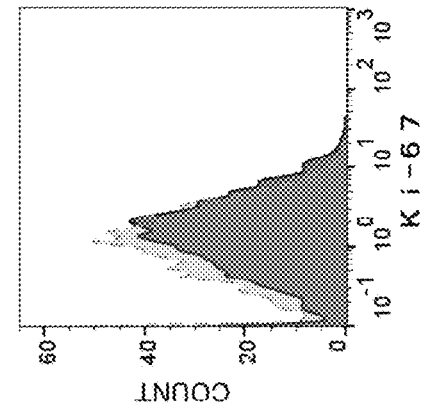
Figure 13A:
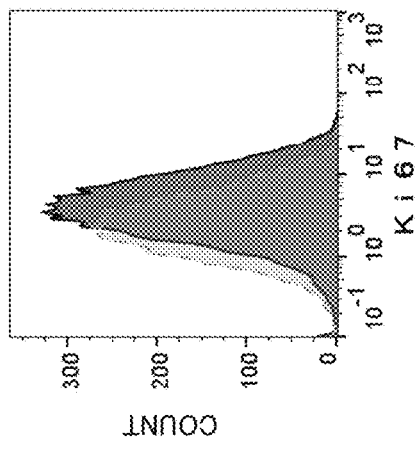
Figure 13A:
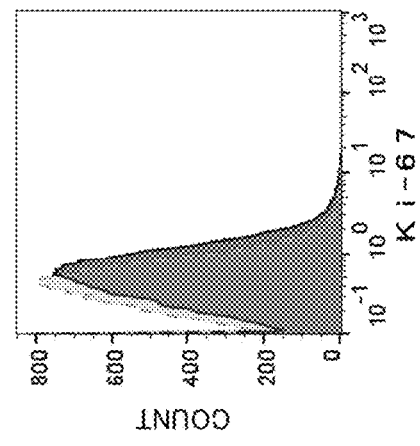

1-5D. Antigen Activation with Enzyme (Dispase)
The same procedure as in Example 6 was carried out.
1-5E. Antigen Activation with Enzyme (Proline Endopeptidase)
The same procedure as in Example 6 was carried out.
1-6. Crushing with Water Flow
The same procedure as in Reference Example 1 was carried out.
1-7. Immunofluorescent Staining
The same procedure as in Reference Example 2 was carried out. Here, a Ki-67 antibody (Dako, clone: MIB-1, mouse monoclonal antibody) and a pan-cytokeratin antibody (Abcam, rabbit polyclonal antibody) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies.
1-8. Flow Cytometer Measurement
The same procedure as in Reference Example 2 was carried out.
1-9. Calculation of Cytokeratin- and Ki-67-Positive Ratios
The same procedure as in Reference Example 3 was carried out.
2. Results
FIGS. 13A and 13B show charts obtained by overlaying histograms of fluorescence intensities detected with the anti-Ki-67 antibody or the anti-cytokeratin antibody (black solid lines) and histograms of the fluorescent intensities detected with the isotype control thereof (gray broken lines). The cytokeratin was detectable irrespective of which proteolytic enzyme was used (FIG. 13B). On the other hand, as in Example 6, the enzymes: trypsin, disperse and proteinase K, which can recognize and cleave the peptide of SEQ ID NO: 2, caused considerable decreases in fluorescence intensity of the Ki-67 antibody (black solid lines) (FIG. 13A).

Example 8

Figure 14:
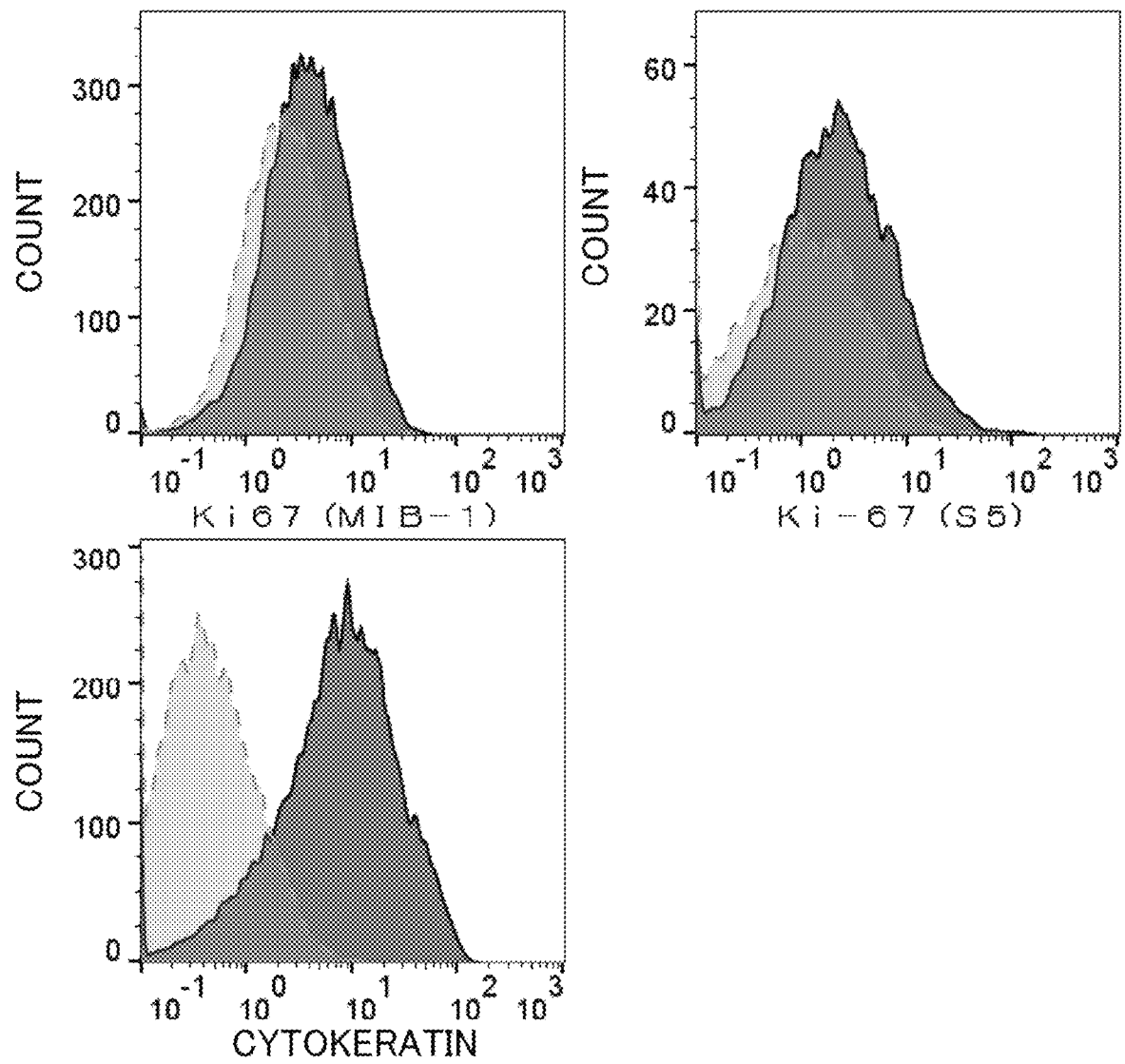
FIG. 14 shows histograms with the fluorescence intensity in the horizontal axis and the number of cells (nuclei) in the vertical axis wherein the histograms were obtained through a process in which a FFPE tissue section of a breast cancer tissue is deparaffinized/hydrophilized, subjected to antigen retrieval with heat treatment, and subjected to antigen activation with thrombin, the cells are crushed with a water flow, then immuno-fluorescently stained with any of two anti-Ki-67 antibodies having different antigen-recognition sites (MIB-1 clone and S5 clone) and an anti-cytokeratin antibody or isotype control antibodies thereof, and then measured by a flow cytometer, and the data of fractions gated as a group of cell nuclei were analyzed.

Detection of Ki-67 with Antibodies Having Different Antigen-Recognition Sites
1. Materials and Method
Signals from cytokeratin and Ki-67 in a FFPE tissue section of a breast cancer tissue were examined by a flow cytometer. As Ki-67 antibodies, MIB-1 clone, and S5 clone, which is different from MIB-1 clone in an antigen-recognition site, were used.
1-1. FFPE Tissue Block
The FFPE tissue block used in Reference Example 1 was used.
1-2. Preparation of FFPE Section
The same procedure as in Reference Example 3 was carried out.
1-3. Deparaffinization/Hydrophilization
The same treatment as in Reference Example 1 was carried out.
1-4. Antigen Retrieval with Heat Treatment
The same treatment as in Reference Example 1 was carried out.
1-5. Antigen Activation with Enzymatic Treatment
The same treatment as in Example 1 was carried out.
1-6. Crushing with Water Flow
The same procedure as in Reference Example 1 was carried out.
1-7. Immunofluorescent Staining
The same procedure as in Reference Example 2 was carried out. A Ki67 MIB-1 antibody (Dako, mouse monoclonal antibody) or a Ki67 S5 antibody (Millipore, mouse monoclonal antibody) and a pan-cytokeratin antibody (Abcam, rabbit polyclonal antibody) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies.
1-8. Flow Cytometer Measurement
The same procedure as in Reference Example 2 was carried out.
1-9. Calculation of Cytokeratin- and Ki-67-Positive Ratios
The same procedure as in Reference Example 3 was carried out.
2. Results
FIG. 14 shows charts obtained by overlaying histograms of fluorescence intensities detected with the anti-Ki-67 antibodies or the anti-cytokeratin antibody (black solid lines) and histograms of the fluorescent intensities detected with the isotype control thereof (gray) (upper side: Ki-67; lower side: cytokeratin). The peaks of the Ki-67 antibodies showed higher fluorescence intensities than that of the isotype control. Thus, it was confirmed that cytokeratin and Ki-67 in the FFPE tissue section were detected, indicating that Ki-67 in a specimen is detectable not only with the MIB-1 clone of Ki-67 but also with the S5 clone of Ki-67.

Comparative Example 1

Detection of Ki-67 Signal in FFPE Tissue Section by Known Method
1. Materials and Method
Signals from cytokeratin and Ki-67 in a FFPR tissue section of a breast cancer tissue were detected by a known method described in a prior art document (Non-Patent Document 4: Cytometry 27: 283-289).
1-1. FFPE Tissue Block
The FFPE tissue block used in Reference Example 1 was used.
1-2. Preparation of FFPE Section
The same procedure as in Reference Example 3 was carried out.
1-3. Deparaffinization/Hydrophilization
The same treatment as in Reference Example 1 was carried out.
1-5. Antigen Activation with Enzyme (Trypsin): Conventional Method
250 µL of a trypsin reagent (25 mM PBS pH 7.4, 1 mg/ml $CaCl_2$), 1 mg/ml trypsin) was added to the hydrophilized tissue section, and the section was heated at 37° C. for 70 minutes. After the enzymatic treatment, the section was washed with PBS to remove the enzyme.
1-7. Immunofluorescent Staining
4% BSA/TBS containing 10% normal goat serum (Wako) was added to a microtube containing the sample after the antigen activation with enzyme, and the sample was placed still at room temperature for 30 minutes, and subjected to blocking treatment. For immunofluorescent staining, a Ki67 MIB-1 antibody (Dako, mouse monoclonal antibody) or a Ki67 S5 antibody (Millipore, mouse monoclonal antibody) and a cytokeratin antibody (Abcam, rabbit polyclonal antibody) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies. The primary antibody reaction was carried out at 4° C. overnight. The secondary antibody was reacted for 40 minutes, and DAPI Solution (Wako) was added to stain cell nuclei 20 minutes after addition of the secondary antibody.

After addition of the secondary antibody, all the reactions were carried out at room temperature under a light-shielding condition. 0.5% BSA/TBS was used as an antibody diluting liquid, and washing with 0.5% BSA/TBS was carried out once between the steps. As a negative control, antibodies identical in type and concentration to respective primary antibodies were used instead of the primary antibodies. A mouse IgG antibody from Dako Company was used as a negative control mouse antibody, and a rabbit IgG antibody from Cell Signaling Technology, Inc. was used as a negative control rabbit antibody.

1-8. Flow Cytometer Measurement

The same procedure as in Reference Example 2 was carried out.

1-9. Calculation of Cytokeratin- and Ki-67-Positive ratios with Flow Cytometer

The same procedure as in Reference Example 3 was carried out.

2. Results

Figure 15:
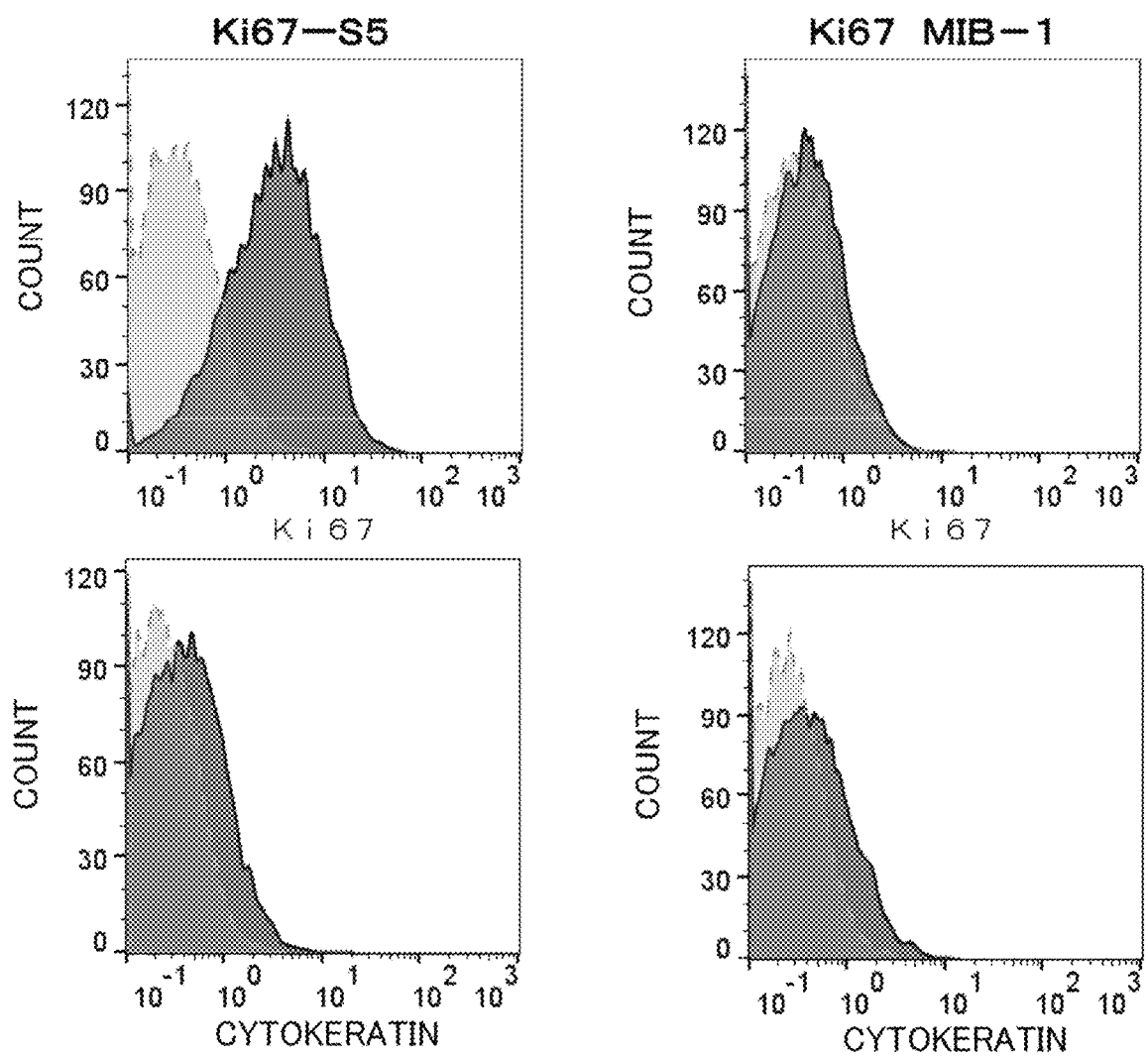
FIG. 15 shows histograms with the fluorescence intensity in the horizontal axis and the number of cells (nuclei) in the vertical axis wherein the histograms were obtained through a process in which in accordance with a known method, a FFPE tissue section of a breast cancer tissue was deparaffinized/hydrophilized, then subjected to antigen activation with trypsin, immunofluorescently stained with any of two anti-Ki-67 antibodies having different antigen-recognition sites (MIB-1 clone and S5 clone) and an anti-cytokeratin antibody or isotype control antibodies thereof, and then measured by a flow cytometer, and the data of fractions gated as a group of cell nuclei were analyzed.

FIG. 15 shows (upper side: Ki-67; lower side: cytokeratin) that the conventional method described in Non-Patent Document 4 could detect Ki-67 when the S5 clone of Ki-67 was used, but caused a considerable decrease in Ki-67-derived fluorescence peak, and could not detect Ki-67 when the MIB-1 clone antibody was used.

Example 9

Detection of ER and PgR in FFPE Section

1. Materials and Method

FFPE tissue sections already known to be ER- and PgR-positive and negative were subjected to antigen activation with thrombin, cell nuclei were extracted by crushing them with a water flow, and signals from ER and PgR were examined by a flow cytometer.

1-1. FFPE Tissue Block

FFPE tissue blocks of an ER-positive specimen (Allred Score ER7) and a PgR-positive specimen (Allred Score PgR8) purchased from ProteoGenex, Inc were used as ER- and PgR-positive samples, and FFPE tissue blocks of ER- and PgR-negative specimens (Allred Score ER0 and PgR0) were used as ER- and PgR-negative samples.

1-2. Preparation of FFPE Section

The same procedure as in Reference Example 3 was carried out.

1-3. Deparaffinization/Hydrophilization

The same treatment as in Reference Example 1 was carried out.

1-4. Antigen Retrieval with Heat Treatment

The same treatment as in Reference Example 1 was carried out.

1-5. Antigen Activation with Enzyme

After the antigen retrieval with heat treatment, the ER-positive sample was subjected to antigen activation with thrombin. In addition, the PgR-positive sample and the ER- and PgR-negative samples were subjected to antigen activation with thrombin or proline endopeptidase. Antigen activation with thrombin was carried out in the same manner as in Example 1, and antigen activation with proline endopeptidase was carried out in the same manner as in Example 6.

1-6. Crushing with Water Flow

The same procedure as in Reference Example 1 was carried out.

1-7. Immunofluorescent Staining

4% BSA/TBS containing 10% normal goat serum (Wako) was added to a microtube containing a sample after crushing the cells with a water flow, and the mixture was placed still at room temperature for 30 minutes and subjected to blocking treatment. For immunofluorescent staining, an ER antibody (Abcam, clone: S P1, rabbit monoclonal antibody) or a PgR antibody (Thermo Fisher, clone: SP2, rabbit monoclonal antibody) was used as a primary antibody, and Goat anti-Rabbit Mouse Secondary Antibody Alexa 488 from Abcam PLC was used as a secondary antibody. The primary antibody was reacted at room temperature for 45 minutes. The secondary antibody was reacted at room temperature for 40 minutes, and DAPI Solution (Wako) was added to stain cell nuclei 20 minutes after addition of the secondary antibody.

1-8. Flow Cytometer Measurement

The same procedure as in Reference Example 2 was carried out.

1-9. Calculation of ER and PgR-Positive Ratios

For analysis of the obtained measurement data, software FlowJo v10 manufactured by FLOWJO LLC was used. In a chart with the fluorescence intensities of DAPI in the horizontal axis and the number of cells (nuclei) in the vertical axis, an area in which the fluorescence intensities in the horizontal axis are 5 to 150 was gated as cell nuclei. The ER- and PgR-positive ratios in the area were calculated as ratios of the number of ER-positive nuclei and the number of PgR-positive nuclei with respect to the number of all cell nuclei. The threshold value of the positive nuclei was set to the 90 percentile value of the isotype control.

2. Results

Figure 16:
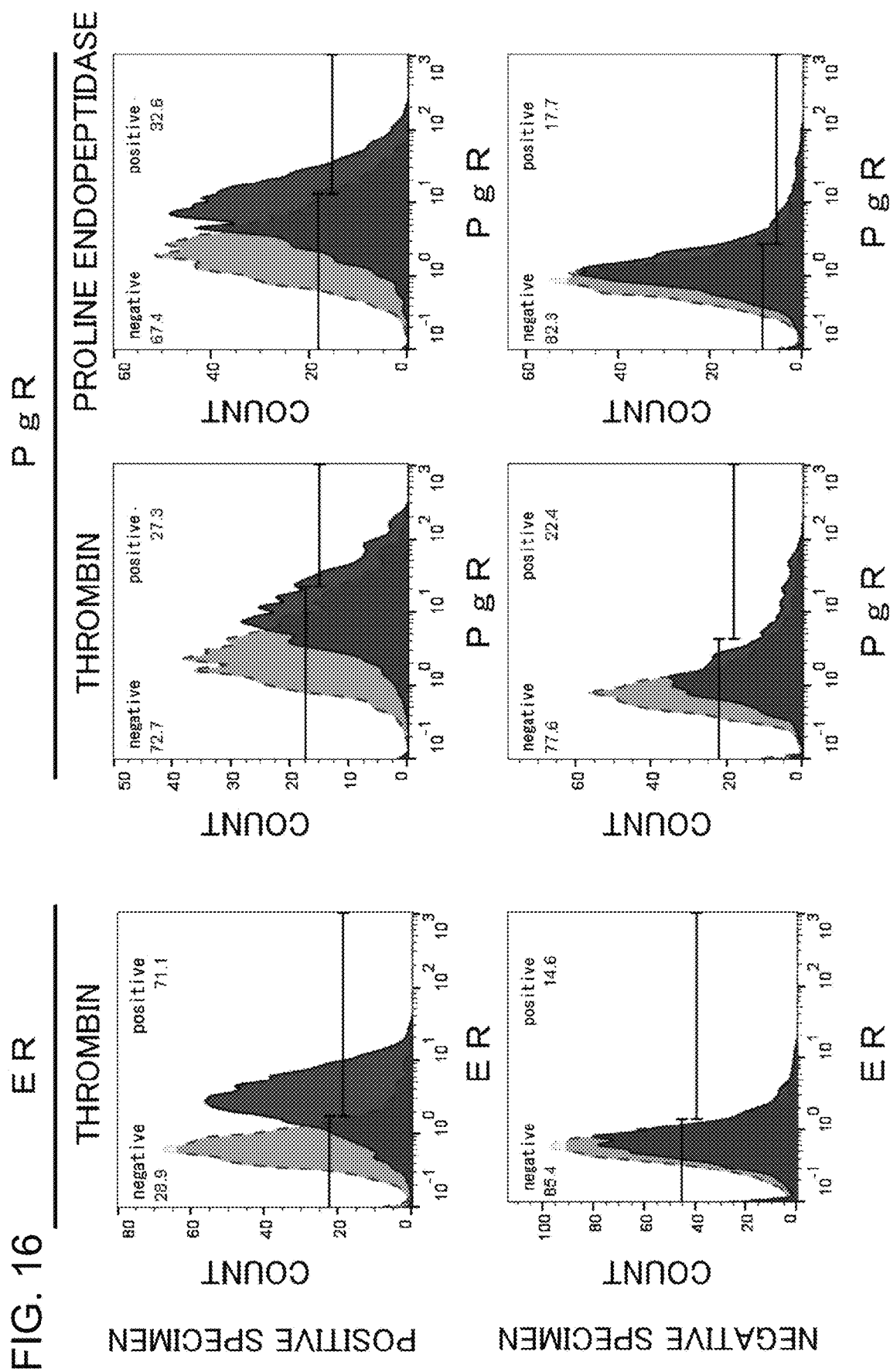
FIG. 16 shows histograms with the fluorescence intensity in the horizontal axis and the number of cells (nuclei) in the vertical axis wherein the histograms were obtained through a process in which FFPE tissue sections known to be ERand PgR-positive or negative were deparaffinized/hydrophilized, then subjected to antigen retrieval with heat treatment, and subjected to antigen activation with thrombin, the cells were crushed with a water flow, then immuno-fluorescently stained with an anti-ER antibody and an anti-PgR antibody or isotype control antibodies thereof, and then measured by a flow cytometer, and the data of fractions gated as a group of cell nuclei were analyzed.

FIG. 16 shows charts obtained by overlaying histograms of the fluorescence intensities detected with the anti-ER antibody or the anti-PgR antibody (black solid lines) and histograms of the fluorescent intensities detected with the isotype control antibody thereof (gray broken lines). Even when the ER-positive and PgR-positive FFPE tissue sections were treated with enzymes which do not recognize or cleave the peptide of SEQ ID NO: 2, the black line peaks showed higher fluorescence intensities as compared to the gray line peaks, and thus both ER and PgR were detected. ER ad PgR were not detected in the ER- and PgR-negative FFPE tissue sections.

Example 10

Comparison of Signals from Ki-67 and Cytokeratin in Fixed Breast Cancer Cells with Heat-Treatment with Different Antigen Retrieval Agents 1. Materials and Method A formalin-fixed breast cancer cell line MDA-MB-231 was subjected to antigen retrieval with heat treatment with three kinds of antigen retrieval agents, subjected to enzymatic treatment with thrombin, and then immunofluorescently stained. Cytokeratin and Ki-67 were detected by a flow cytometer.

1-1. Cells

Breast cancer cell line MDA-MB-231 was obtained from ATCC (American Type Culture Collection).

1-2. Cell Culture and Formalin Fixation

The same procedure as in Reference Example 2 was carried out.

1-4A. Antigen Retrieval with Heat Treatment (Histo VT ONE)

The same treatment as in Reference Example 1 was carried out.

1-4B. Antigen Retrieval with Heat Treatment (Antigen Activation Solution pH 9)

Antigen Retrieval Solution pH 9 (Nichirei Bioscience Inc.) was used. The process procedure and conditions were the same as in Reference Example 1.

1-4C. Antigen Retrieval with Heat Treatment (ImmunoSaver)

ImmunoSaver (Nisshin EM Co., Ltd.) was used. The process procedure and conditions were the same as in Reference Example 1.

1-5. Antigen Activation with Enzyme

The same treatment as in Example 1 was carried out.

1-7. Immunofluorescent Staining

The same procedure as in Reference Example 2 was carried out.

1-8. Flow Cytometer Measurement

The same procedure as in Reference Example 2 was carried out.

1-9. Calculation of Cytokeratin- and Ki-67-Positive Ratios

The same procedure as in Reference Example 3 was carried out.

2. Results

Figure 17:
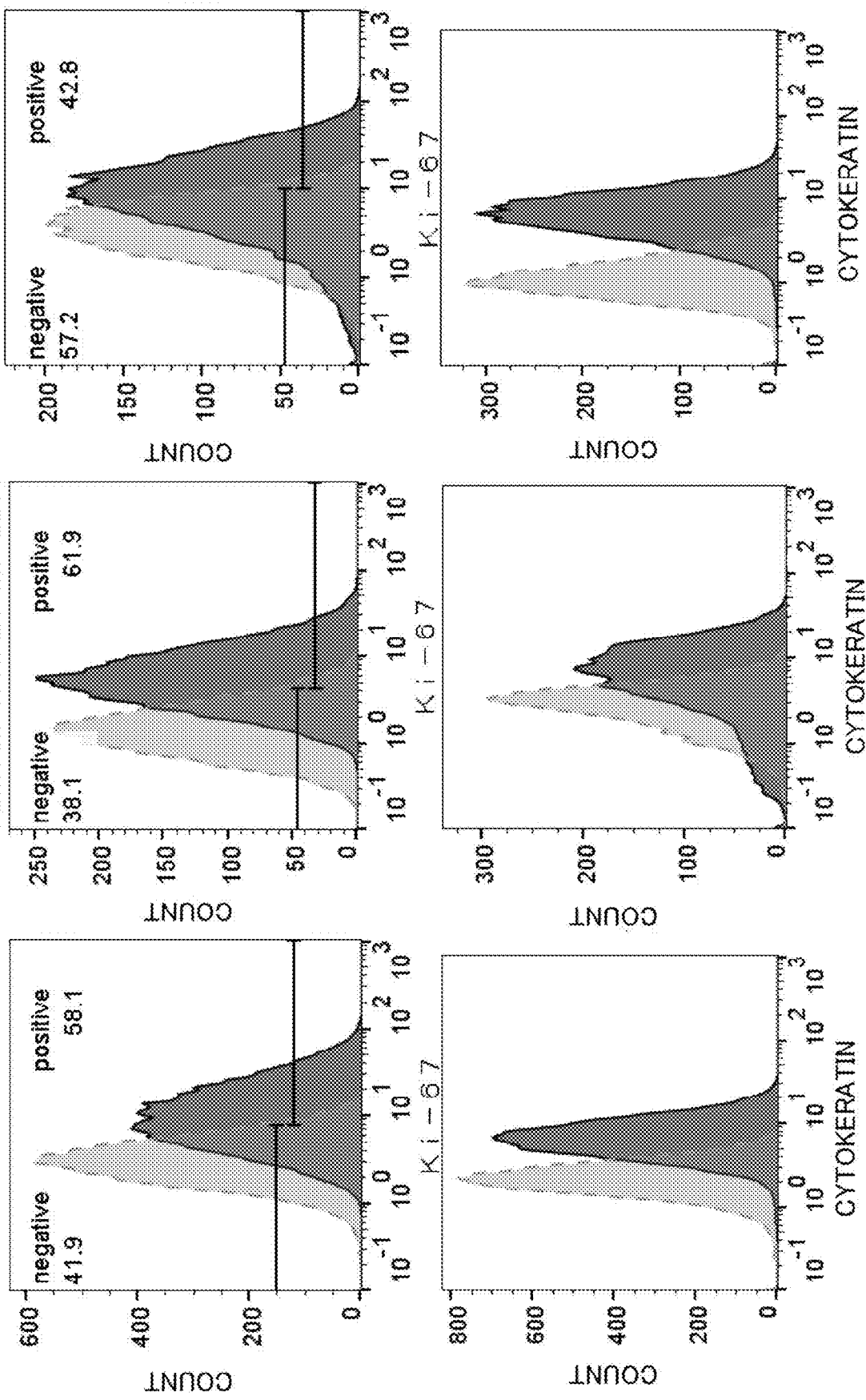
FIG. 17 shows histograms with the fluorescence intensity in the horizontal axis and the number of cells (nuclei) in the vertical axis wherein the histograms were obtained through a process in which a formalin-fixed breast cancer cell line MDA-MB-231 was subjected to antigen retrieval with different antigen retrieval agents for heat-treatment, then subjected to antigen activation with thrombin, and immunofluorescently stained with an anti-Ki-67 antibody and an anti-cytokeratin antibody or isotype control antibodies thereof, and the data of fractions gated as a group of cell nuclei were analyzed.

FIG. 17 shows charts obtained by overlaying histograms of the fluorescence intensities detected with the anti-Ki-67 antibody or the anti-cytokeratin antibody (black solid lines) and histograms of the fluorescent intensities detected with the isotype control antibody thereof (gray broken lines) (upper side: Ki-67; lower side: cytokeratin). The black line peaks showed higher fluorescence intensities as compared to the gray line peaks regardless of which activation solution was used. Thus, it was confirmed that cytokeratin and Ki-67 in the formalin-fixed cells were detected, and that the above-described method was effective even when the activation liquid was changed.

Example 11

Effect of Various Crushing Methods in Step of Extracting Cell Nuclei on Detection of Cytokeratin and Ki-67 in FFPE Tissue Section 1. Materials and Method From FFPE tissue sections of a breast cancer tissue, cell nuclei were extracted by three crushing methods and a combination of crushing methods, and the signal intensities of cytokeratin and Ki-67 were compared by a flow cytometer.

1-1. FFPE Tissue Block

The FFPE tissue block used in Reference Example 1 was used.

1-2. Preparation of FFPE Section

The same procedure as in Reference Example 3 was carried out.

1-3. Deparaffinization/Hydrophilization

The same procedure as in Reference Example 1 was carried out.

1-4. Antigen Retrieval with Heat Treatment

The same procedure as in Reference Example 1 was carried out.

1-5. Antigen Activation with Enzyme

The same treatment as in Example 1 was carried out.

1-6A. Masher

The tissue treated with enzyme was ground twenty times in 1 mL of TBS in an ice-cooled environment by BioMasher (registered trademark) II from Nippi, Inc.

1-6B. Mortar

The tissue treated with enzyme was ground in 1 mL of TBS using a mortar and a pestle.

1-6C. Crushing with Ultrasonication

The tissue treated with enzyme was crushed at an output intensity of 40% for 20 seconds in 1 mL of TBS in an ice-cooled environment by an ultrasonic crushing apparatus (VCX130PB) from Sonics & Materials, Inc.

1-6D. Combination of Crushing with Water Flow and Crushing with Ultrasonication

The tissue treated with enzyme was crushed at 10,000 rpm for 1 minute in 1 mL of TBS in an ice-cooled environment by a water flow shear apparatus (RP-10) from Sysmex Corporation. Further, the tissue after the crushing with a water flow was crushed at an output intensity of 20% for 30 seconds in 1 mL of TBS in an ice-cooled environment by an ultrasonic crushing apparatus (VCX130PB) from Sonics & Materials, Inc.

1-7. Immunofluorescent Staining

The same procedure as in Reference Example 2 was carried out.

1-8. Flow Cytometer Measurement

The same procedure as in Reference Example 2 was carried out.

1-9. Calculation of Cytokeratin and Ki-67-Positive Ratios

For analysis of the obtained measurement data, software FlowJo v10 manufactured by FLOWJO LLC was used. In a chart with the fluorescence intensities of DAPI in the horizontal axis and the number of cells (nuclei) in the vertical axis, an area in which the fluorescence intensities in the horizontal axis are 5 to 150 was gated as cell nuclei. The cytokeratin- and Ki-67-positive ratios in the area were calculated as ratios of the number of cytokeratin-positive nuclei and the number of Ki-67-positive nuclei with respect to the number of all cell nuclei. The threshold value of the positive nuclei was set to the 90 percentile value of the isotype control.

2. Results

Figure 18:
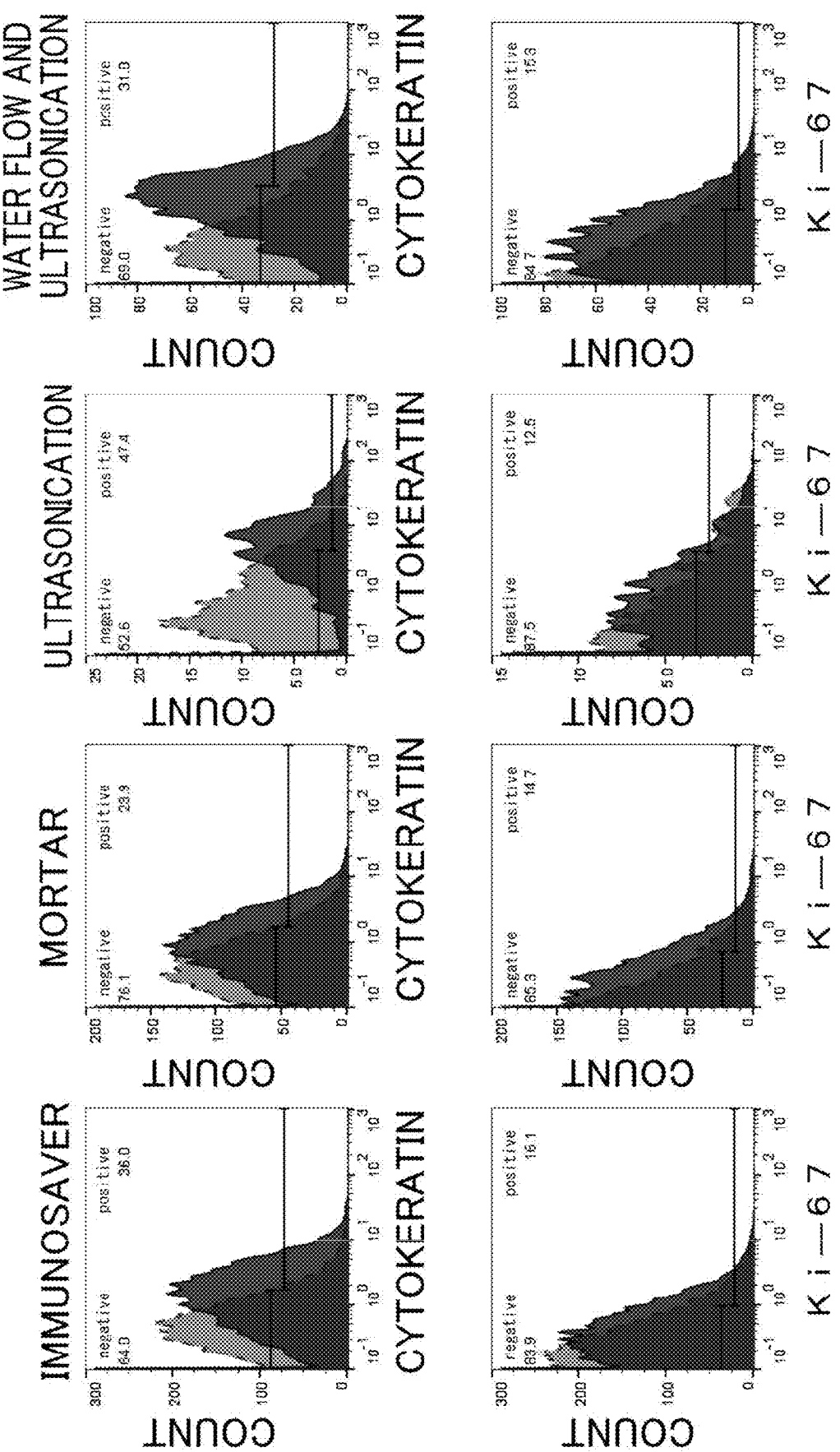
FIG. 18 shows histograms with the fluorescence intensity in horizontal axis and the number of cells (nuclei) in the vertical axis wherein the histograms were obtained through a process in which a FFPE tissue section of a breast cancer tissue was deparaffinized/hydrophilized, subjected to antigen retrieval with heat treatment, and subjected to antigen activation with thrombin, the cells were crushed by applying any of four different crushing methods (masher, mortar, ultrasonic disruption, and combination of ultrasonic disruption and disruption by water flow), then immunofluorescently stained with an anti-cytokeratin antibody and an anti-Ki-67 antibody or isotype control antibodies thereof, and then measured by a flow cytometer, and the data of fractions gated as a group of cell nuclei were analyzed.

FIG. 18 shows charts obtained by overlaying histograms of the fluorescence intensities detected with the anti-cytokeratin antibody or the anti-Ki-67 antibody (black solid lines) and histograms of the fluorescent intensities detected with the isotype control antibody thereof (gray broken lines). The black solid line peaks showed higher fluorescence intensities as compared to the gray broken line peaks regardless of which crushing method is used. Thus, it was confirmed that it was possible to use various crushing methods for detection of cytokeratin and Ki-67 in a FFPE tissue section.

Example 12

Preferential Crushing of Lymphocytes by Crushing with Ultrasonication

1. Materials and Method

Whether crushing with an ultrasonication had an effect on acquirement of cell nuclei was examined with a formalin-fixed breast cancer cell line and lymphoblastic cell line.

1-1. Cells

Breast cancer cell lines SKBr3 and MDA-MB-231 and a lymphoblastic cell line Jurkat were obtained from ATCC (American Type culture Collection).

1-2. Cell Culture and Formalin Fixation 1-4. Antigen Retrieval with Heat Treatment The same treatment as in Reference Example 1 was carried out.

1-5. Antigen Activation Treatment with Enzyme

The same treatment as in Example 1 was carried out.

1-6. Crushing with Ultrasonication

Figure 19:
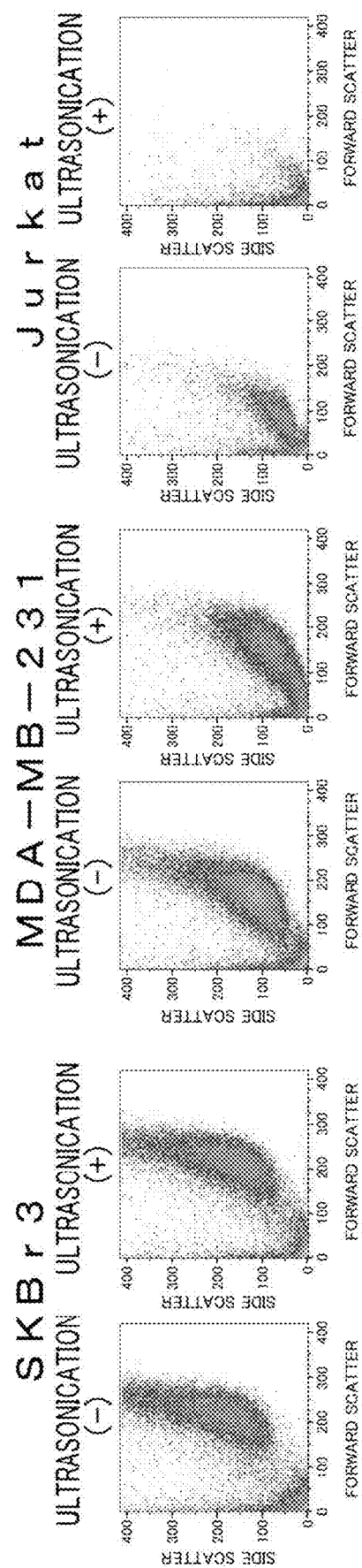
FIG. 19 shows scattergrams with the forward scatter in the horizontal axis and the side scatter in the vertical axis wherein the scattergrams were obtained through a process in which two formalin-fixed cancer cell lines SKBr3 and MDA-MB-231, and a lymphoblastic cell line Jurkat were subjected to antigen retrieval with heat treatment, and subjected to antigen activation with thrombin, the cells were crushed with ultrasonication, the cell nuclei were stained, the cells were then measured by a flow cytometer, and the obtained data were analyzed.

The cells treated with enzyme were crushed at an output intensity of 20% for 30 seconds in 1 mL of TBS in an ice-cooled environment by an ultrasonic crushing apparatus (VCX130PB) from Sonics & Materials, Inc.
1-7. Staining of Cell Nuclei
DAPI Solution (Wako) was added to stain cell nuclei, and reaction was carried out for 20 minutes under a light-shielding condition.
1-8. Flow Cytometer Measurement
The same procedure as in Reference Example 2 was carried out.
2. Results
FIG. 19 shows scattergrams of the respective cell lines with the forward scatter in the horizontal axis and the side scatter in the vertical axis. It is confirmed that in breast cancer cells SKBr3 and MDA-MB-231, the positions of principal cell nucleus regions did not vary depending on whether crushing with ultrasonication was performed or not. On the other hand, crushing with ultrasonication caused principal cell nucleus regions to disappear in lymphocytes Jurkat. These results indicated that epithelial cells were not disrupted by crushing them with ultrasonication, whereas lymphoblastic cells were preferentially crushed with ultrasonication.

Example 13

Figure 20:
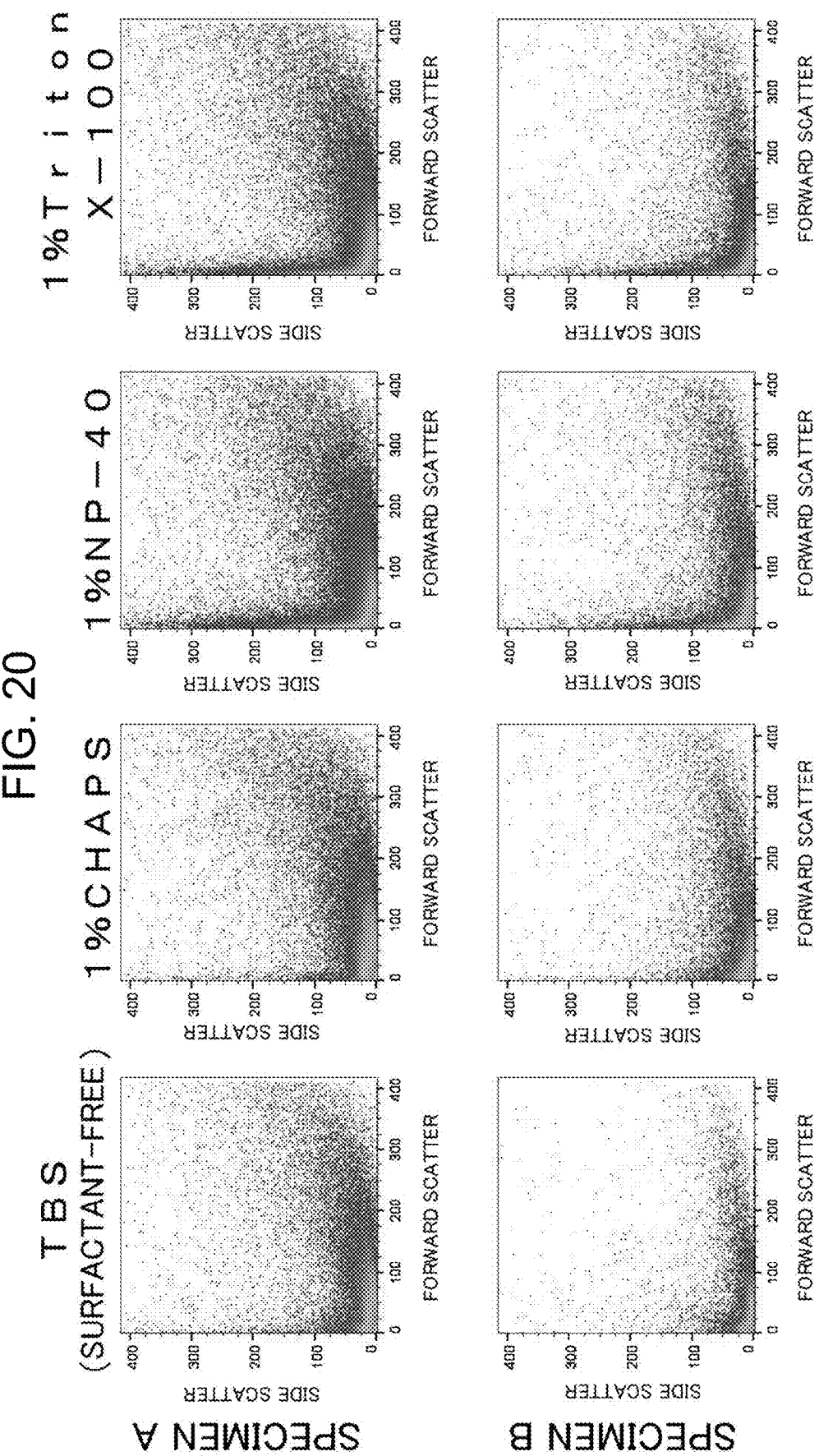
FIG. 20 shows scattergrams with the forward scatter in the horizontal axis and the side scatter in the vertical axis wherein the scattergrams were obtained through a process in which a FFPE tissue section of a breast cancer tissue was subjected to a predetermined pretreatment, and treated with thrombin, the cells were crushed with a water flow, dispersed in buffer solutions containing various surfactants and crushed with ultrasonication, the cell nuclei were then stained, the cells were then measured by a flow cytometer, and the obtained data were analyzed.

Increase in Number of Analyzed Cell Nuclei by Addition of Surfactant
1. Materials and Method
A FFPE tissue section of a breast cancer tissue was used. A surfactant was added at the time of crushing it with ultrasonication, and whether the addition of the surfactant affected acquirement of cell nuclei was examined.
1-1. FFPE Tissue Block
Two FFPE tissue blocks were purchased from Proteo-Genex, Inc., which were obtained from two patients with breast cancer and resulted in different Ki-67-positive ratios by a IHC method.
1-2. Preparation of FFPE Section
The same procedure as in Reference Example 3 was carried out.
1-3. Deparaffinization/Hydrophilization
The same procedure as in Reference Example 1 was carried out.
1-4. Antigen Retrieval with Heat Treatment
The same procedure as in Reference Example 1 was carried out.
1-5. Antigen Activation Treatment with Enzyme
The same treatment as in Example 1 was carried out.
1-6. Crushing with Ultrasonication
An ultrasonic crushing apparatus (VCX130PB) from Sonics & Materials, Inc., was used to crush the tissues and cells subjected to antigen activation with enzyme at an output intensity of 20% for 30 seconds in 1 mL of TBS, 1% CHAPS (Wako)-containing TBS, 1% NP-40 (Wako)-containing TBS or 1% Triton™ X-100 (Wako)-containing TBS in an ice-cooled environment.
1-7. Staining of Cell Nuclei
DAPI Solution (Wako) was added to stain cell nuclei, and reaction was carried out for 20 minutes under a light-shielding condition.
1-8. Flow Cytometer Measurement
The same procedure as in Reference Example 2 was carried out.
2. Results
FIG. 20 shows scattergrams with the forward scatter in the horizontal axis and the side scatter in the vertical axis in the cases that the tissues and cells were crushed with ultrasonication in surfactant-free buffer solutions and in the cases that the tissues and cells were crushed with ultrasonication in buffer solutions containing various surfactants, and Table 3 shows the total number of analyzed cell nuclei during flow cytometer measurement. It was confirmed that addition of a surfactant increased the total number of analyzed cell nuclei.

TABLE 3

|  | Specimen A | Specimen B |
| --- | --- | --- |
| TBS (surfactant-free) | 131027 | 40642 |
| +1% CHAPS | 144233 | 72561 |
| +1% NP-40 | 289745 | 91164 |
| +1% Triton-X100 | 216606 | 97388 |

Comparative Example 2

Figure 21:
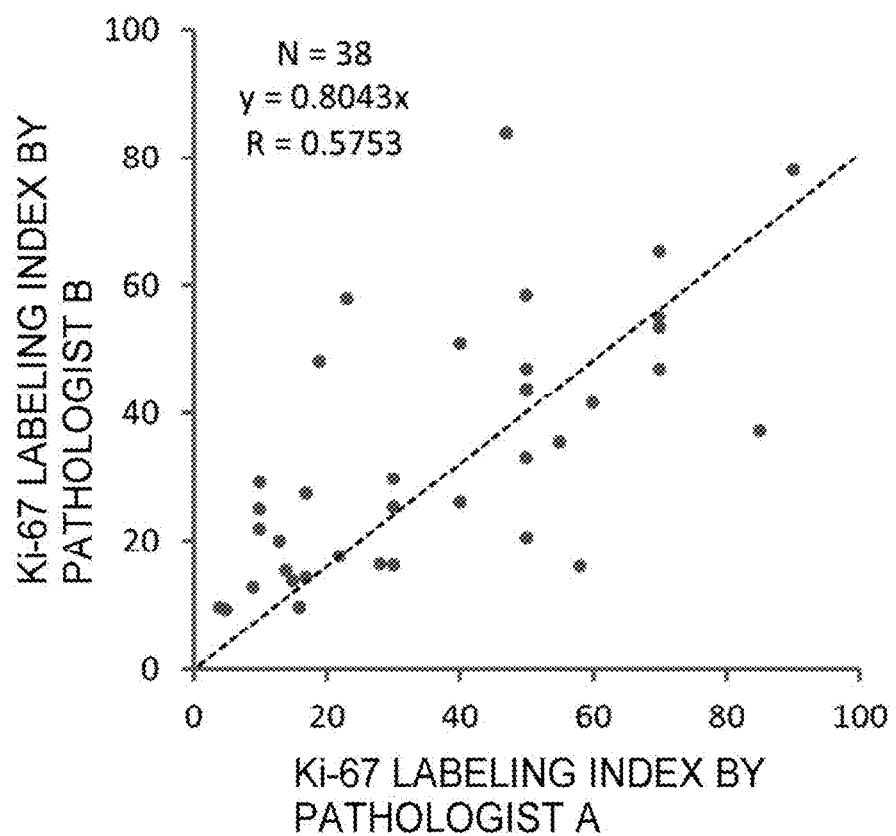
FIG. 21 shows a correlation chart between Ki-67 positive ratios obtained by two different pathologists in a FFPE tissue section of a breast cancer tissue in accordance with the IHC method.

Measurement of Ki-67-Positive Cells by Different Pathologists
1. Materials and Method
A correlation between Ki-67-positive ratios in FFPE tissue sections determined by two pathologists according to an IHC method was examined.
1-1. FFPE Tissue Block
38 FFPE tissue blocks were purchased from ProteoGenex, Inc., which were obtained from 38 patients and resulted in different Ki-67-positive ratios by the IHC method.
1-10. Calculation of Ki-67-Positive Ratio by IHC Method
The same procedure as described in Example 5 was carried out.
2. Results
FIG. 21 shows the results. Even with the same sample, the value of the Ki-67-positive ratio varied depending on a pathologist, and there was relatively large variability between the pathologists.

Reference Example 4

Detection with Anti-Ki-67 Antibodies Having Different Antigen-Recognition Sites after Antigen Activation with Various Enzymes
1. Materials and Method
Formalin-fixed breast cancer cells were subjected to antigen activation with any of three digestive enzymes (thrombin, disperse and proteinase K), and then immunofluorescently stained. Ki-67 and cytokeratin were detected by a flow cytometer.
1-1. Cells
The three breast cancer cell lines used in Reference Example 2 were used.
1-2. Cell Culture and Formalin Fixation
The same procedure as in Reference Example 2 was carried out.
1-4. Antigen Retrieval with Heat Treatment
The same treatment as in Reference Example 1 was carried out.
1-5A. Antigen Activation with Enzyme (Thrombin)
The same treatment as in Example 1 was carried out.
1-5B. Antigen Activation with Enzyme (Disperse)
The same treatment as in Example 6 was carried out.
1-5C. Antigen Activation with Enzyme (Proteinase K)
The same treatment as in Example 6 was carried out.
1-7. Immunofluorescent Staining
The same procedure as in Reference Example 2 was carried out. Here, a Ki-67 antibody (Millipore, clone: S5(Ki-S5), mouse monoclonal antibody) and a pan-cytokeratin antibody (Abcam, rabbit polyclonal antibody) were used as primary antibodies, and Goat anti-Mouse Secondary Antibody Alexa 647 from Thermo Fisher Scientific and Goat anti-Rabbit Secondary Antibody Alexa 488 from Abcam PLC were used as secondary antibodies.

1-8. Flow Cytometer Measurement

The same procedure as in Reference Example 2 was carried out.

1-9. Calculation of Ki-67-Positive-Ratios

The same procedure as in Reference Example 3 was carried out.

2. Results

Figure 22A:
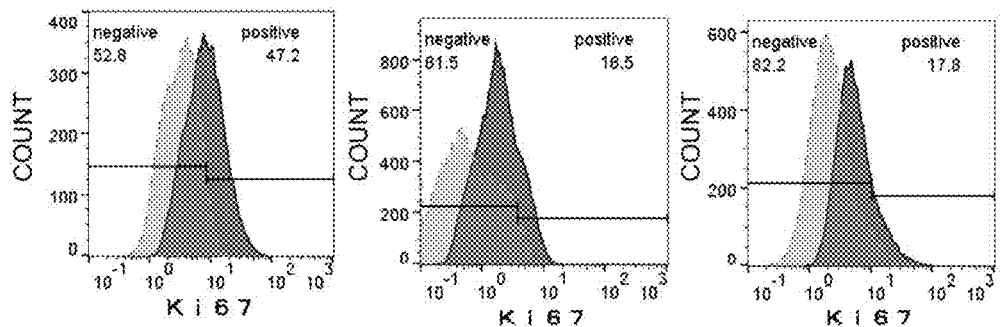
FIG. 22A shows histograms with the fluorescence intensity in the horizontal axis and the number of cells (nuclei) in the vertical axis wherein the histograms were obtained through a process in which formalin-fixed tumor cell lines (MB231, T47D and SKBR) were subjected to antigen retrieval with heat treatment, subjected to antigen activation with any of three digestive enzymes (thrombin, proteinase K and dispase), then immunofluorescently stained with an anti-Ki-67 antibody S5 clone (Ki-S5) or an isotype control antibody thereof, and measured by a flow cytometer, and the data of fractions gated as a group of cell nuclei were analyzed.
Figure 22A:
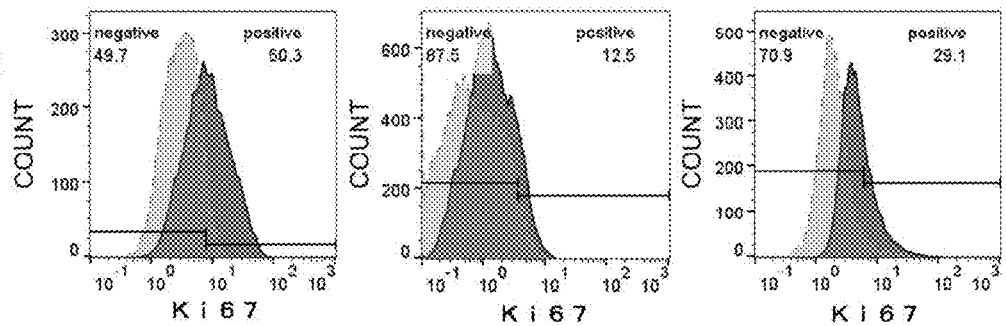
Figure 22A:
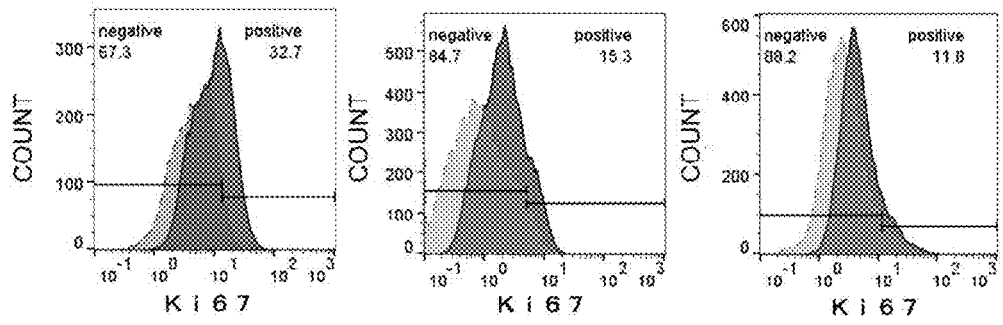
Figure 22B:
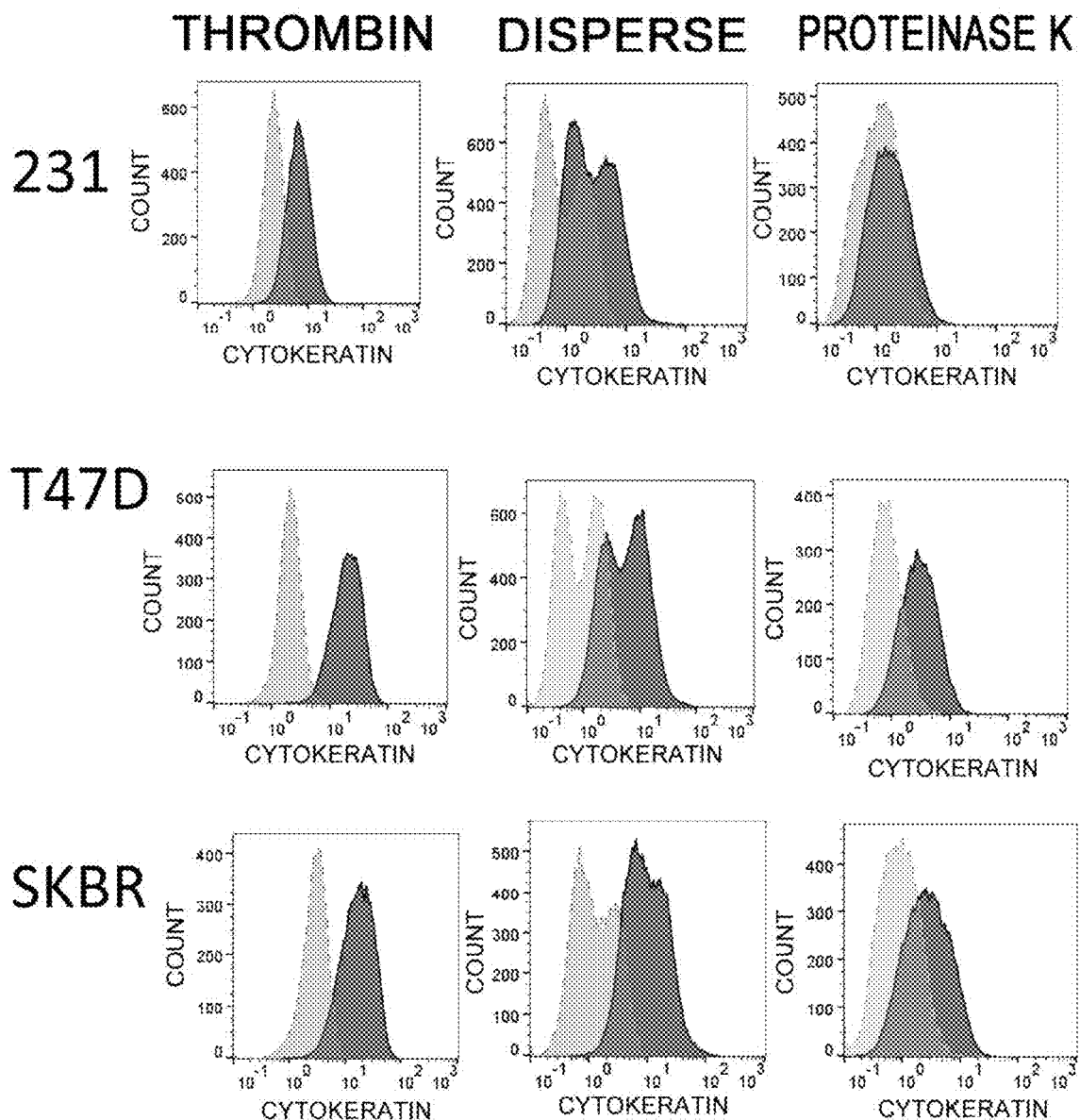
FIG. 22B shows histograms with the fluorescence intensity in the horizontal axis and the number of cells (nuclei) in the vertical axis wherein the histograms were obtained through a process in which formalin-fixed tumor cell lines (MB231, T47D and SKBR) were subjected to antigen retrieval with heat treatment, subjected to antigen activation with any of three digestive enzymes (thrombin, proteinase K and dispase), then immunofluorescently stained with an anti-cytokeratin antibody or an isotype control antibody thereof, and measured by a flow cytometer, and the data of fractions gated as a group of cell nuclei were analyzed.

FIGS. 22A and 22B show charts obtained by overlaying histograms of the fluorescence intensities detected with the anti-Ki-67 antibody (Ki-S5) or the anti-cytokeratin antibody (black solid lines) and histograms of the fluorescent intensities detected with the isotype control thereof (gray broken lines). The black solid line peaks showed higher fluorescence intensities as compared to the gray broken line peaks regardless of which enzyme is used to perform antigen activation. Thus, it was confirmed that in all cases of the enzymes used to perform antigen activation, the epitopes, which the anti-Ki-67 antibody (Ki-S5) and the anti-cytokeratin antibody bind to were maintained, whereby it was possible to detect Ki-67 and cytokeratin.

Example 14

Study on Threshold Value in Determination of Cytokeratin- and Ki-67-Positive Nuclei in FFPE Tissue Section 1. Materials and Method Signals derived from cytokeratin and Ki-67 in a FFPE tissue section were detected by a flow cytometer, and positive ratios were calculated while changing a threshold value of positive nuclei.

1-1. FFPE Tissue Block

The FFPE tissue block used in Reference Example 1 was used. 1-2. Preparation of FFPE Section The same procedure as in Reference Example 3 was carried out.

1-3. Deparaffinization/Hydrophilization

The same procedure as in Reference Example 1 was carried out.

1-4. Antigen Retrieval with Heat Treatment

The same procedure as in Reference Example 1 was carried out.

1-5. Antigen Activation with Enzyme

The same procedure as in Example 1 was carried out.

1-6. Combination of Crushing with Water Flow and Crushing with Ultrasonication

The tissue treated with enzyme was crushed at 10,000 rpm for 1 minute in 1 mL of TBS in an ice-cooled environment by a water flow shear apparatus (RP-10) from Sysmex Corporation. Further, the tissue after crushing with a water flow was crushed at an output intensity of 20% for 30 seconds in 1 mL of TBS in an ice-cooled environment by an ultrasonic crushing apparatus (VCX130PB) from Sonics & Materials, Inc.

1-7. Immunofluorescent Staining

The same procedure as in Reference Example 2 was carried out.

1-8. Flow Cytometer Measurement

The same procedure as in Reference Example 2 was carried out.

1-9. Calculation of Cytokeratin and Ki-67-Positive Ratios

For analysis of the obtained measurement data, software FlowJo v10 manufactured by FLOWJO LLC was used. In a chart with the fluorescence intensities of DAPI in the horizontal axis and the number of cells (nuclei) in the vertical axis, an area in which the fluorescence intensities in the horizontal axis are 5 to 150 was gated as cell nuclei. The cytokeratin- and Ki-67-positive ratios in the area were calculated as ratios of the number of cytokeratin-positive nuclei and the number of Ki-67-positive nuclei with respect to the number of all cell nuclei. The threshold values of positive nuclei were set to the 60, 70, 80 and 95 percentile values of the isotype controls. The positive ratio was calculated by the formula: positive ratio=a flow-cytometric detection value−(100−threshold value).

2. Results

Figure 23:
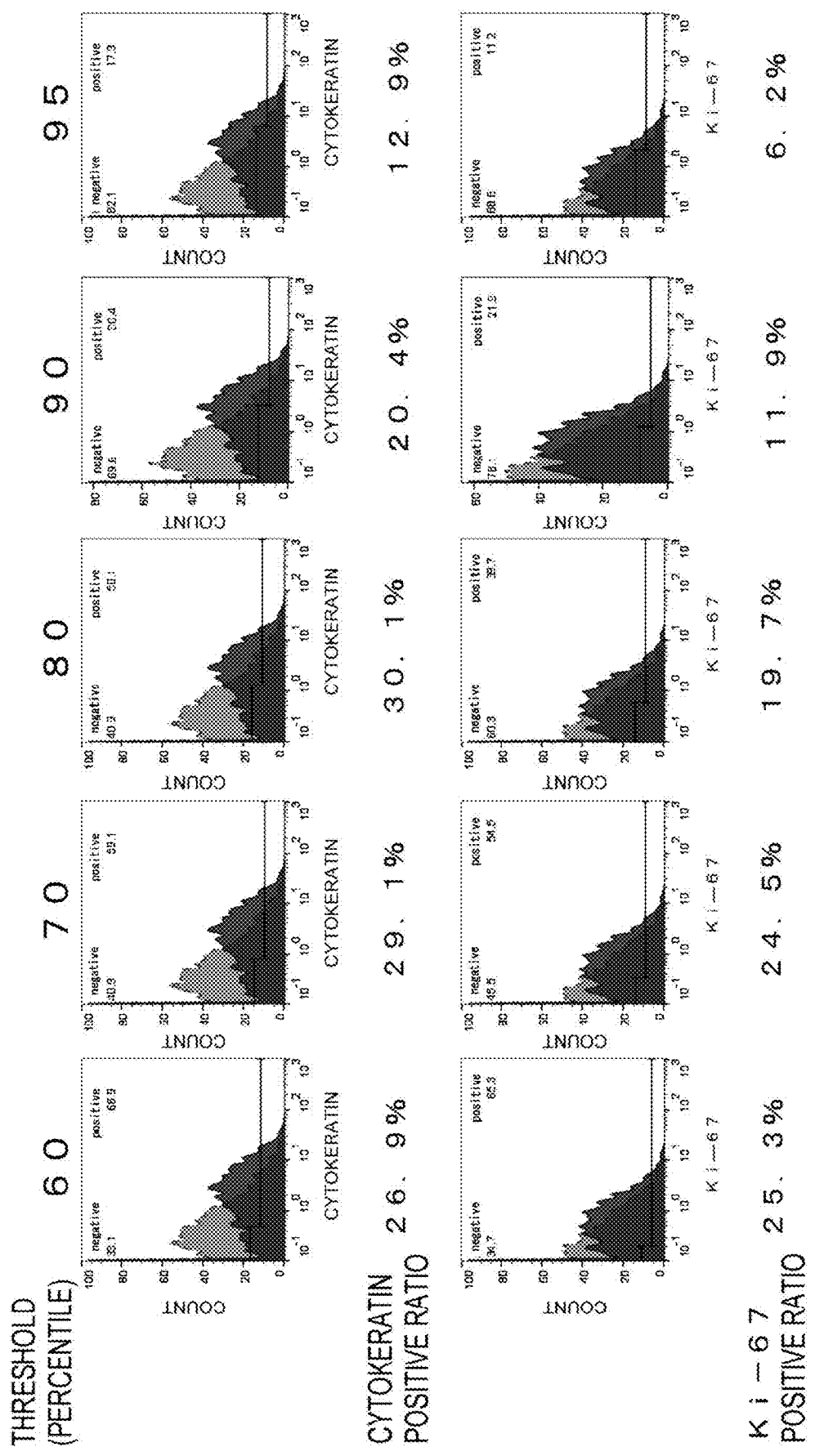
FIG. 23 shows histograms with the fluorescence intensity in the horizontal axis and the number of cells (nuclei) in the vertical axis wherein the histograms were obtained through a process in which a FFPE tissue section of a breast cancer tissue was deparaffinized/hydrophilized, subjected to antigen retrieval with heat treatment, and subjected to antigen activation with thrombin, the cells were crushed with a water flow, crushed with ultrasonication, then immunofluorescently stained with an anti-cytokeratin antibody and an anti-Ki-67 antibody or isotype control antibodies thereof, and then measured by a flow cytometer, and the data of fractions gated as a group of cell nuclei. These diagrams show positive ratios where a threshold of positive nuclei is changed.

FIG. 23 shows charts obtained by overlaying histograms of the fluorescence intensities detected with the anti-cytokeratin antibody and the anti-Ki-67 antibody (black slid lines) and histograms of fluorescence intensities detected with the isotype control antibodies thereof (gray broken lines), while changing a threshold. The positive ratios could be calculated in all the threshold values. Therefore, the cytokeratin- and Ki-67-positive ratios can be calculated irrespective of the threshold.

Example 15

Detection of HER2 in FFPE Tissue Section

1. Materials and Method

From each of FFPE tissue sections known to be HER2-positive (specimen A: Score 3+) and HER2-negative (specimen B: Score 0), cell nuclei were extracted by crushing them with a water flow and crushing them with ultrasonication, and amplification of HER2 was examined by a FISH method.

1-1. FFPE Tissue Block

The FFPE tissue block used in Reference Example 1 was used.

1-2. Preparation of FFPE Section

The same procedure as in Reference Example 3 was carried out.

1-3. Deparaffinization/Hydrophilization

The same procedure as in Reference Example 1 was carried out.

1-4. Antigen Retrieval with Heat Treatment

The same procedure as in Reference Example 1 was carried out.

1-5. Antigen Activation Treatment with Enzyme

The same procedure as in Example 1 was carried out.

1-6. Combination of Crushing with Water Flow and Crushing with Ultrasonication

The tissue treated with enzyme was crushed at 10,000 rpm for 1 minute in 1 mL of TBS in an ice-cooled environment by a water flow shear apparatus (RP-10) from Sysmex Corporation. Further, the tissue after crushing it with a water flow was crushed at an output intensity of 20% for 30 seconds in 1 mL of TBS in an ice-cooled environment by an ultrasonic crushing apparatus (VCX130PB) from Sonics & Materials, Inc.

1-7. Detection of HER2 by FISH

A sample after tissue crushing was placed on slide glass, dried, and then immersed in 10% formalin neutral buffer at room temperature for 10 minutes. The slide glass was washed with TBS, and air-dried, followed by performing FISH staining with PathVysion (R) HER-2 DNA Probe Kit (Abbot) in accordance with the kit package insert.

1-8. Fluorescence Microscope

For microscopic observation, All-in-One Fluorescence Microscope BZ-X710 (KEYENCE) was used. DAPI Filter (Ex 360 µm, Em 460 µm) and TRITC Filter (Ex 545 µm, Em 605 µm) were used during observation. The magnification of the objective lens was 20 times.

2. Results

Figure 24:
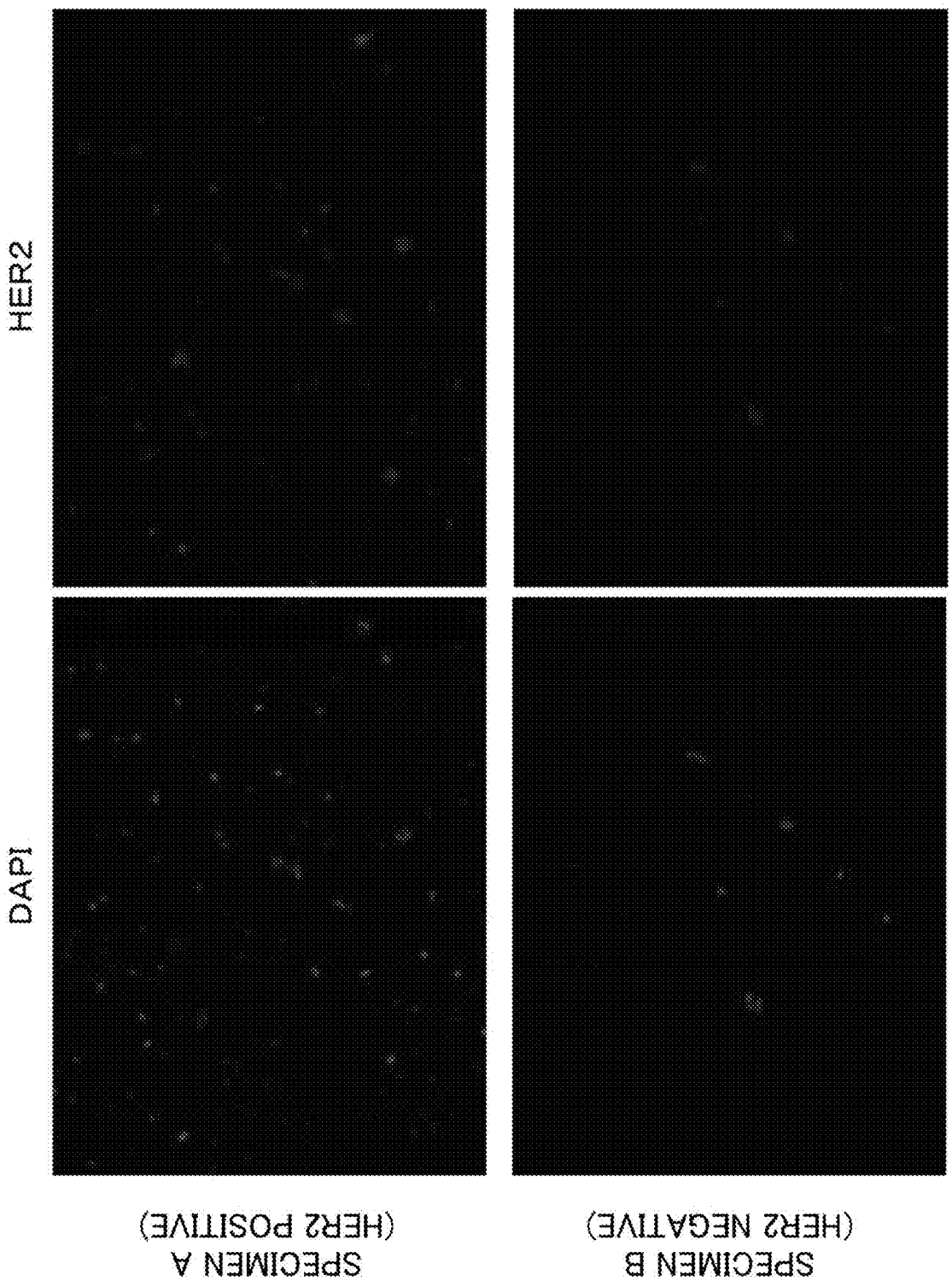
FIG. 24 shows images obtained through a process in which FFPE tissue sections known to be HER2-positive and negative were deparaffinized/hydrophilized, subjected to antigen retrieval with heat treatment, and subjected to antigen activation with thrombin, the cells were crushed with a water flow and crushed with ultrasonication, and the HER2 gene was then fluorescently stained by the FISH method using a fluorescently labeled DNA probe, and observed with a fluorescence microscope.

FIG. 24 shows cell nuclei observed with a fluorescence microscope. It was confirmed that a fluorescence signal derived from HER2 was detected in the HER2-positive FFPE tissue section, and was not detected in the HER2-negative FFPE tissue section.

INDUSTRIAL APPLICABILITY

The present invention has established a method for detecting (quantitatively determining) Ki-67-positive cells with high objectivity, reproducibility and universality. ER-positive cells, PgR-positive cells and Her2-positive cells can be also quantitatively determined thereby enabling classification of endogenous subtypes of cancer.

The present invention provides a protocol (including a pretreatment process including antigen activation with specific enzymes) for isolating cell nuclei containing a target antigen with enhanced antigenicity from a FFPE tissue section. The recovered dispersion can be analyzed at the single cell nucleus level. For example, proteins, nucleic acids or the like on nuclear membranes or in nuclei are objects to be analyzed, and can be detected by morphology observation with a coloring substance (fluorescent) staining or with a ligand such as an antibody labeled with an enzyme or a fluorescent compound, or a nucleic acid. A method, an antigen activator and a kit according to the present invention can be used for morphology observation with a microscope, analysis by IHC, EIA, CLEIA or digital PCR, and cytometric analysis by an imaging cytometer or a flow cytometer, and can be used particularly for calculation of a ratio of positive nuclei containing a target protein to isolated nuclei (in particular, Ki-67-positive ratio) by flow-cytometric analysis according to a preferred embodiment of the present invention.

The protocol (including a pretreatment process including antigen activation with specific enzymes) according to the present invention can provide a pathologically diagnostic indication with small variability.

With the indication with small variability, an optimum therapeutic regimen can be provided to a subject. Anticancer drug treatment itself puts high burden on a subject, and determination of a therapeutic regimen suitable for the subject before starting the therapy is therefore important in maintenance of QOL (quality of life) of the subject. The present invention can be applied to not only therapeutic regimens for chemotherapy before the surgical operation (preoperative anticancer drug treatment) but also (postoperative) therapeutic regimens after removal of tumors by the surgical operation.

The invention claimed is:

1. A method of activating Ki-67 in a population of fixed cells or a fixed tissue comprising pretreating the fixed cells or the fixed tissue with a hydrolase, which does not recognize or cleave the peptide of SEQ ID NO: 2;
   wherein the pretreating occurs after the fixation of cells or tissue.

2. A method for detecting or counting stained Ki-67-positive cells or Ki-67-positive cell nuclei in a population of fixed cells, the method comprising the steps of:
   1) activating Ki-67 in the population of fixed cells according to the method of claim 1,
   2) then, immunostaining the Ki-67 with an anti-Ki-67 antibody, and
   3) detecting stained Ki-67-positive cells or Ki-67-positive cell nuclei, and/or counting Ki-67 positive cells or Ki-67-positive cell nuclei.

3. The method according to claim 2, wherein the anti-Ki-67 antibody is at least one selected from the group consisting of MIB-1, DAKO-PC, Ki-S5 and A-0047.

4. The method according to claim 2, wherein the hydrolase is at least one selected from the group consisting of thrombin, Arg-C(clostripain) peptidase, proline endopeptidase and hyaluronidase.

5. The method according to claim 2, wherein the hydrolase is thrombin and/or hyaluronidase, and the anti-Ki-67 antibody is MIB-1.

6. The method according to claim 2, further comprising applying heat treatment before step 1) to retrieve the Ki-67.

7. The method according to claim 2, wherein the method further comprises immunostaining cytokeratin with an anti-cytokeratin antibody, and detecting stained cytokeratin-positive cells.

8. The method according to claim 2, wherein the method further comprises immunostaining estrogen receptor (ER) and/or progesterone receptor (PgR) with an anti-ER antibody and/or an anti-PgR antibody, respectively, and detecting ER and/or PgR stained positive cells or positive cell nuclei.

9. The method according to claim 2, further comprising detecting cells or cell nuclei having an amplified HER2 gene with a probe which hybridizes with the HER2 gene.

10. The method according to claim 2, wherein the population of fixed cells is contained in a tissue section.

11. The method according to claim 10, wherein the tissue section is embedded in an embedding agent, and the method further comprises the steps of removing the embedding agent and hydrophilizing the tissue section before the step of activating Ki-67 with the hydrolase.

12. The method according to claim 10, further comprising the step of extracting cell nuclei by crushing the cells between steps 1) and 2).

13. The method according to claim 12, wherein the cell nuclei are extracted by at least one of: crushing the cells with shear stress and/or extracted in a buffer solution containing a surfactant, wherein the surfactant is at least one of 3-((3-cholamidopropyl)dimethylammonio)-1-propanesulfonate, nonylphenoxypolyethoxyethanol, and t-octylphenoxypolyethoxyethanol.

14. The method according to claim 2, wherein the Ki-67-positive cells or Ki-67-positive cell nuclei are detected by fluorescence, and counted by a flow cytometry.

15. The method according to claim 2, wherein the population of fixed cells or the fixed tissue is breast cancer cells or a breast cancer tissue, respectively.

16. A method for determining a cancer therapeutic regimen, the method comprising:
   calculating a ratio of Ki-67-positive cells in a population of cells, wherein the Ki-67-positive cells are counted by the method according to claim 2, and
   selecting one of: a combination of endocrine therapy and chemotherapy when the ratio is equal to or more than a cutoff value, or endocrine therapy alone when the ratio is less than the cutoff value.

17. The method according to claim 16, further comprising administering the selected therapy to a subject in need of a cancer treatment.

* * * * *

SEQUENCE LISTING

```
<160> NUMBER OF SEQ ID NOS: 2

<210> SEQ ID NO 1
<211> LENGTH: 3256
<212> TYPE: PRT
<213> ORGANISM: Homo sapiens

<400> SEQUENCE: 1

Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80

Arg Leu Lys His Gly Asp Val Ile Thr Ile Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Asp Ser Val Ala
                165                 170                 175

Gln Gly Thr Thr Asn Val His Ser Ser Glu His Ala Gly Arg Asn Gly
```

```
                180             185             190
Arg Asn Ala Ala Asp Pro Ile Ser Gly Asp Phe Lys Glu Ile Ser Ser
            195                 200                 205

Val Lys Leu Val Ser Arg Tyr Gly Glu Leu Lys Ser Val Pro Thr Thr
210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
    370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
            420                 425                 430

Leu Pro Thr Glu Thr Glu Ile His Asn Glu Pro Phe Leu Thr Leu Trp
        435                 440                 445

Leu Thr Gln Val Glu Arg Lys Ile Gln Lys Asp Ser Leu Ser Lys Pro
    450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495

Glu Gly Ile Pro Leu Lys Arg Arg Val Ser Phe Gly Gly His Leu
            500                 505                 510

Arg Pro Glu Leu Phe Asp Glu Asn Leu Pro Pro Asn Thr Pro Leu Lys
        515                 520                 525

Arg Gly Glu Ala Pro Thr Lys Arg Lys Ser Leu Val Met His Thr Pro
    530                 535                 540

Pro Val Leu Lys Lys Ile Ile Lys Glu Gln Pro Gln Pro Ser Gly Lys
545                 550                 555                 560

Gln Glu Ser Gly Ser Glu Ile His Val Glu Val Lys Ala Gln Ser Leu
                565                 570                 575

Val Ile Ser Pro Pro Ala Pro Ser Pro Arg Lys Thr Pro Val Ala Ser
            580                 585                 590

Asp Gln Arg Arg Arg Ser Cys Lys Thr Ala Pro Ala Ser Ser Ser Lys
        595                 600                 605
```

```
Ser Gln Thr Glu Val Pro Lys Arg Gly Gly Arg Lys Ser Gly Asn Leu
    610                 615                 620
Pro Ser Lys Arg Val Ser Ile Ser Arg Ser Gln His Asp Ile Leu Gln
625                 630                 635                 640
Met Ile Cys Ser Lys Arg Arg Ser Gly Ala Ser Glu Ala Asn Leu Ile
                645                 650                 655
Val Ala Lys Ser Trp Ala Asp Val Val Lys Leu Gly Ala Lys Gln Thr
                660                 665                 670
Gln Thr Lys Val Ile Lys His Gly Pro Gln Arg Ser Met Asn Lys Arg
            675                 680                 685
Gln Arg Arg Pro Ala Thr Pro Lys Lys Pro Val Gly Glu Val His Ser
    690                 695                 700
Gln Phe Ser Thr Gly His Ala Asn Ser Pro Cys Thr Ile Ile Ile Gly
705                 710                 715                 720
Lys Ala His Thr Glu Lys Val His Val Pro Ala Arg Pro Tyr Arg Val
                725                 730                 735
Leu Asn Asn Phe Ile Ser Asn Gln Lys Met Asp Phe Lys Glu Asp Leu
                740                 745                 750
Ser Gly Ile Ala Glu Met Phe Lys Thr Pro Val Lys Glu Gln Pro Gln
            755                 760                 765
Leu Thr Ser Thr Cys His Ile Ala Ile Ser Asn Ser Glu Asn Leu Leu
    770                 775                 780
Gly Lys Gln Phe Gln Gly Thr Asp Ser Gly Glu Glu Pro Leu Leu Pro
785                 790                 795                 800
Thr Ser Glu Ser Phe Gly Gly Asn Val Phe Phe Ser Ala Gln Asn Ala
                805                 810                 815
Ala Lys Gln Pro Ser Asp Lys Cys Ser Ala Ser Pro Pro Leu Arg Arg
                820                 825                 830
Gln Cys Ile Arg Glu Asn Gly Asn Val Ala Lys Thr Pro Arg Asn Thr
            835                 840                 845
Tyr Lys Met Thr Ser Leu Glu Thr Lys Thr Ser Asp Thr Glu Thr Glu
    850                 855                 860
Pro Ser Lys Thr Val Ser Thr Ala Asn Arg Ser Gly Arg Ser Thr Glu
865                 870                 875                 880
Phe Arg Asn Ile Gln Lys Leu Pro Val Glu Ser Lys Ser Glu Glu Thr
                885                 890                 895
Asn Thr Glu Ile Val Glu Cys Ile Leu Lys Arg Gly Gln Lys Ala Thr
                900                 905                 910
Leu Leu Gln Gln Arg Arg Glu Gly Glu Met Lys Glu Ile Glu Arg Pro
            915                 920                 925
Phe Glu Thr Tyr Lys Glu Asn Ile Glu Leu Lys Glu Asn Asp Glu Lys
    930                 935                 940
Met Lys Ala Met Lys Arg Ser Arg Thr Trp Gly Gln Lys Cys Ala Pro
945                 950                 955                 960
Met Ser Asp Leu Thr Asp Leu Lys Ser Leu Pro Asp Thr Glu Leu Met
                965                 970                 975
Lys Asp Thr Ala Arg Gly Gln Asn Leu Leu Gln Thr Gln Asp His Ala
                980                 985                 990
Lys Ala Pro Lys Ser Glu Lys Gly Lys Ile Thr Lys Met Pro Cys Gln
            995                 1000                1005
Ser Leu Gln Pro Glu Pro Ile Asn Thr Pro Thr His Thr Lys Gln
    1010                1015                1020
```

```
Gln Leu Lys Ala Ser Leu Gly Lys Val Gly Val Lys Glu Glu Leu
    1025                1030                1035

Leu Ala Val Gly Lys Phe Thr Arg Thr Ser Gly Glu Thr Thr His
    1040                1045                1050

Thr His Arg Glu Pro Ala Gly Asp Gly Lys Ser Ile Arg Thr Phe
    1055                1060                1065

Lys Glu Ser Pro Lys Gln Ile Leu Asp Pro Ala Ala Arg Val Thr
    1070                1075                1080

Gly Met Lys Lys Trp Pro Arg Thr Pro Lys Glu Glu Ala Gln Ser
    1085                1090                1095

Leu Glu Asp Leu Ala Gly Phe Lys Glu Leu Phe Gln Thr Pro Gly
    1100                1105                1110

Pro Ser Glu Glu Ser Met Thr Asp Glu Lys Thr Thr Lys Ile Ala
    1115                1120                1125

Cys Lys Ser Pro Pro Pro Glu Ser Val Asp Thr Pro Thr Ser Thr
    1130                1135                1140

Lys Gln Trp Pro Lys Arg Ser Leu Arg Lys Ala Asp Val Glu Glu
    1145                1150                1155

Glu Phe Leu Ala Leu Arg Lys Leu Thr Pro Ser Ala Gly Lys Ala
    1160                1165                1170

Met Leu Thr Pro Lys Pro Ala Gly Gly Asp Glu Lys Asp Ile Lys
    1175                1180                1185

Ala Phe Met Gly Thr Pro Val Gln Lys Leu Asp Leu Ala Gly Thr
    1190                1195                1200

Leu Pro Gly Ser Lys Arg Gln Leu Gln Thr Pro Lys Glu Lys Ala
    1205                1210                1215

Gln Ala Leu Glu Asp Leu Ala Gly Phe Lys Glu Leu Phe Gln Thr
    1220                1225                1230

Pro Gly His Thr Glu Glu Leu Val Ala Ala Gly Lys Thr Thr Lys
    1235                1240                1245

Ile Pro Cys Asp Ser Pro Gln Ser Asp Pro Val Asp Thr Pro Thr
    1250                1255                1260

Ser Thr Lys Gln Arg Pro Lys Arg Ser Ile Arg Lys Ala Asp Val
    1265                1270                1275

Glu Gly Glu Leu Leu Ala Cys Arg Asn Leu Met Pro Ser Ala Gly
    1280                1285                1290

Lys Ala Met His Thr Pro Lys Pro Ser Val Gly Glu Glu Lys Asp
    1295                1300                1305

Ile Ile Ile Phe Val Gly Thr Pro Val Gln Lys Leu Asp Leu Thr
    1310                1315                1320

Glu Asn Leu Thr Gly Ser Lys Arg Arg Pro Gln Thr Pro Lys Glu
    1325                1330                1335

Glu Ala Gln Ala Leu Glu Asp Leu Thr Gly Phe Lys Glu Leu Phe
    1340                1345                1350

Gln Thr Pro Gly His Thr Glu Glu Ala Val Ala Ala Gly Lys Thr
    1355                1360                1365

Thr Lys Met Pro Cys Glu Ser Ser Pro Pro Glu Ser Ala Asp Thr
    1370                1375                1380

Pro Thr Ser Thr Arg Arg Gln Pro Lys Thr Pro Leu Glu Lys Arg
    1385                1390                1395

Asp Val Gln Lys Glu Leu Ser Ala Leu Lys Lys Leu Thr Gln Thr
    1400                1405                1410

Ser Gly Glu Thr Thr His Thr Asp Lys Val Pro Gly Gly Glu Asp
```

```
              1415                 1420                  1425

Lys Ser Ile Asn Ala Phe Arg Glu Thr Ala Lys Gln Lys Leu Asp
    1430                1435                1440

Pro Ala Ala Ser Val Thr Gly Ser Lys Arg His Pro Lys Thr Lys
    1445                1450                1455

Glu Lys Ala Gln Pro Leu Glu Asp Leu Ala Gly Leu Lys Glu Leu
    1460                1465                1470

Phe Gln Thr Pro Val Cys Thr Asp Lys Pro Thr Thr His Glu Lys
    1475                1480                1485

Thr Thr Lys Ile Ala Cys Arg Ser Gln Pro Asp Pro Val Asp Thr
    1490                1495                1500

Pro Thr Ser Ser Lys Pro Gln Ser Lys Arg Ser Leu Arg Lys Val
    1505                1510                1515

Asp Val Glu Glu Glu Phe Phe Ala Leu Arg Lys Arg Thr Pro Ser
    1520                1525                1530

Ala Gly Lys Ala Met His Thr Pro Lys Pro Ala Val Ser Gly Glu
    1535                1540                1545

Lys Asn Ile Tyr Ala Phe Met Gly Thr Pro Val Gln Lys Leu Asp
    1550                1555                1560

Leu Thr Glu Asn Leu Thr Gly Ser Lys Arg Arg Leu Gln Thr Pro
    1565                1570                1575

Lys Glu Lys Ala Gln Ala Leu Glu Asp Leu Ala Gly Phe Lys Glu
    1580                1585                1590

Leu Phe Gln Thr Arg Gly His Thr Glu Glu Ser Met Thr Asn Asp
    1595                1600                1605

Lys Thr Ala Lys Val Ala Cys Lys Ser Ser Gln Pro Asp Pro Asp
    1610                1615                1620

Lys Asn Pro Ala Ser Ser Lys Arg Arg Leu Lys Thr Ser Leu Gly
    1625                1630                1635

Lys Val Gly Val Lys Glu Glu Leu Leu Ala Val Gly Lys Leu Thr
    1640                1645                1650

Gln Thr Ser Gly Glu Thr His Thr His Thr Glu Pro Thr Gly
    1655                1660                1665

Asp Gly Lys Ser Met Lys Ala Phe Met Glu Ser Pro Lys Gln Ile
    1670                1675                1680

Leu Asp Ser Ala Ala Ser Leu Thr Gly Ser Lys Arg Gln Leu Arg
    1685                1690                1695

Thr Pro Lys Gly Lys Ser Glu Val Pro Glu Asp Leu Ala Gly Phe
    1700                1705                1710

Ile Glu Leu Phe Gln Thr Pro Ser His Thr Lys Glu Ser Met Thr
    1715                1720                1725

Asn Glu Lys Thr Thr Lys Val Ser Tyr Arg Ala Ser Gln Pro Asp
    1730                1735                1740

Leu Val Asp Thr Pro Thr Ser Ser Lys Pro Gln Pro Lys Arg Ser
    1745                1750                1755

Leu Arg Lys Ala Asp Thr Glu Glu Phe Leu Ala Phe Arg Lys
    1760                1765                1770

Gln Thr Pro Ser Ala Gly Lys Ala Met His Thr Pro Lys Pro Ala
    1775                1780                1785

Val Gly Glu Glu Lys Asp Ile Asn Thr Phe Leu Gly Thr Pro Val
    1790                1795                1800

Gln Lys Leu Asp Gln Pro Gly Asn Leu Pro Gly Ser Asn Arg Arg
    1805                1810                1815
```

```
Leu Gln Thr Arg Lys Glu Lys Ala Gln Ala Leu Glu Glu Leu Thr
    1820            1825                1830
Gly Phe Arg Glu Leu Phe Gln Thr Pro Cys Thr Asp Asn Pro Thr
    1835            1840                1845
Thr Asp Glu Lys Thr Thr Lys Lys Ile Leu Cys Lys Ser Pro Gln
    1850            1855                1860
Ser Asp Pro Ala Asp Thr Pro Thr Asn Thr Lys Gln Arg Pro Lys
    1865            1870                1875
Arg Ser Leu Lys Lys Ala Asp Val Glu Glu Phe Leu Ala Phe
    1880            1885                1890
Arg Lys Leu Thr Pro Ser Ala Gly Lys Ala Met His Thr Pro Lys
    1895            1900                1905
Ala Ala Val Gly Glu Glu Lys Asp Ile Asn Thr Phe Val Gly Thr
    1910            1915                1920
Pro Val Glu Lys Leu Asp Leu Leu Gly Asn Leu Pro Gly Ser Lys
    1925            1930                1935
Arg Arg Pro Gln Thr Pro Lys Glu Lys Ala Lys Ala Leu Glu Asp
    1940            1945                1950
Leu Ala Gly Phe Lys Glu Leu Phe Gln Thr Pro Gly His Thr Glu
    1955            1960                1965
Glu Ser Met Thr Asp Asp Lys Ile Thr Glu Val Ser Cys Lys Ser
    1970            1975                1980
Pro Gln Pro Asp Pro Val Lys Thr Pro Thr Ser Ser Lys Gln Arg
    1985            1990                1995
Leu Lys Ile Ser Leu Gly Lys Val Gly Val Lys Glu Glu Val Leu
    2000            2005                2010
Pro Val Gly Lys Leu Thr Gln Thr Ser Gly Lys Thr Thr Gln Thr
    2015            2020                2025
His Arg Glu Thr Ala Gly Asp Gly Lys Ser Ile Lys Ala Phe Lys
    2030            2035                2040
Glu Ser Ala Lys Gln Met Leu Asp Pro Ala Asn Tyr Gly Thr Gly
    2045            2050                2055
Met Glu Arg Trp Pro Arg Thr Pro Lys Glu Glu Ala Gln Ser Leu
    2060            2065                2070
Glu Asp Leu Ala Gly Phe Lys Glu Leu Phe Gln Thr Pro Asp His
    2075            2080                2085
Thr Glu Glu Ser Thr Thr Asp Asp Lys Thr Thr Lys Ile Ala Cys
    2090            2095                2100
Lys Ser Pro Pro Pro Glu Ser Met Asp Thr Pro Thr Ser Thr Arg
    2105            2110                2115
Arg Arg Pro Lys Thr Pro Leu Gly Lys Arg Asp Ile Val Glu Glu
    2120            2125                2130
Leu Ser Ala Leu Lys Gln Leu Thr Gln Thr Thr His Thr Asp Lys
    2135            2140                2145
Val Pro Gly Asp Glu Asp Lys Gly Ile Asn Val Phe Arg Glu Thr
    2150            2155                2160
Ala Lys Gln Lys Leu Asp Pro Ala Ala Ser Val Thr Gly Ser Lys
    2165            2170                2175
Arg Gln Pro Arg Thr Pro Lys Gly Lys Ala Gln Pro Leu Glu Asp
    2180            2185                2190
Leu Ala Gly Leu Lys Glu Leu Phe Gln Thr Pro Ile Cys Thr Asp
    2195            2200                2205
```

```
Lys Pro Thr Thr His Glu Lys Thr Thr Lys Ile Ala Cys Arg Ser
    2210            2215            2220

Pro Gln Pro Asp Pro Val Gly Thr Pro Thr Ile Phe Lys Pro Gln
    2225            2230            2235

Ser Lys Arg Ser Leu Arg Lys Ala Asp Val Glu Glu Glu Ser Leu
    2240            2245            2250

Ala Leu Arg Lys Arg Thr Pro Ser Val Gly Lys Ala Met Asp Thr
    2255            2260            2265

Pro Lys Pro Ala Gly Gly Asp Glu Lys Asp Met Lys Ala Phe Met
    2270            2275            2280

Gly Thr Pro Val Gln Lys Leu Asp Leu Pro Gly Asn Leu Pro Gly
    2285            2290            2295

Ser Lys Arg Trp Pro Gln Thr Pro Lys Glu Lys Ala Gln Ala Leu
    2300            2305            2310

Glu Asp Leu Ala Gly Phe Lys Glu Leu Phe Gln Thr Pro Gly Thr
    2315            2320            2325

Asp Lys Pro Thr Thr Asp Glu Lys Thr Thr Lys Ile Ala Cys Lys
    2330            2335            2340

Ser Pro Gln Pro Asp Pro Val Asp Thr Pro Ala Ser Thr Lys Gln
    2345            2350            2355

Arg Pro Lys Arg Asn Leu Arg Lys Ala Asp Val Glu Glu Glu Phe
    2360            2365            2370

Leu Ala Leu Arg Lys Arg Thr Pro Ser Ala Gly Lys Ala Met Asp
    2375            2380            2385

Thr Pro Lys Pro Ala Val Ser Asp Glu Lys Asn Ile Asn Thr Phe
    2390            2395            2400

Val Glu Thr Pro Val Gln Lys Leu Asp Leu Leu Gly Asn Leu Pro
    2405            2410            2415

Gly Ser Lys Arg Gln Pro Gln Thr Pro Lys Glu Lys Ala Glu Ala
    2420            2425            2430

Leu Glu Asp Leu Val Gly Phe Lys Glu Leu Phe Gln Thr Pro Gly
    2435            2440            2445

His Thr Glu Glu Ser Met Thr Asp Asp Lys Ile Thr Glu Val Ser
    2450            2455            2460

Cys Lys Ser Pro Gln Pro Glu Ser Phe Lys Thr Ser Arg Ser Ser
    2465            2470            2475

Lys Gln Arg Leu Lys Ile Pro Leu Val Lys Val Asp Met Lys Glu
    2480            2485            2490

Glu Pro Leu Ala Val Ser Lys Leu Thr Arg Thr Ser Gly Glu Thr
    2495            2500            2505

Thr Gln Thr His Thr Glu Pro Thr Gly Asp Ser Lys Ser Ile Lys
    2510            2515            2520

Ala Phe Lys Glu Ser Pro Lys Gln Ile Leu Asp Pro Ala Ala Ser
    2525            2530            2535

Val Thr Gly Ser Arg Arg Gln Leu Arg Thr Arg Lys Glu Lys Ala
    2540            2545            2550

Arg Ala Leu Glu Asp Leu Val Asp Phe Lys Glu Leu Phe Ser Ala
    2555            2560            2565

Pro Gly His Thr Glu Glu Ser Met Thr Ile Asp Lys Asn Thr Lys
    2570            2575            2580

Ile Pro Cys Lys Ser Pro Pro Pro Glu Leu Thr Asp Thr Ala Thr
    2585            2590            2595

Ser Thr Lys Arg Cys Pro Lys Thr Arg Pro Arg Lys Glu Val Lys
```

```
              2600                2605                2610
Glu Glu Leu Ser Ala Val Glu Arg Leu Thr Gln Thr Ser Gly Gln
    2615                2620                2625

Ser Thr His Thr His Lys Glu Pro Ala Ser Gly Asp Glu Gly Ile
    2630                2635                2640

Lys Val Leu Lys Gln Arg Ala Lys Lys Lys Pro Asn Pro Val Glu
    2645                2650                2655

Glu Glu Pro Ser Arg Arg Pro Arg Ala Pro Lys Glu Lys Ala
    2660                2665                2670

Gln Pro Leu Glu Asp Leu Ala Gly Phe Thr Glu Leu Ser Glu Thr
    2675                2680                2685

Ser Gly His Thr Gln Glu Ser Leu Thr Ala Gly Lys Ala Thr Lys
    2690                2695                2700

Ile Pro Cys Glu Ser Pro Pro Leu Glu Val Val Asp Thr Thr Ala
    2705                2710                2715

Ser Thr Lys Arg His Leu Arg Thr Arg Val Gln Lys Val Gln Val
    2720                2725                2730

Lys Glu Glu Pro Ser Ala Val Lys Phe Thr Gln Thr Ser Gly Glu
    2735                2740                2745

Thr Thr Asp Ala Asp Lys Glu Pro Ala Gly Glu Asp Lys Gly Ile
    2750                2755                2760

Lys Ala Leu Lys Glu Ser Ala Lys Gln Thr Pro Ala Pro Ala Ala
    2765                2770                2775

Ser Val Thr Gly Ser Arg Arg Pro Arg Ala Pro Arg Glu Ser
    2780                2785                2790

Ala Gln Ala Ile Glu Asp Leu Ala Gly Phe Lys Asp Pro Ala Ala
    2795                2800                2805

Gly His Thr Glu Glu Ser Met Thr Asp Asp Lys Thr Thr Lys Ile
    2810                2815                2820

Pro Cys Lys Ser Ser Pro Glu Leu Glu Asp Thr Ala Thr Ser Ser
    2825                2830                2835

Lys Arg Arg Pro Arg Thr Arg Ala Gln Lys Val Glu Val Lys Glu
    2840                2845                2850

Glu Leu Leu Ala Val Gly Lys Leu Thr Gln Thr Ser Gly Glu Thr
    2855                2860                2865

Thr His Thr Asp Lys Glu Pro Val Gly Glu Gly Lys Gly Thr Lys
    2870                2875                2880

Ala Phe Lys Gln Pro Ala Lys Arg Lys Leu Asp Ala Glu Asp Val
    2885                2890                2895

Ile Gly Ser Arg Arg Gln Pro Arg Ala Pro Lys Glu Lys Ala Gln
    2900                2905                2910

Pro Leu Glu Asp Leu Ala Ser Phe Gln Glu Leu Ser Gln Thr Pro
    2915                2920                2925

Gly His Thr Glu Glu Leu Ala Asn Gly Ala Ala Asp Ser Phe Thr
    2930                2935                2940

Ser Ala Pro Lys Gln Thr Pro Asp Ser Gly Lys Pro Leu Lys Ile
    2945                2950                2955

Ser Arg Arg Val Leu Arg Ala Pro Lys Val Glu Pro Val Gly Asp
    2960                2965                2970

Val Val Ser Thr Arg Asp Pro Val Lys Ser Gln Ser Lys Ser Asn
    2975                2980                2985

Thr Ser Leu Pro Pro Leu Pro Phe Lys Arg Gly Gly Gly Lys Asp
    2990                2995                3000
```

-continued

```
Gly Ser Val Thr Gly Thr Lys Arg Leu Arg Cys Met Pro Ala Pro
    3005            3010                3015
Glu Glu Ile Val Glu Glu Leu Pro Ala Ser Lys Lys Gln Arg Val
    3020            3025                3030
Ala Pro Arg Ala Arg Gly Lys Ser Ser Glu Pro Val Val Ile Met
    3035            3040                3045
Lys Arg Ser Leu Arg Thr Ser Ala Lys Arg Ile Glu Pro Ala Glu
    3050            3055                3060
Glu Leu Asn Ser Asn Asp Met Lys Thr Asn Lys Glu Glu His Lys
    3065            3070                3075
Leu Gln Asp Ser Val Pro Glu Asn Lys Gly Ile Ser Leu Arg Ser
    3080            3085                3090
Arg Arg Gln Asn Lys Thr Glu Ala Glu Gln Ile Thr Glu Val
    3095            3100                3105
Phe Val Leu Ala Glu Arg Ile Glu Ile Asn Arg Asn Glu Lys Lys
    3110            3115                3120
Pro Met Lys Thr Ser Pro Glu Met Asp Ile Gln Asn Pro Asp Asp
    3125            3130                3135
Gly Ala Arg Lys Pro Ile Pro Arg Asp Lys Val Thr Glu Asn Lys
    3140            3145                3150
Arg Cys Leu Arg Ser Ala Arg Gln Asn Glu Ser Ser Gln Pro Lys
    3155            3160                3165
Val Ala Glu Glu Ser Gly Gly Gln Lys Ser Ala Lys Val Leu Met
    3170            3175                3180
Gln Asn Gln Lys Gly Lys Gly Glu Ala Gly Asn Ser Asp Ser Met
    3185            3190                3195
Cys Leu Arg Ser Arg Lys Thr Lys Ser Gln Pro Ala Ala Ser Thr
    3200            3205                3210
Leu Glu Ser Lys Ser Val Gln Arg Val Thr Arg Ser Val Lys Arg
    3215            3220                3225
Cys Ala Glu Asn Pro Lys Lys Ala Glu Asp Asn Val Cys Val Lys
    3230            3235                3240
Lys Ile Arg Thr Arg Ser His Arg Asp Ser Glu Asp Ile
    3245            3250                3255
```

<210> SEQ ID NO 2
<211> LENGTH: 21
<212> TYPE: PRT
<213> ORGANISM: Artificial Sequence
<220> FEATURE:
<223> OTHER INFORMATION: Ki-67 epitope for MIB-1 antibody

<400> SEQUENCE: 2

```
Thr Pro Lys Glu Lys Ala Gln Ala Leu Glu Asp Leu Ala Gly Phe Lys
1               5                   10                  15

Glu Leu Phe Gln Thr
            20
```